US006620615B1

(12) United States Patent
Gould-Rothberg

(10) Patent No.: US 6,620,615 B1
(45) Date of Patent: Sep. 16, 2003

(54) G-PROTEIN COUPLED RECEPTOR—ENCODING NUCLEIC ACIDS

(75) Inventor: Bonnie Gould-Rothberg, Guilford, CT (US)

(73) Assignee: CuraGen Corporation, New Haven, CT (US)

( * ) Notice: Subject to any disclaimer, the term of this patent is extended or adjusted under 35 U.S.C. 154(b) by 0 days.

(21) Appl. No.: 09/556,002

(22) Filed: Apr. 20, 2000

Related U.S. Application Data
(60) Provisional application No. 60/130,817, filed on Apr. 23, 1999.

(51) Int. Cl.[7] .................. C12N 15/85; C12N 15/63; C12N 15/00; C07H 21/04; C07K 14/00
(52) U.S. Cl. ............... 435/325; 435/252.3; 435/254.11; 435/254.2; 435/320.1; 435/69.1; 536/235; 530/350
(58) Field of Search .................. 435/69.1, 71.1, 435/71.2, 325, 320.1; 530/350; 536/23.1, 23.5, 24.1

(56) References Cited

U.S. PATENT DOCUMENTS 5,871,697 A  2/1999  Rothberg et al.

FOREIGN PATENT DOCUMENTS

| EP | 0 899 332 | 3/1999 |
| WO | WO 99/03883 | 1/1999 |
| WO | WO 99/24463 | 5/1999 |
| WO | WO 99/33876 | 7/1999 |
| WO | WO 99/52945 | 10/1999 |
| WO | WO 00/26369 | 5/2000 |
| WO | WO 00/31258 | 6/2000 |

OTHER PUBLICATIONS

Ji et al. 1998. J Biol Chem. vol. 273, pp. 17299–17302. G prote4in coupled receptors. I. Diversity of receptor ligand interactions.*
Yan et al. 2000. Science vol. 29, pp. 523–527. Two–amino acid molecular switch in an epithelial morphogen that regulates binding to two dsitinct receptors.*
Ansubel et al. 1999. Short Protocols in Molecular Biology. Chapter 16.11. pp. 56–57. Overview of Protein Expression in mammalian cells.*
Grimaldi et al, GenBank, Accession No. X01020, Jun. 22, 1995.*
Hendriks et al, GenBank, Accession No. S49226, May 8, 1993.*
Mikayama et al. Molecular cloning and functional expression of a cDNA encoding glycosylation–inhibiting factor. 1993, Proc Natl Acad Sci USA. vol. 90, pp. 10056–10060.*
Voet et al. Biochemistry, John Wiley & Sons, Inc. pp. 126–128, and 228–234.*

Alami, Y., V. Castronovo, et al. (1999). "HOXC5 and HOXC8 expression are selectively turned on in human cervical cancer cells compared to normal keratinocytes." Biochem Biophys Res Commun 257(3): 738–45.
Bodey, B., B. Bodey, Jr., et al. (1998). "Upregulation of endoglin (CD105) expression during childhood brain tumor–related angiogenesis. Anti–angiogenic therapy." Anticancer Res 18(3A): 1485–500.
Colombo, M. P., G. Ferrari, et al. (1991) "Down–regulation of SPAR/osteonectin/BM–40 expression in methylcholanthrene–induced fibrosarcomas and in Kirsten–MSV transformed fibroblasts." Eur J Cancer 27(1): 58–62.
Dameron, K. M., O. V. Volpert, et al. (1994). "Control of angiogenesis in fibroblasts by p53 regulation of thrombospondin–1." Science 265(5178): 1582–4.
GenBank Accession No. ACC S63848, Sep. 14, 1993.
GenBank Accession No. ACC Q20220, Nov. 1, 1996.
GenBank Accession No. ACC AF088916, Jul. 4, 1999.
GenBank Accession No. ACC AF153366, Sep. 29, 1999.
GenBank Accession No. ACC U89942, Mar. 16, 1987.
Genini, M.,, P. Schwalbe, et al. (1996). "Isolation of genes differentially expressed in human primary myoblasts and embryonal rhabdomyosarcoma." Int J Cancer 66(4): 571–7.
Hunzelmann, N., E. Schonherr, et al. (1995). "Altered immunohistochemical expression of small proteoglycans in the tumor tissue and stroma of basal cell carcinoma." J Invest Dermatol 104(4): 509–13.
Iwaki, T. and J. Tateishi (1991). "Immunohistochemical demonstration of alphaB–crystallin in hamartomas of tuberous sclerosis." Am J Pathol 139(6): 1303–8.
Kahari, V. M. and U. Saarialho–Kere (1997), "Matrix metalloproteinases in skin." Exp Dermatol 6(5): 199–213.
Karonen, T., L. Jeskanen, et al. (1997). "Transforming growth factor beta 1 and its latent form binding protein–1 associate with elastic fibres in human dermis: accumulation in actinic damage and absence in anetoderma." Br J Dermatol 137(1): 51–8.
Leygue, E., L. Snell, et al. (1998). "Expression of lumican in human breast carcinoma." Cancer Res 58(7): 1348–52.

(List continued on next page.)

Primary Examiner—Yvonne Eyler
Assistant Examiner—Ruixiang Li
(74) Attorney, Agent, or Firm—Mintz, Levin, Cohn, Ferris, Glovsky & Popeo, P.C.; Ivor R. Elrifi; Naomi S. Biswas

(57) ABSTRACT

Disclosed is a nucleic acid encoding a novel G-protein coupled receptor and methods of using the same. The novel-G-protein coupled receptor was identified as a member of a set of genes that are differentially expressed in diseased fibroblasts relative to non-diseased fibroblasts. The invention also provides methods for identifying and treating disease based on the set of differentially expressed sequences.

8 Claims, No Drawings

OTHER PUBLICATIONS

Menouny, M., M. Binoux, et al. (1998). "IGFBP–2 expression in a human cell line is associated with increased IGFBP–3 proteolysis, decreased IGFBP–1 expression and increased tumorigenicity." *Int J Cancer* 77(6):874–9.

Murphy, M., M. J. Pykett, et al. (1993). "Identification and characterization of genes differentially expressed in meningiomas." *Cell Growth Differ* 4(9): 715–22.

Traish, A. M., Y. H. Huang, et al. (1997). "Loss of expression of a 55 kDa nuclear protein (nmt55) in estrogen receptor–negative human breast cancer." *Diagn Mol Pathol* 6(4): 209–21.

Vider, B. Z., A. Zimber, et al. (1997). "Human colorectal carcinogenesis is associated with deregulation of homeobox gene expression." *Biochem Biophys Res Commun* 232(3): 742–8.

Wang, X., M. A. Peters, et al. (1999). "The Adrenomedullin gene is a target for negative regulation by the Myc transcription complex." *Mol Endocrinol* 13(2): 254–67.

NCBI database, Bethesda, MD, US 14–09–93 AC=S63848. XP002153677.

Abelson, et al., Biochemical and Biophysical Research Communications, 194:504–511 (1993).

International Search Report dated Mar. 5, 2001.

XIAO Guang–Hui et al: "Identification of tuberous sclerosis 2 messenger RNA splice variants that are conserved and differentially expressed in rat and human tissues." Cell Growth & Differentiation, vol. 6, No. 9, 1995, pp. 1185–1190.

NCBI database, Bethesda, MD, US 14–09–98 AC=AI131555. XP002153675.

NCBI database, Bethesda, MD, US 18–10–95 AC=H67224. XP002153676.

Webb D W et al: "The cutaneous features of tuberous sclerosis: A population study." British Journal of Dermatology vol. 135, No. 1, 1996, pp. 1–5.

Au K–S et al: "A severe renal phenotype resulting from a TSC2 mutation without involvement of the PKD1 gene." American Journal of Human Genetics, vol. 61, No. 4 Suppl., Oct. 1997 (1997–10), p. A325.

Jozwiak Sergiusz et al: "Skin lesions in Children with tuberous sclerosis complex: Their prevalence, natural course, and Diagnostic significance." International Journal of Dermatology, vol. 37, No. 12, Dec. 1998 (1998–12), pp. 911–917.

Shimkets R A et al: "Gene expression Analysis by transcript profiling coupled To a gene database query" Nature Biotechnology, Nature Publishing, US, vol. 17, Aug. 1999 (1999–08), pp. 798–803.

Schweickart Viki L et al: "CCR11 is a functional receptor for the monocyte chemoattractant protein family of chemokines." Journal of Biological Chemistry, vol. 275, No. 13, Mar. 31, 2000 (2000–03–31).

Khoja H et al: "Cloning of CCRL1, an orphan seven transmembrane receptor related to chemokine receptors, expressed abundantly in the heart" Gene, NL, Elsevier Biomedical Press. Amsterdam, vol. 246, No. 1–2, Apr. 2000 (2000–04), pp. 229–238.

Gosling J.: "Cutting edge: identification of a novel chemokine receptor that binds Cutting edge: identification of a novel chemokine receptor that binds dendritic cell– and T cell–active chemokines including ELC, SLC, and TECK" J. Immunol., vol. 164, 2000, pp. 2851–2856.

Cheaele Jeremy P et al: "Molecular genetic advances in tuberous sclerosis." Human Genetics, vol. 107, No. 2, Aug. 2000 (2000–08),pp. 97–114.

Majima Shuichi et al: "A novel gene "Niban" upregulated in renal carcinogenesis: Cloning by the cDNA–amplified fragment length polymorphism approach." Japanese Journal of Cancer Research vol. 91, No. 9, Sep. 2000 (2000–09), pp. 869–874.

* cited by examiner

G-PROTEIN COUPLED RECEPTOR— ENCODING NUCLEIC ACIDS

RELATED U.S. APPLICATIONS

This application claims priority to U.S. Ser. No. 60/130,817, filed Apr. 23, 1999, which is incorporated herein by reference in its entirety.

FIELD OF THE INVENTION

The invention relates generally to nucleic acids and polypeptides and more particularly to nucleic acids expressed in different levels in diseased versus non-diseased tissue.

BACKGROUND OF THE INVENTION

G-Protein Coupled Receptors (GPCRs) have been described in a number of species. These receptors typically share a seven transmembrane domain structure that is also observed in neurotransmitter and hormone receptors. These structural similarities may reflect functional similarities in recognition and G-protein-mediated transduction of extracellular signals.

The human GPCR genes are reported to lack introns and to belong to four different gene subfamilies. The subfamilies can display great sequence variability.

SUMMARY OF THE INVENTION

The invention is based in part on the discovery of a human nucleic acid sequence encoding a polypeptide showing homology to a bovine G-protein coupled receptor type B. This sequence was identified as a member of a set of nucleic acids that are differentially expressed in fibroblasts from individuals with conditions associated with tuberous sclerosis complex (TSC) relative to the expression of the nucleic acids in non-TSC fibroblasts. The set of differentially acids is referred to herein as "TSCX" nucleic acids, where "X" is an integer from 1 to 41. A TSC7 nucleic acid according to the invention can encode a G-protein coupled receptor.

The remaining differentially expressed nucleic acids include previously undescribed sequences and nucleic acids sequences that, while previously described, have not heretofore been identified as being expressed in altered levels in TSC individuals.

In one aspect, the invention provides isolated nucleic acid molecule encoding a polypeptide comprising an amino acid sequence of a polypeptide at least 85% identical to a TSCX polypeptide, e.g., a TSC7 polypeptide.

Also provided by the invention is a substantially purified TSCX polypeptide, as well as an antibody which specifically binds to a TSCX polypeptide.

In a further aspect, the invention provides a method of producing a TSCX polypeptide, by culturing a cell containing a TSCX nucleic acid molecule under conditions allowing for expression of a polypeptide encoded by the nucleic acid molecule.

In a still further aspect, the invention provides a method of detecting the presence of a TSCX nucleic acid molecule in a sample by contacting the sample with a nucleic acid probe or primer that selectively binds to the nucleic acid molecule, and then determining whether the nucleic acid probe or primer bound to the TSCX nucleic acid molecule is present in the sample.

In a further aspect, the invention provides a method of detecting the presence of a TSCX polypeptide in a sample by contacting the sample with a compound that selectively binds to the polypeptide under conditions allowing for formation of a complex between the polypeptide and the compound. The complex is then detected, if present, thereby identifying the polypeptide in the sample.

In another aspect, the invention includes a method of modulating the activity of a TSCX polypeptide, e.g., a TSC7 polypeptide, by contacting a cell sample comprising the polypeptide with a compound that binds to the polypeptide in an amount sufficient to modulate the activity of the polypeptide.

In a still further aspect, the invention provides a method for screening for a modulator of activity or of latency or predisposition to a G protein-mediated disorder. The method includes contacting a test compound with a TSC7 polypeptide and determining if the test compound binds to the polypeptide. Binding of the test compound to the polypeptide indicates the test compound is a modulator of activity or of latency or predisposition to a disorder in G-protein mediated pathway method for screening for a modulator of activity or of latency or predisposition to a disorder in a G-protein mediated pathway, the method comprising:

In a further aspect, the invention includes administering a test compound to a test animal suffering from or at increased risk for the G-protein mediated pathway disorder. The test animal recombinantly expresses a polypeptide encoded by a TSC7 nucleic acid sequence. The method includes measuring expression the activity of the recombinantly expressed TSC7 polypeptide in the test animal, and measuring the activity of the polypeptide in a control animal that recombinantly expresses the polypeptide and is not at increased risk for the G-protein mediated pathway disorder. Expression of the polypeptide in the test animal and the control animal is compared. A change in the activity of the polypeptide in the test animal relative to the control animal indicates the test compound is a modulator of activity or of latency or predisposition of a G-protein mediated pathway.

In a further aspect, the invention includes a method for determining the presence of or predisposition to a disease associated with altered levels of an TSCX polypeptide in a subject. The method includes measuring the amount of the polypeptide in a sample from the subject, and comparing the amount of the polypeptide to the amount of the polypeptide present in a control sample. An alteration in the level of the polypeptide in step (a) as compared to the level of the polypeptide in the control sample indicates the presence of or predisposition to a disease in the subject.

In another aspect, the invention provides a method for determining the presence of or predisposition to a disease associated with altered levels of a TSCX nucleic acid molecule. The method includes measuring the amount of the TSCX nucleic acid in a sample from the subject, and comparing the amount of the nucleic acid in step to the amount of the nucleic acid present in a control sample. An alteration in the level of the nucleic acid in the sample as compared to the level of the nucleic acid in the control sample indicates the presence of or predisposition to the disease in the subject.

In a further aspect, the invention provides a method of treating or preventing a pathological condition associated with a disorder in a G-protein mediated pathway by administering a TSC7 polypeptide to a subject in an amount sufficient to alleviate or prevent the disorder.

Also included in the invention is a method of treating or preventing a pathological condition associated with a disorder in a G-protein mediated pathway. The method includes administering a TSC7 nucleic acid to a subject in an amount sufficient to treat or prevent the condition.

In another aspect, the invention includes a method of treating or preventing a pathological condition by administering an antibody to a TSCX polypeptide to a subject in an amount sufficient to alleviate or prevent the pathological condition.

Also included in the invention is a pharmaceutical composition that includes an TSCX nucleic acid, a TSCX polypeptide, and/or an antibody to a TSCX polypeptide, and a pharmaceutically acceptable carrier.

Also provided by the invention is a method of diagnosing a hyperproliferative disorder in a subject. The method includes providing a test cell population from the subject, wherein at least one cell in the test cell population is capable of expressing one or more nucleic acid sequences selected from the group consisting of TSCs: 1–41 and measuring the expression of one or more the nucleic acid sequences in the test cell population. The expression of the nucleic acid sequences is compared to the expression of the nucleic acid sequences in a reference cell population comprising at least one cell whose status with respect to a hyperproliferative disorder is known A difference in expression levels of the TSC sequence, if present, is identified in the test cell population and reference cell population, thereby diagnosing the hyperproliferative disorder in the subject. If desired, expression of one or more genes encoding amartin, tuberin, rap1a, rab5, rabaptin-5, and alpha B crystallin is also compared.

Also provided in the invention is a method of treating a hyperproliferative condition, e.g., a neoplasm and/or a dermatological condition by administering to a subject in need thereof an agent that modulates the expression or activity of one or more nucleic acid sequences selected from the group consisting of TSCs: 1–41.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

The invention provides novel nucleic acids, polypeptides encoded by the novel nucleic acids, and methods of using these sequences. In one aspect, the invention provides a nucleic acid encoding a novel G-protein coupled receptor.

The invention is based in part on the discovery of changes in expression patterns of multiple nucleic acid sequences in human fibroblast cells derived from individuals with the TSC-associated conditions ashleaf spots, shagreen patches, and ungual fibromas.

Cultured fibroblasts were generated from subcutaneous tissue beneath dermatologic lesions in TSC patients and from subcutaneous tissue from normal skin from the same individuals. The cultures were grown to $10^8$ cells, total RNA was recovered and cDNA was prepared. Genes whose transcript levels varied between normal and lesion samples were identified using GENECALLING™ differential expression analysis as described in U.S. Pat. No. 5,871,697 and in Shimkets et al., Nature Biotechnology 17:798–803 (1999).

789 gene fragments were initially found to be differentially expressed in TSC tissue relative to normal tissue. Gene fragments whose expression levels appeared to increase or decrease more than 7-fold compared to normal tissues were selected for further analysis. An unlabeled oligonucleotide competition assay as described in Shimkets et al., Nature Biotechnology 17:198–803 (1999) was used to verify the identity of differentially expressed sequences.

41 single copy nucleic acid sequences whose expression levels differed in TSC tissue and normal tissue were chosen for further characterization. These sequences are referred to herein as TSC: 1–41. A TSC7 nucleic acid according to the invention can encode a novel G-protein coupled receptor.

A summary of the TSC sequences analyzed is presented in Table 1. For previously known sequences, a Genbank sequence database expression number is provided. Also shown are the relative expression levels of the TSC sequence in shagreen, ashleaf, and subungual fibroma tissue, relative to normal tissue. "NEW" indicates expression of the sequence is detected in shagreen, ashleaf, or subingual fibroma tissue, but is not detected in control tissue. "OFF" shows that expression was not detected in shagreen, ashleaf, or subingual fibroma tissue, but was detected in control tissue.

TABLE 1

| Gene | Acc # | Shagreen patch vs. normal | Ashleaf spot vs. normal | Subungual fibroma vs. normal | TSC # | SEQ ID NO: |
|---|---|---|---|---|---|---|
| 2.: SIGNAL TRANSDUCTION | | | | | | |
| 2.1.: PEPTIDE HORMONES/GROWTH FACTORS/CYTOKINES | | | | | | |
| 2.1.1.: PEPTIDE HORMONES | | | | | | |
| Adrenomedullin | D14874 | −2 | −3 | −10 | TSC1 | |
| 2.1.3.: CYTOKINES | | | | | | |
| Pre-B-cell stimulating factor homologue [SDF1b] | L36033 | +2 | −2 | −20 | TSC2 | |
| 2.1.5.: PEPTIDE HORMONE BINDING PROTEINS | | | | | | |
| Insulin-like growth factor binding protein-2 | M35410 | ±1.0 | ±1.5 | +7 | TSC3 | |
| Insulin-like growth factor binding protein-5 | L27560 | −2 | NEW | −4 | TSC4 | |
| Transforming growth factor beta-1 binding protein | M34057 | +2 | −2 | +2 | TSC5 | |
| 2.2.: PEPTIDE RECEPTORS | | | | | | |
| 2.2.1.: TYROSINE KINASE RECEPTORS | | | | | | |
| Endoglin | J05481 | +6 | +5 | +1.0 | TSC6 | |
| 2.2.2.: G-PROTEIN COUPLED RECEPTORS | | | | | | |
| Novel gene fragment, 1637 bp, 82% SI to Cow G-protein coupled receptor type B [S63848] | | +2 | +1.0 | NEW | TSC7 | 1, 2 |

TABLE 1-continued

| Gene | Acc # | Shagreen patch vs. normal | Ashleaf spot vs. normal | Subungual fibroma vs. normal | TSC # | SEQ ID NO: |
|---|---|---|---|---|---|---|
| 2.14.: DNA BINDING PROTEINS | | | | | | |
| 2.14.1.: TRANSCRIPTION FACTORS | | | | | | |
| HOXC8 | X99681 | −2 | +2 | −20 | TSC8 | |
| Region 7 homeobox gene [HOX7] | M97676 | ±1.0 | ±1.0 | +20 | TSC9 | |
| 5.: TISSUE ARCHITECTURE | | | | | | |
| 5.1.: CYTOSKELETON | | | | | | |
| 5.1.1.: COMPONENTS | | | | | | |
| 5.1.1.2.: STRUCTURAL ARM-INTERMEDIATE FILAMENTS | | | | | | |
| Mesothelial keratin K7 [typeII] | X03212 | ±1.0 | ±1.0 | OFF | TSC10 | |
| Cytokeratin-18 | X12881 | +8 | +3 | OFF | TSC11 | |
| 5.1.1.3.: STRUCTURAL ARM-ACTINS AND SHORT FILAMENTS | | | | | | |
| Vascular smooth muscle alpha actin | X13839 | ±1.0 | +10 | −20 | TSC12 | |
| Enteric smooth muscle gamma actin | X16940 | ±1.0 | ±1.0 | −18 | TSC13 | |
| 5.1.2.: CHAPERONE | | | | | | |
| Alpha B crystallin | S45630 | −2 | ±1.0 | −7 | TSC14 | |
| 5.1.3.: REGULATORS | | | | | | |
| 5.1.3.2.: INHIBITORS | | | | | | |
| Macrophage capping protein | M94345 | +3 | −1.5 | +3 | TSC15 | |
| 5.2.: EXTRACELLULAR MATRIX | | | | | | |
| 5.2.1.: ECM COMPONENT | | | | | | |
| Biglycan [bonesmall proteoglycan] | J04599 | ±1.0 | +5 | −8 | TSC16 | |
| Decorin | L01125 | −2 | −2 | +4 | TSC17 | |
| Laminin alpha 4 | X91171 | +3 | −13 | ±1.0 | TSC18 | |
| LAMA3 for laminin AH | X70904 | +3 | +3 | −3 | TSC19 | |
| Lumican | U18728 | ±1.0 | ±1.0 | +20 | TSC20 | |
| Microfibril associated glycoprotein 2 [MAGP-2] | U37283 | −2 | ±1.0 | ±1.0 | TSC21 | |
| SPARC/osteonectin | J03040 | −1.5 | +2 | −2 | TSC22 | |
| Procollagen type IV alpha-1 chain | M11315 | ±1.0 | ±1.0 | −4 | T5C23 | |
| Novel gene fragment, 3579 bp, 50% AA similarity to C. elegans procollagen alpha chain 1 (V) [Q20220] | | O | O | NEW | TSC24 | 3, 4 |
| Novel gene fragment, 647 bp, 48% AA similarity to Human emilin precursor [AF088916] | | ±1.0 | −4 | −4 | TSC25 | 5, 6 |
| Novel gene fragment, 683 bp, 40% AA similarity to Mouse tubulo-interstitial nephritis antigen [AF153366] | | ±1.0 | ±1.0 | −8 | TSC26 | 7, 8 |
| 5.2.2.: ECM BREAKDOWN | | | | | | |
| Type I interstitial collagenase | X54925 | ±1.0 | +2 | NEW | TSC27 | |
| Tissue plasminogen activator | M15518 | ±1.0 | ±1.0 | −4 | TSC28 | |
| 5.2.3.: ECM BREAKDOWN INHIBITION | | | | | | |
| Endothelial plasminogen activator inhibitor [PAI-1] | X04429 | ±1.0 | +3 | −3 | TSC29 | |
| 5.3.: INTERCELLULAR ADHESION | | | | | | |
| 5.3.2.: INTERFACE WITH EXTRACELLULAR MATRIX | | | | | | |
| Fibronectin receptor, alpha subunit | X06256 | +2 | ±1.0 | −2 | TSC30 | |
| Integrin beta-5 subunit | J05633 | ±1.0 | ±1.0 | −1.5 | TSC31 | |
| Thrombospondin | X14787 | ±1.0 | −2 | ±1.0 | TSC32 | |
| Navel gene fragment, 187 bp, 74% SI to human Lysyl oxidase-related protein (WS9-14) [U89942] | | ±1.0 | ±1.0 | NEW | T5C33 | 9, 10 |
| 5.3.3.: INTERFACE WITH OTHER CELLS | | | | | | |
| Osteoblast specific factor-2pl | D13665 | −3 | +4 | −2 | TSC34 | |
| 9.: UNKNOWN FUNCTION | | | | | | |
| 9.1.: KNOWN GENES | | | | | | |
| 9.1.1.: DISEASE ASSOCIATED | | | | | | |
| 9.1.1.1.: CANCER | | | | | | |
| MAC30 Mrna | L19183 | −2 | −8 | ±1.0 | TSC35 | |
| Nuclear matrix protein 55 | U89867 | −2 | +2 | +4 | TSC36 | |
| 9.4.: NOVEL | | | | | | |
| Novel gene fragment, 490 bp | | ±1.0 | −13 | +2 | TSC37 | 11, 12 |
| Novel gene fragment, 404 bp | | −5 | +3 | ±1.0 | TSC38 | 13, 14 |
| Novel gene fragment, 1547 bp (contains Alu fragment 721–1011 bp) | | −7 | +2 | −2 | TSC39 | 15, 16 |
| Novel gene fragment, 192 bp | | ±1.0 | +4 | +3 | TSC40 | 17 |
| Novel gene fragment, 112 bp | | +9 | ±1.0 | −10 | TSC41 | 18 |

Below follows additional discussion of novel nucleic acid sequences whose expression is differentially regulated in fibroblasts derived from TSC lesions.

TSC7, A Novel G-protein Coupled Receptor (GPCR)

A TSC7 nucleic acid molecule according to the invention includes a 1637 bp gene that has 82% sequence identity (SI) to bovine G-protein coupled receptor (GPCR) type B [S63848]. GPCRs are membraneous receptors characterized by a seven transmembrane motif, and are involved in regulation of a variety of cell processes, such as proliferation, migration, adhesion, and possibly cellular transformation. G-protein coupled receptors are structurally similar to neurotransmitter receptors and hormone receptors.

Although this sequence has the highest similarity to a cow gustatory receptor, the expression pattern of this novel GPCR suggests that it may be involved in other processes. For example, E-northern data indicated that this gene is expressed in adrenal glands, brain, breast, epithelial cells, fetal heart, and testis. A nucleotide sequence (SEQ ID NO:1) and encoded polypeptide amino acid sequence (SEQ ID NO:2) (encoded by nucleotides 168–1217 of SEQ ID NO: 1) for a TSC7 nucleic acid molecule according to the invention are presented in Table 2.

adenocarcinoma; lymphoma; prostate cancer; uterus cancer), anorexia, bulimia, asthma, Parkinson's disease, acute heart failure, hypotension, hypertension, urinary retention, osteoporosis, Crohn's disease; multiple sclerosis; and Treatment of Albright Hereditary Ostoeodystrophy,

TABLE 2

```
   1 CAAATAAAAATGGTGGAGTCTGAAAAAGGACTGGGTCAGCAAGAATAAAAACACAAAACAGCTGGAGGAGCCAAGATGGC
  81 CGAATAGGAACAGCTCCGGTCTACAGCTCCCAGCGTGAGCGACGCAGAAGACGGGTGATTTCTGCATTTCCATAACAGAT
 161 TGGAGCCATGGCTTTGGAACAGAACCAGTCAACAGATTATTATTATGAGGAAAATGAAATGAATGGCACTTATGACTACA
          MetAlaLeuGluGlnAsnGlnSerThrAspTyrTyrTyrGluGluAsnGluMetAsnGlyThrTyrAspTyrS
 241 GTCAATATGAACTGATCTGTATCAAAGAAGATGTCAGAGAATTTGCAAAAGTTTTCCTCCCTGTATTCCTCACAATAGTT
        erGlnTyrGluLeuIleCysIleLysGluAspValArgGluPheAlaLysValPheLeuProValPheLeuThrIleVal
 321 TTCGTCATTGGACTTGCAGGCAATTCCATGGTAGTGGCAATTTATGCCTATTACAAGAAACAGACAACCAAAACAGATGT
        PheValIleGlyLeuAlaGlyAsnSerMetValValAlaIleTyrAlaTyrTyrLysLysGlnArgThrLysThrAspVa
 401 GTACATCCTGAATTTGGCTGTAGCAGATTTACTCCTTCTATTCACTCTGCCTTTTTGGGCTGTTAATGCAGTTCATGGGT
        lTyrIleLeuAsnLeuAlaValAlaAspLeuLeuLeuLeuPheThrLeuProPheTrpAlaValAsnAlaValHisGlyT
 481 GGGTTTTAGGGAAAATAATGTGCAAAATAACTTCAGCCTTGTACACACTAAACTTTGTCTCTGGAATGCAGTTTCTGGCT
        rpValLeuGlyLysIleMetCysLysIleThrSerAlaLeuTyrThrLeuAsnPheValSerGlyMetGlnPheLeuAla
 561 TGCATCAGCATAGACAGATATGTGGCAGTAACTAATGTCCCCAGCCAATCAGGAGTGGGAAAACCATGCTGGATCATCTG
        CysIleSerIleAspArgTyrValAlaValThrAsnValProSerGlnSerGlyValGlyLysProCysTrpIleIleCy
 641 TTTCTGTGTCTGGATGGCTGCCATCTTGCTGAGCATACCCCAGCTGGTTTTTTATACAGTAAATGACAATGCTAGGTGCA
        sPheCysValTrpMetAlaAlaIleLeuLeuSerIleProGlnLeuValPheTyrThrValAsnAspAsnAlaArgCysI
 721 TTCCCATTTTCCCCCGCTACCTAGGAACATCAATGAAAGCATTGATTCAAATGCTAGAGATCTGCATTGGATTTGTAGTA
        leProIlePheProArpTyrLeuGlyThrSerMetLysAlaLeuIleGlnMetLeuGluIleCysIleGlyPheValVal
 801 CCCTTTCTTATTATGGGGGTGTGCTACTTTATCACGGCAAGGACACTCATGAAGATGCCAAACATTAAAATATCTCGACC
        ProPheLeuIleMetGlyValCysTyrPheIleThrAlaArgThrLeuMetLysMetProAsnIleLysIleSerArgPr
 881 CCTAAAAGTTCTGCTCACAGTCGTTATAGTTTTCATTGTCACTCAACTGCCTTATAACATTGTCAAGTTCTGCCGAGCCA
        oLeuLysValLeuLeuThrValValIleValPheIleValThrGlnLeuProTyrAsnIleValLysPheCysArgAlaI
 961 TAGACATCATCTACTCTCTGATCACCAGCTGCAACATGAGCAAACGCATGGACATCGCCATCCAAGTCACAGAAAGCATT
        leAspIleIleTyrSerLeuIleThrSerCysAsnMetSerLysArgMetAspIleAlaIleGlnValThrGluSerIle
1041 GCACTCTTTTTACAGCTGCCTCAACCCAATCCTTTATGTTTTTATGGGAGCATCTTTCAAAAACTACGTTATGAAACTGGC
        AlaLeuPheTyrSerCysLeuAsnProIleLeuTyrValPheMetGlyAlaSerPheLysAsnTyrValMetLysValAl
1121 CAAGAAATATGGGTCCTGGAGAAGACAGAGACAAAGTGTGGAGGAGTTTCCTTTTGATTCTGAGGGTCCTACAGAGCCAA
        sLysLysTyrGlySerTrpArgArgGlnArgGlnSerValGluGluPheProPheAspSerGluGlyProThrGluProT
1201 CCAGTACTTTTAGCATTTAAAGGTAAAACTGCTCTGCCTTTTGCTTGGATACATATGAATGATGCTTTCCCCTCAAATAA
        hrSerThrPheSerIle  (SEQ ID NO: 2).
1281 AACATCTGCATTATTCTGAAACTCAAATCTCAGACGCCGTGGTTGCAACTTATAATAAAGAATGGGTTGGGGGAAGGGGG
1361 AGAAATAAAAGCCAAGAAGAGGAACAAGATAATAAATGTACAAAACATGAAAATTAAAATGAACAATATAGGAAAATAAT
1441 TGTAACAGGCATAAGTGAATAACACTCTGCTGTAACGAAGAAGAGCTTTGTGGTGATAATTTTGTATCTTGGTTGCAGTG
1521 GTGCTTATACAAATGTACACAAGTGATAAAATGACACAGAACATATATCACACATTGTACCAATTTCAATTTCCTGGTTT
1601 TGACATTATAGTATAATTATGTAAGATGGAACCATTG (SEQ ID NO: 1).
```

TSC7 nucleic acids and polypeptides according to the invention are useful, inter alia, in in the treatment of infections such as bacterial, fungal, protozoal and viral infections (particularly infections caused by HIV-1 or HIV-2), pain, cancer (including but not limited to Neoplasm; adenocarcinoma; lymphoma; prostate cancer; uterus cancer), anorexia, bulimia, asthma, Parkinson's disease, acute heart failure, hypotension, hypertension, and urinary retention. They can also be used in e.g., treating or preventing osteoporosis, Crohn's disease; multiple sclerosis; and Treatment of Albright Hereditary Ostoeodystrophy, angina pectoris, myocardial infarction, ulcers, asthma, allergies, benign prostatic hypertrophy, and psychotic and neurological disorders, including anxiety, schizophrenia, manic depression, delirium, dementia, severe mental retardation and dyskinesias, such as Huntington's disease or Gilles de la Tourette syndrome and/or other pathologies and disorders.

The polypeptides can be used as immunogens to produce antibodies specific for the invention, and as vaccines. They can also be used to screen for potential agonist and antagonist compounds. For example, a cDNA encoding the GPCR-like protein may be useful in gene therapy, and the GPCR-like protein may be useful when administered to a subject in need thereof By way of nonlimiting example, the compositions of the present invention will have efficacy for treatment of patients suffering from bacterial, fungal, protozoal and viral infections (particularly infections caused by HIV-1 or HIV-2), pain, cancer (including but not limited to Neoplasm;

angina pectoris, myocardial infarction, ulcers, asthma, allergies, benign prostatic hypertrophy, and psychotic and neurological disorders, including anxiety, schizophrenia, manic depression, delirium, dementia, severe mental retardation and dyskinesias, such as Huntington's disease or Gilles de la Tourette syndrome and/or other pathologies and disorders.

The novel nucleic acid encoding GPCR-like protein, and the GPCR-like protein of the invention, or fragments thereof, are also in diagnostic applications, wher the presence or amount of the nucleic acid or the protein are to be assessed. These materials are further useful in the generation of antibodies that bind immunospecifically to the novel substances of the invention for use in therapeutic or diagnostic methods.

These uses, as well as other utilities for a TSC7 nucleic acid or polypeptide according to the invention, are described below.

TSC24

A TSC24 nucleic acid molecule according to the invention includes a nucleic acid molecule comprising SEQ ID NO:3 or SEQ ID NO:4. SEQ ID NO:4 is a novel 3579 bp gene fragment having 50% similarity to C. elegans procollagen alpha chain 1(V) [Q20220]. The nucleic acid was initially identified in a cloned fragment having the following sequence:

```
  1 caattgacct cctacaggaa gtttggcttt gagattattg agacaaagaa gaactactat
 61 aagaggatag agcccgcaga tgctcatgtg ctgcagaaaa acctcaaagt tccttctggt
121 cagaatgcag atgtgcaaaa gacagacaac tgaacaaatt acaaatgaac tttcttgcac
181 ttgcttgtcg ccaaataaaa gagaggccca ttgattcctc (SEQ ID NO: 3).
```

The sequence was assembled to generate the following 10 sequence

```
   1 TTTTTTTTTTTTTTTTTTTTTTTTACCAGAACATCACATAAGTTTATTTCAGATGTAACAGCAATGTTAAAATTGACAAG
  81 TTTAATTCTTAACTGCACCAAGTAAACTTAGCCATTTAAGTATTTTTTAAGTTATTCCCTCCAAAAAACTGAGGGAGCT
 161 TTTCTTTTCCACCACCACACCATGGTTTCCCAATAGTTCTCTTTTTGGAGGACTTTTCAATTGATGAGTAAACTGCTTTA
 241 GATATTTCAGAACTTCATTCCCCAAATGAAAGCTAATCTGGACAAACTATATATTGCATAGATTTCTCTACAGATTCTTT
 321 GCTTTAAAACCTAAATGCAACTAACATAGTGTAATTTTAACCTATTTGCCCCACAGTAAAAACTATCTGTCCTGAAAAAT
 401 ATGATGGATATATCCTGTGATTTTCCAGTTAACAGAATTCTTCTACTTCAAAGATAATTATTATCATATATCAAAATAAC
 481 CAGCTCAACATAGGACATTACTTCAGTCTTTACTGACTCATAGGCATATGAAACTTGGTGCCCCAGCTTTTTACCTCTTC
 561 CACATTCTCCTCCTCCTCCATAAGTGGATGGAATTATTTAACTAAGTTTGATGTAGGACAATTAACCCTTTACAAACATT
 641 TACAATTCAGGTTAAGTCACTGACTACCGTGGAAAAAGAAACTCTATATATAATGATAGGGAGCCTACACACTCAATTCA
 721 AAATTTAATATTTTTTCCTCCTTAAATAACATGTACTTGTCATGAGGCAGCTATTAGGTTTTCAATAACCACATTTAGGG
 801 ATACATTCATAGGACTGATTAGATAGTCCAGGTGAAATGGTTATAGAAATAGAGGCAGTGTCATCTCAGAAAACCATTTA
 881 TATATCAAAGTCTATTTTGATATCTGGGAAGTTTACAAAAAGGCTGCTGCATTCTTCAAACTACTTATGCCTTCTGTAAC
 961 TCAAGCACTCTTCTCTTGCCAAGAGCAAGCTGAAGCTTATTCATGAAGATAAAGGTGCTTAACGCTAAACTTTTCTTCTA
1041 AGCTTAGATTTGGATTGTTTAAGAAACGAATACCCCCAAAAAACCAGCAAGGTCTTTCTACATTTTTACCATCTTAAGAT
1121 TAGAACCCTATAAACTCATTCATCAACTGTCTTCTTTTTCTGTATTATTCTTGGCACTCAAGATTGTTGAAGTCTACTGC
1201 ACTTTGTACTTTCACATTCTCAAATAAAAACTTAAGGTTATAAAGTGTGCATAAACATTTTATAAAATAATTTTGTCATT
1281 TAACATATTTGGAAATGAGACTTTATACCGCAATTTTACATAAGAGGATAAATATGAATGAAACTTCCTTTTAAAGTCAA
1361 ATGACAGAAAGCTCAAGCCCTGTGCATTATTTTAAAGTCTGAGAACATTTCTAAATAGTGGAGATGGGACTACAAAAGGA
1441 AAACATGAATATTTCAGATGTCTCCCATCTTACAAAGTTATCAATCTGTCAAAGCCCTCCGTGTGTGCCGGAAAATGATC
1521 TGGCATAAACCAGTCCTCTCAGTGGAGGAGGTCACAGTGACATTTGTATTATTAACATTTTACACTTCTATTTTTCCAAG
1601 AATAGAAGCAATATGTTTAATAATTACCCCTGCCTCAAATCCTTAAACTCAATATCACAGGCACTGAGTATAAGCAAATC
1681 TGGGATGTCCTCCAACAGATGTGCAATAGCACAGCTATGTTATTCTCAAAAATACTATTTTTTCCTATAAAATCAAATGC
1761 TCAGTGGCCACACTTTTAACAGCTGGCATTAGATGACAGTAATTGAATTTTTTGTGTCACAGCCCATCTAAGCTTCCTTT
1841 TAGGTATTTTTTAGTATGTCCAAGAGAAAACACCTGCTTCAGGTTTATTTAGGGGTAGTGACCTATAAGGACATCAACTC
1921 AATTTTTAAGGTTAGACTATTGTTGGGTTTACTGAAGAAAAAGGAACGGGAAAAAATTAAATCACAACACACCTCTTTAG
2001 GTCAGTTAAAGGCCATATCTCTAGCTGGGATATTAAAAAAAATTAATCTCACCAGCCCAAATTCTAAAAGTTAATGCCAC
2081 TAGTAACAATCAACAGCAGGAAAAACAAACCTGCTAACAACCAGCCCACTCATTAGCAAAAAAGCAGTTTAACTCAAATA
2161 CTTAGACCAAAGTATAACACTAAACCAAACTGCCCCACCCACCAGCAAGAAGAGAAGATATAATTACTTAAAAATCAACA
2241 TAAGCTTAGTATTTCTTACAAGGATAACAATGTTCCAACTCCCGAGAGAGTGCTCAGAAGGACTAAAGGTGGAGTGAAGG
2321 CAATGTCTAGGGATTAGTATCCCAAAGTGTTTAAAAACCCAAAGTACCACAAACACACTCAACTTGTCTATGAATTAGAG
2481 AACAAGATACTGCTGCTGCTTCTTTTTGTCTTTTGAAATATACAATGTTTTGTAGGCTCTGCCCTTCAATGTGAAAGCAG
2401 GACATTAAATTTGAAATTATTTGACAATTAAATGTTTAGGACCATCTAACTTCAACTGCAAAACTAAACAGATCTACCTT
2561 GTCCTTCCTTCAAACCACCTCACAAAAATAAGAGAAAACAATTCAAACATGATTATTTTTTAAAGTCCTTGAAAGTATT
```

-continued

```
2641 AAAACTCTCAGAGAAAAGGAAAGGAAGAAAGAAAAACAAGAACAAGGAGGGAGAAAAGCTTTAAAAGAAAAGTGTTGGGG

2721 TGGGGGAGGAATCAATGGGCCTCTCTTTTATTTGGCGACAAGCAAGTGCAAGAAAGTTCATTTGTAATTTGTTCAGTTGT

2801 CTGTCTTTTGCACATCTGCATTCTGACCAGAAGGAACTTTGAGGTTTTTCTGCAGCACATGAGCATCTGCGGGCTCTATC

2881 CTCTTATAGTAGTTCTTCTTTGTCTCAATAATCTCAAAGCCAAACTTCCTGTAGAAGTCAATTGCCGACTCATTGCTGAT

2961 CTGGACATGCAGATAAATGTTGTCAAAAGTACCATCTTTTCACAGATGTTTAAGAACATGATTTAACATTTTAGTTCCTA

3041 TTCCTAGCCTTCGGTAAGGTGCCAGACATCCTAGTGTCATGATGTAAAGTCTCTTCTGATTCTGTGAATGATCCACCCTA

3121 CAGCATACTGCACCTACAGCAATATCATTGAAATAGGCAAGTTTTGCTAGCTCGCCAACCTCCAGCACATCCTTGTAGAA

3201 CTTGTCATTGTAGCTGACTGGAAAGATGACCTGATTCAATCTTTTCAACTGTTTAATATTGTGTGGTGTCACATCTCCCA

3281 GCTCGATCCGGCCTTTCATCTTCCCCGCCTGCTGAGGCCGTCGTTACCACCGATATCAACGCCGTCGTAGTCGCCGCCCT

3361 TGGGTCTCCGCACCCTTAGCTCGGGCCACTCAACCCCGCAAGCCGGCCTCCTAGCCTGGGCAGGGAGCTGTGCGAGCAAC

3441 GAAGGCCGCGAGAGTCGAGTGAGGGCTTGAGTCTGGTGGGAGCGGGAGTGTCTCCCGCCGCCGCGCTTGTGCCGCCGCTT

3521 CTCCACACGTGCACTCGGGTCTCTCGGCTCCCTCCCGCCGTGCCGCCAGCCAGACCCGC (SEQ ID NO: 4).
```

The sequence of SEQ ID NO:4 was assembled from the ests shown in Table 3:

TABLE 3

| | | | | |
|---|---|---|---|---|
| est:gb__AA910300+ | Est:gb__N20593+ | Est:gb__H91558− | est:gb__N56247− | est:gb__W01763− |
| Est:gb__AI541014− | Est:gb__N44858− | Est:gb__AA343519− | est:gb__AA972730+ | est:gb__AA658152− |
| est:gb__AA810984− | Est:gb__AA854754+ | Est:gb__AI671930+ | est:gb__AA446783− | est:gb__AI262664+ |
| est:gb__T35887− | Est:gb__AI436287+ | Est:gb__AI826834+ | est:gb__N63013+ | est:gb__AI809379+ |
| est:gb__AI569529+ | Est:gb__R70933+ | Est:gb__AA218731+ | est:gb__T32545− | est:gb__AA804481+ |
| est:gb__R55349+ | Est:gb__N44859− | Est:gb__AI435333+ | est:gb__C01604− | est:gb__C75100− |
| est:gb__AI625253+ | Est:gb__AI342257+ | Est:gb__AI251844+ | est:gb__AA528659+ | est:gb__AI347932+ |
| est:gb__AI696521+ | Est:gb__N33401+ | Est:gb__AA827879+ | est:gb__N46440+ | est:gb__H90637+ |
| est:gb__AA640321+ | Est:gb__AI005090+ | Est:gb__N48941− | est:gb__AA913039+ | est:gb__W15356+ |
| est:gb__AA708036− | Est:gb__AA356237+ | Est:gb__AA809236− | est:gb__AI611744+ | est:gb__AI926612+ |
| est:gb__R68785+ | Est:gb__AA337687− | Est:gb__AA974926− | est:gb__AI653586+ | est:gb__AI656178+ |
| est:gb__AI298699− | Est:gb__AA400556− | Est:gb__N55658− | est:gb__AA406629+ | est:gb__W39315− |
| est:gb__AA843265+ | Est:gb__AI093361+ | Est:gb__AA382449+ | est:gb__AA262578− | est:gb__W76428+ |
| est:gb__AI373434+ | Est:gb__R68883− | Est:gb__AI671941+ | est:gb__AA169499+ | est:gb__AI457729+ |
| est:gb__W45020− | Est:gb__AA160707− | Est:gb__AA382450− | est:gb__AA432097+ | est:gb__W93520− |
| est:gb__AA806444+ | Est:gb__AA347814+ | Est:gb__N39629− | est:gb__AA300886− | est:gb__Z44216− |
| est:gb__AI590142+ | Est:gb__Z24913− | Est:gb__R70499+ | est:gb__R70588− | est:gb__H12171− |
| est:gb__AI809739+ | Est:gb__AI741781+ | Est:gb__H11644+ | est:gb__AI683096+ | est:gb__AI804775+ |
| est:gb__AI867903+ | Est:gb__AI675853+ | Est:gb__AA354054− | est:gb__AA631284+ | est:gb__AA411719− |
| est:gb__AA725049+ | Est:gb__N56567− | Est:gb__AA347815− | est:gb__R70985− | est:gb__AA523489− |
| est:gb__AA307786− | Est:gb__AI473850+ | Est:gb__AI927045+ | est:gb__AI811945+ | est:gb__AI918660+ |
| est:gb__AI479155+ | Est:gb__Z19793− | Est:gb__AA400252+ | est:gb__AA159500+ | est:gb__W72035− |
| est:gb__AA918621+ | Est:gb__AI554302+ | Est:gb__M85991− | est:gb__AA855166− | est:gb__AA644591− |
| est:gb__AL046801− | Est:gb__R55588− | Est:gb__AA296518− | est:gb__D57020− | est:gb__AI435637+ |
| est:gb__AI610598+ | Est:gb__AI634596+ | Est:gb__H98004+ | est:gb__H26346− | est:gb__AI799952+ |
| est:gb__AA091244− | Est:gb__AA315533− | Est:gb__AA343518+ | est:gb__AA370563− | est:gb__AA218608− |
| est:gb__AI168500+ | Est:gb__AA528722− | Est:gb__AI161334− | est:gb__AA732648+ | est:gb__T35846− |
| est:gb__AA748425+ | Est:gb__AA296519+ | Est:gb__AL046802− | est:gb__N28988− | est:gb__AI880253+ |

TSC25

A TSC25 nucleic acid molecule according to the invention includes a nucleic acid molecule comprising SEQ ID NO:5 or SEQ ID NO:6, which are provided below. SEQ ID NO: 6 is a 647 bp gene fragment having 48% similarity to human emilin precursor [AF088916]. The nucleic acid of SEQ ID NO:6 was initially identified in a cloned fragment having the following sequence:

```
  1 tgatcacggc caccctcacc cccgagagag acgcctacgt ggaag-
    cagtg ctgtcggtct 61 ccaacgccag cgtggcccag ctgcataccg ctgggtacag
    gagagagttc ctggaatacc 121 accgccctcc aggagctttg catacctgcg gggcccggg ggcat-
    tccac ctcatcgtgc 181 ac (SEQ ID NO:5).
```

The cloned sequence was assembled to construct SEQ ID NO:6:

```
  1 CCCGAAGTCACCTCCTGTAGCTTCCCCAGGAGCTCCGGTGCCTTCTCTGGTGTCTTTTTCTGCGGGGCTCACCCAGAAGC

81 CTTTCCCCAGTGATGGGGGCGTTGTCCTCTTTAACAAAGTCTGGTGAACGACGGGGATGTTTACAACCCCAGCACCGGG

161 GTCTTCACGGCTCCTTATGATGGGCGCTACCTGATCACGGCCACCCTCACCCCCGAGAGAGACGCCTACGTGGAAGCAGT

241 GCTGGCGGTCTCCAACGCCAGCGTGGCCCAGCTGCATACCGCTGGGTACAGGAGAGAGTTCCTGGAATACCACCGCCCTC

321 CAGGAGCTTTGCATACCTGCGGGGGCCCGGGGGCATTCCACCTCATCGTGCACCTGAAGGCGGGAGATGCAGTCAACGTC

401 GTGGTGACTGGGGGCAAGCTGGCTCACACAGACTTTGATGAAATGTACTCCACATTTAGTGGGGTTTTCTTATATCCTTT

481 CCTTTCCCACCTCTAAGGTGGCTGGGGAGATGTCAGGGGAAAGATAGATAGTTGTAAAAACTCTAAAGCTTTAATATATT

561 CGGTTTGTATGTAATGGAAGCACGGGGCTAGAGTTTCCACATAGGCCCCAACATAAAGGCCTTCCCTCGCTGTTGAGGCC

641 ACCATGC (SEQ ID NO:6).
```

This gene was downregulated four fold in ashleaf spot and subungual fibroma tissues.

TSC26

A TSC26 nucleic acid molecule according to the invention includes a nucleic acid molecule comprising the nucleotide sequence of SEQ ID NO:7 or SEQ ID NO:8. SEQ ID NO: 8 is a 683 bp gene fragment having 40% similarity to mouse tubulo-interstitial nephritis antigen [AF153366].

SEQ ID NO:8 was determined from a cloned fragment having the following sequence:

```
  1 gctagcaccg ggtctgcacc tgcggggcat ccgggacgcg ggaggccggt actgccagga 61 gcaggacctg tgctgccgcg gccgtgccac gactgtgccc tgccctacct gggcgccatc 121 tgttactgtg acctcttctg caaccgcacg gtctccgact gctgccctga cttctgggac 181 ttctgcctcg gcgtgccacc ccctttttccc ccgatccaag gatgtatgca tggaggtcnt 241 atctatccag tcttgggaac gtactgggac aactgtaacc gtnaccccctg ccaggagaac 301 aggcagtggc agtgtgacca agaaccatgc ctggtggatc cagacatgat ca (SEQ ID
    NO: 7).
```

The cloned sequence was assembled into a contig that includes the EST s3aq:20477389 to form SEQ ID NO:8:

This gene is downregulated eight-fold in subungual fibroma tissue.

TSC33

A T5C33 nucleic acid molecule according to the invention includes a 187 bp gene fragment (SEQ ID NO:9, shown below) having 74% similarity to human lysly oxidase-related protein (WS9–14) [U89942], and a nucleic acid molecule including SEQ ID NO:10, also presented below.

The nucleic acid was initially identified in a cloned fragment having the following sequence:

```
  1 CGTCGAATATCCATGCAGCCGCGTCCATCAGCTACTACGGCTTCGGCAGCACGGTGGCCTACTACTACTACCTGTTGCCA

81 GGCCTCAGCTTGCTGGATGCCAGAGTCATGACTCCATACTTGCAGCAGCGCCTGGGCTGGCACGTGGACTGCACGCGCCT

161 TATCGCCGCCTACCGCGCCCTGGTGCTGCCTGTGGCCTTCGTGCTGGCGGTGGCTTGCACTGTGGCCTGCTGCAAGAGCC

241 GTACCGACTGGTGTACCTACCCGTTCGCGCTGCGCACCTTCGTCTTCGTCATGCCGCTCAGCATGGCCTGCCCCATTATG

321 CTCTGAGCATGTCTGGATCTTCGACCAGGCATGGGGAGAACCCGGTCACACTGCCACTGCCTGTTCTCCTGGCAGGGGCA

401 ACGGTTACAGTTGTCCCAGTACGTTCCCAAGACTGGATAGATACGACCTCCATGCATACATCCTTGGATCGGGGGAAAAG

481 GGGGTGGCACGCCGAGGCAGAAGTCCCAGAAGTCAGGGCAGCAGTCGGAGACCGTGCGGTTGCAGAAGAGGTCACAGTAA

561 CAGATGGCGCCCAGGTAGGGCAGGGCACAGTCGTCGGCACGGCCGCGGCAGCACAGGTCCTGCTCCTGGCAGTACCGGCC

641 TCCCGCGTCCCGGATGCCCCGCAGGTGCAGACCCGGTGCTAGC (SEQ ID NO: 8).
```

```
  1 cccggcatga cattgattgc cagtgggtgg atatcacaga tgtgggcccc gggaattata 61 tcttccaggt gattgtcaac ccccactatg aagtggcaga gtnngatttc tccaacaata 121 tgctgcagtg ccgctgcaag tatgatgggc accgggtctg gctgcacaac tgccacacag 181 gcaattc (SEQ ID NO: 9).
```

The cloned sequence was assembled into a contig that includes the EST s3aq:13000354. The resulting consensus sequence is:

```
  1 ACGCGTGAAGGGCATGGCTCCAATAAGCTGAGGTATCTGGTGTATCGGCAGCAGCTAGGAGTGTGCAGTGACAGCTTCAG

81 ATGAGGTTGTTCCTGAGACGCTGTTCCTGCTCCAGGGAGAGTTCTGCATTGGCTGGGTATGAATTCCCTGTGTGGCAGTT

161 GTGCAGCCAGACCCGGTGCCCATCATACTTGCAGCGGCACTGCAGCATATTGTTGGAGAAATCTGACTCTGCCACTTCAT

241 AGTGGGGGTTCACAATCACCTGGAAGATATAATTCCCGGGGCCCACATCTGTGATATCCACCCACTGGCAATCAATGTCA

321 TGCCGGC (SEQ ID NO: 10).
```

TSC37

A TSC37 nucleic acid molecule according to the invention includes a nucleic acid molecules comprising the sequence of SEQ ID NO:11 or SEQ ID NO:12, whose sequences are provided below.

A TSC37 nucleic acid was initially identified in a cloned fragment having the following sequence:

```
  1 ccatggcagg cagtgaaaag agccaggagt cctgggttct agtccctgct ctgcccccaa 43

81 ctggctgtat aacctttgaa aaatcattt ctttgtctga gtctctggtt ctccgtcagc 121 aacaggctgg tataaggtcc cctgcaggtt ccttctagct ggagcactca cagcttccct 181 gactgccag (SEQ ID NO: 11).
```

The cloned sequence was assembled into a contig (SEQ ID NO:12) that includes the following ESTs: est:gb__AI783480−; est:gb__AI278088+; est:gb__AI274095+; est:gb__AI423919+.

The resulting consensus sequence is:

This gene was downregulated 13-fold in ashleaf spot, while it was upregulated two-fold in subungual fibroma.

TSC38

A TSC38 nucleic acid molecule according to the invention includes a nucleic acid molecule comprising the nucleotide sequence of SEQ ID NO:13 or 14, whose sequences are provided below. A TSC38 nucleic acid molecule was initially identified as a 404 bp gene fragment having the sequence of SEQ ID NO:13:

```
  1 TTTTTTGTTGGTTATCCACGAGGGTTTATTTCCACTTGAGACCCCTGATGGGAGCAACAATGCAGAGGCCCTTTACAGAA

81 TGGTGAAGCATATGATATAAAAGATACAAAATATAACATCATTTACATGTGCCATTCATAGACAAAGGAGTGTGTTTGAT

161 GAGCCGGTTGGAGAAAGTGGACACTTCCCAATCATTCCCTCTCAGGGGCTTCTCTGGCTGCCTTGCTCTGATGGAGATTT

241 TCAGGAGAGAGAGCTCCAGGGAGAAGGAGAACAATCAGCCCTGTGAGGGCCAGAGAGGCTGCTAGCAGTCAGGGAAGCTC

321 TGAGTGCTCCAGCTAGAAGGAACCTGCAGGGGACCTTATGCCAGCCTGTTGCTGACGGAGAACCAGAGACTCAGACAAAG

401 AAAATGATTTTTCAAAGGTTATACAGCCAGTTGGGGGCAGAGCAGGGACTAGAACCCAGGACTCCTGGCTCTTTTCACTG

481 CCTGCCATGG (SEQ ID NO: 12).
```

```
  1 aagctttaca agtatttatt ttataaggct tagacagaat tattggagtt ttaaattaag 61 tgtattggaa aagaaaggat ggtatgtgta tgaaatgtta agatcctacg caacactnct 121 attttttcc tttaatattt gtgctgcata acaaaagcca ctagactgtt actgtcttgt 181 ctgtccatgt gttaacagca tttcttaatg atgtatatat ggagtggtct tctatcatag 241 tgaagaattt aaagagaaag tcaattg (SEQ ID NO: 13).
```

The cloned sequence was assembled into a contig that includes the sequence of SEQ ID NO: 14:

```
  1 AAGCTTTACAAGTATTTATTTTATAAGGCTTAGACAGAATTATTGGAGTTTTAAATTAAGTGTATTGGAAAAGAAAGGAT

81 GGTATGTGTATGAAATGTTAAGATCCTACGCAACACTGCTATTTTTTTCCTTTAATATTTGTGCTGCATAACAAAAGCCA

161 CTAGACTGTTACTGTCTTGTCTGTCCATGTGTTAACAGCATTTCTTAATGATGTATATATGGAGTGGTCTTCAATCATAG

241 TGAAGAATTTAAAGAGAAAGTCAATTGTATTGGCATTTTTAATAAGGAACAAAATTAGTTCGTCTAAGGGGACTGGCTGG

321 CCACATATTTGTTCCTTGCCCATATGCTTTCTACTTCTTGTTCTTATTATGGAAATTATGGATTTTGGAAGGCCTCTGGA

401 ATGG (SEQ ID NO: 14).
```

The sequence in SEQ ID NO:14 includes est:gb_T82365+ and est:gb_AA376667

A TSC38 nucleic acid molecule according to the invention is downregulated five-fold in shagreen patch and upregulated three-fold in ashleaf spot.

TSC39

A TSC39 nucleic acid molecule according to the invention includes a nucleic acid molecule comprising SEQ ID NO:15 or SEQ ID NO:16, whose sequences are provided below.

A TSC39 nucleic acid molecule according to the invention was first identfied as a 1547 bp gene fragment with the following sequence:

```
  1 gtggcacgtgctcgtaatcccagctactcgggaggctgaggcaggagaatcaattgaacctgggaggcagaggttgcagt 81 gagccgagatggcgccattgcactccagcctgggtgacaaaagcaaaagtccatcttaagaaatatatatatatattata 161 tatattcttagttctaagatttcctttaattctatgattctctggatttaaatgcattattcatatttcttgaagcttag 241 atacagtctaattcatagcaaccatatctgctttatcctaggtgagggtagcagtccacaatggaatagaagaaaatccc 321 attataacaaatgacaaattanatatcatgaatccttctgtctgactaactcaataactttctataaaagccaatggaat 401 tcaaataggacctaggagacaacaagttatatgacagtggaggttgtattccttttatattgctgagaaaactagtta 481 aatgatc (SEQ ID NO: 15).
```

The cloned sequence was assembled into a contig that includes the ESTs listed in Table 4.

TABLE 4

| | | | | |
|---|---|---|---|---|
| est:gb_AA476558− | est:gb_AI744905+ | est:gb_AI439384+ | Est:gb_AI580794+ | est:gb_AL035977+ |
| est:gb_AI277687+ | est:gb_R36210− | est:gb_R36113+ | Est:gb_W94200+ | est:gb_R35473− |
| est:gb_W94203− | est:gb_AA423905− | est:gb_AI752121+ | Est:gb_AA581508+ | est:gb_R68635+ |
| est:gb_AI290513+ | est:gb_R68634− | est:gb_AA423884+ | Est:gb_AA449680+ | est:gb_AI494006+ |
| est:gb_AI082670+ | est:gb_AI149036+ | est:gb_C00148− | Est:gb_AI333438+ | est:gb_AI066670+ |
| est:gb_AI160784+ | | | | |

The resulting consensus sequence is:

```
   1 TTTTTTTTTTTTTTTTTTAACCAGAACAAAAGACATTTTATTTTGAGAAATAAATTGGAAAAAAATATTTTAAAATGTT

81 TAATTTGCAATATACATAATACTGGAATTGAAATGCTGTCTGATGGAAATGTTGCAATGTGGAGTAGGAGGGTCAAGTTC

161 GTGAAGATATTCTTAAAATTAATCTTGGAAACTCTGTGCCTATGAGGTTTCTCTAAAGTGGCTAAAATATGCATTTAATA

241 TGTTGTCTAAATGAGTACATTTAATTCTAGAGACTGTAAGGAGTAGAGATTATATGCTTTGGGGCTTTTTGTAGCATTTT

321 TTTAAAATCAGTTGTACAGATCCCATTAAACGAAATTGTTTCTTAACAGCAAGAATCTGATCATTTAACTAGTTTTCTCA

401 GCAATATAAAAGGAATACAACCTCCACTGTCATATATAACTTGTTGTCTCCTAGCTCCTATTTGAATTCCATTGGCTTTT

481 ATAGAAAGTTATTGAGTTAGTCAGACAGAAGGATTCATGATATATAATTTGTCATTTGTTATAATGGGATTTTCTTCTAT

561 TCCATTGTGGACTGCTACCCTCACCTAGGATAAAGCAGATATGGTTGCTATGAATTAGACTGTATCTAAGCTTCAAGAAA

641 TATGAATAATGCATTTAAATCCAGAGAATCATAGAATTAAAGGAAATCTTAGAACTAAGAATATATATAATATATATATA

721 TATTTCTTAAGATGGACTTTTGCTTTTGTCACCCAGGCTGGAGTGCAATGGCGCCATCTCGGCTCACTGCAACCTCTGCC

801 TCCCGTGTTCAAGCGATTCTCCTGCCTCAGCCTCCCAAGTAGCTGGGATTACAAGCACGTGCCACCACACCCAGCTAATT

881 TTTGTATTTTTAGTAGAAACAGGGTTTCACCACGTTGGCCAGGCTGGTCTCGAACTCCTGACCTCAGGTTATCTACCCAC

961 CTCAGCCTCCCAAAGTATTGTGATTACAGGTGTGAGCCACCATGTCCAGCCTAGTACCAATCTTTAGACAACAGATGCTT

1041 ATAATCAATATACTGCTTAGTAGTAATTTGGTATTTGAAGTTAATATACTTACTTAACAAAAAAATCCCAGATCAGATGT

1121 TTTAAAGTTTTAAATATAAACTAAATTTTAAACTATAAATACTTACCTTAAAATACTAGAAATCCTAATATCATCAATTC

1201 AGTAAGAGCTCTGGCATAGAAAAATGTAACTACAAATCAAATTATTTTTTAACCAGTGCTGGATCTTCATTACAAAATAA

1281 GGGGAAAAAATCCTCTGCTGTCATCAAAAAGTTTTCCAAATTATCTGTAAACACCAAGGAATTCTATTATTCTTTTTCAA

1361 TTCTCTTAATTTCTACATCTTTCTGCCTATAGTGTTTTACTTCCAATATAGCACAAATCCATGCTACATATGTTGATTTC

1441 TGTTGCTTATCTGATTAATTCAAGTAAAAATTCTCAGTACTTACCAAGACACTTTAAATTTCTATTAGATAACCATTAGT

1521 ATACTACTGGTTTCGTAGTTAAAAGTAC (SEQ ID NO: 16).
```

An Alu fragment is present between nucleotides 721 and 1011 of SEQ ID NO:16.

TSC40

A TSC40 nucleic acid molecule according to the invention includes a 192 bp gene fragment having the nucleotide sequence of SEQ ID NO:17:

```
  1 gaattcgtcc ttgaggatca gctaggctgc aaacgtggag tctctcatct gatccagaag 61 gggtagaaga gtctgcacaa gcttctgtgc acctgggaat gtttcgtgcg ttgagaggag 121 aggtggggtc tcagcaggag gaggtcctgc aggtggtgct gcaagggtc ggctggccgc 181 agggaggccg gc (SEQ ID NO: 17).
```

A TSC40 nucleic acid molecule according to the invention is upregulated in two of three lesions: four-fold in ashleaf spot and three-fold in subungual fibroma.

TSC41

A TSC41 nucleic acid molecule according to the invention includes a nucleic acid molecule compising the sequence of SEQ ID NO:18:

```
  1 gtgcacacct cagggttcoa gatccttgat ctcgtgacct ctgacctgca gtgacctcgc
 61 caaccgacgs ggccgccccg ccacgccccc gccccaaggt gcaccgagat ct (SEQ ID NO: 18).
```

Table 1 also reveals that the differentially expressed genes can be grouped according to the function played by their encoded protein, or by the function played a protein having similarity to the encoded protein. For example, many of the genes encode proteins involved in signal transduction or tissue architecture.

Small proteoglycans have been shown to act as receptors for matrix molecules or growth factors and to influence the attachment and migration of cells. Multiple proteoglycans were deregulated in this study. Lumican (TSC20) has been shown to be expressed in breast carcinoma with higher expression associated with higher tumor grade. Leygue et al., Cancer Res. 68: 1348–52 (1998). Subungual fibroma fibroblasts showed a 20-fold up regulation in this gene. Decorin (TSC17), known to suppress the growth of various tumor cell lines, has been shown to be up regulated in tissue surrounding tumors. Hunzelmann et al., J. Invest. Dermatol. 104: 509–13 (1995). In the present study, decorin was down regulated in shagreen and ashleaf but up regulated in the subungual fibroma. This may indicate a difference between hamartomatous and nonhamartomatous tissue. A similar but lessened effect is described with biglycan (TSC16), although with this gene, the subungual fibroma is down regulated and the ashleaf spot is up regulated.

Another component of the ECM are glycoproteins. SPARC (TSC22) is a glycoprotein associated with the ECM thought to be a contributor to the malignant phenotype. Lower levels were found in transformed fibroblasts as compared to normal. Colombo et al., Eur. J. Cancer 27: 58–62 (1991). Down regulation was seen in the shagreen patch and subungual fibroma while the ashleaf spot showed up regulation. Thrombospondin (TSC32) is another glycoprotein that modulates cell proliferation and is a potent inhibitor of angiogenesis. Dameron, et al., Science 265: 1582–84 (1994). In the ashleaf spot this gene is down regulated, possibly allowing angiogenesis to occur. Microfibril associated glycoprotein 2 (TSC21) is a component of elastin-associated microfibrils. This gene appears to be down regulated in the shagreen patch lesion.

Fibrous components of the ECM also showed deregulation. Laminin α3 (TSC19) and 4 (TSC18) were up regulated in the shagreen patch while the ashleaf spot showed mixed results and the subungual fibroma showed down regulation. Collagen type IV (TSC23) was down regulated in the subungual fibroma as well.

Five genes associated with ECM and intercellular adhesion were regulated in this study. The integrin β5 subunit of the integrin receptor (TSC31) and a novel gene similar to the lysyl-oxidase related protein (TSC33) were both regulated in the subungual fibroma only. Thrombospondin (TSC32), fibronectin receptor (TSC30), and osteoblast specific factor-2pl (TSC34) are discussed in other sections.

Breakdown of the ECM is an integral feature of tumor growth as the confines of the cell are deregulated. Two genes responsible for ECM proteolysis were found to have differential regulation in this study. The tissue plasminogen activator (TSC28) is a serine protease with multiple functions to include degradation of ECM proteins and IGFBP-3. Up regulation of this protein (TSC28) and down regulation of its inhibitor (TSC29) would increase matrix breakdown and proteolysis of IGFBP-3 increasing tumorigenicity.

Menouny, et al., Int. J. Cancer 77: 874–79 (1998). See Growth Factor Sensitivity, below. Here, expression levels of both mRNAs are down regulated in the subungual fibroma fibroblasts. A different class of proteases called matrix metalloproteinases was also regulated. Type I interstitial collagenase (TSC27) is the only enzyme capable of initiating the breakdown of collagens. It is considered to have an important role in tissue development and angiogenesis. Kahari and Saarialho-Kere, Exp. Dermatol. 6: 199–213 (1997). This protein is upregulated in both collagenous lesions, the shagreen patch and subungual fibroma. This could be a reaction to the build up of collagen caused by the tumor or a factor in the deregulation of collagen in the ECM.

Cytokeleton Regulation

The cytoskelton is known to be greatly affected by the transformed phenotype of tumors. Two intermediate filaments, two actin filaments, and an actin inhibitor are differentially regulated in TSC fibroblasts. These regulations are most likely not the cause of the problem but a consequence of the transformed state. Cytokeratin-18 (TSC11) and keratin K7 (TSC10) expression was turned off in the subungual fibroma. Cytokeratin-18 was up regulated in the other two lesions. α actin (TSC12) and γ actin (TSC13) were severely down regulated in the subungual fibroma while α actin only was upregulated in the ashleaf spot. Macrophage capping protein (TSC15) is a reversible blocker of actin filaments found in increasing levels from promyelocytes to monocytes to macrophages. This gene was up regulated in shagreen patch and subungual fibroma, but down regulated in the ashleaf spot fibroblasts.

Growth Factor Sensitivity

Growth factors and their binding proteins can be very important in the tumor phenotype of uncontrolled growth. Transforming growth factor β1 binding protein (TSC5) is a component of elastin-associated microfibrils. Its release from the matrix is a plausible extracellular mechanism for the regulation of TGF-β1 activation. Karonen et al. Br. J. Dermatol. 137: 51–58 (1997). TSC5 was up regulated in two of three lesions, shagreen patch and subungual fibroma, and down regulated in the third, ashleaf spot. In addition to TGFBP-1, three other proteins associated with TGF-β1 were regulated in this study. Thrombospondin (TSC32), known to activate TGF-β1 is down regulated in the ashleaf spot. Endoglin (TSC6), a component of the TGF-β type I receptor complex, is up regulated in shagreen and ashleaf spot lesions. This gene has been correlated with angiogenesis and cell-cycle regulation. Bodey et al., Anticancer Res. 18: 1485–00 (1998). Fibronectin receptor (TSC30) has also been shown to be regulated by TGF-β, here the shagreen patch and subungual fibroma showed deregulation.

The insulin-like growth factor binding proteins prolong the half-life of the IGFs and have been shown to inhibit or stimulate the growth promoting effects in cell culture. IGFBP-2 (TSC3) has been shown to be expressed by tumors and correlate with tumorigenicity (Menouny, et al., Int. J. Cancer 77: 874–79 (1998): and Bodey et al., Anticancer Res. 18: 1485–00 (1998)) here, expression was upregulated in subungual fibroma and ashleaf spot. IGFBP-5 (TSC4) is deregulated the present study.

Pre-B-cell stimulating factor homologue (SDF1b) (TSC2) is a cytokine known to produce actin polymerization in lymphocytes and is an efficacious lymphocyte chemoattractant. In the present study this gene was deregulated in all three lesions.

Cancer-Related Genes

Adrenomedullin (TSC1) is an anti-proliferative gene known to be down regulated by the oncogene Myc. This repression is thought to be important in deregulating growth. Wang et al., Mol. Endocrinol. 13: 254–67 (1999). Adrenomedullin was down regulated in all three lesions, thus it may be an important early step in the transformation of TSC tumors.

Nuclear matrix protein 55 (TSC36) is a gene of unknown funcion associated with breast cancer. Loss of expression may be related to hormone insensitivity, tumor differentiation, and unregulated cell growth. Traish et al., Diagn. Mol. Pathol. 6: 209–21 (1997). The shagreen patch showed down regulation of this gene while the other lesions showed up regulation.

Osteoblast-specific factor-2 (TSC34), thought to be involved in tissue growth in bone, and thrombospondin-1 (TSC32) are both implicated as being involved in the genesis of neoplastic phenotype. Genini et al., Int. J. Cancer 66: 571–77 (1996). OSF-2 (TSC34) was up regulated in ashleaf spot and down regulated in the shagreen patch and subungual fibroma. Thrombospondin-1 (TSC32) was down regulated only in the ashleaf spot.

Mac30 (TSC35) is a gene of unknown function that is associated with meningiomas surrounding the brain and spinal cord. This gene was isolated due to its aberrant expression in comparison with normal cells. Murphy et al., Cell. Growth. Differ. 4: 715–22 (1993). This gene showed down regulation in the shagreen patch and especially in the ashleaf spot.

Homeobox Genes

The homeobox genes are transcription factors with essential developmental effects. There is a growing number of reports that there is deregulation of homeobox gene expression in cancer. HOX7 (TSC9) is known to be expressed in heart valves, mandibular and hyeloid arches and limb buds during normal murine development. Loss of the gene in Wolf-Hirschhorn syndrome is characterized by mental retardation, heart defects, and facial clefting. In the present study, a twenty-fold increase in the expression of this gene in the subungual fibroma was observed.

HOXC8 (TSC8) is another developmental transcription factor. It is known to be involved in anterior-posterior axis determination and overexpression causes cartilage defects. Over expression of homeobox genes including HOXC8 has been shown in colorectal cancer. Vider et al., Biochem. Biophys. Res. Commun. 232: 742–48 (1997). De novo expression of this gene has been shown in cervical cancer cells compared to normal keratinocytes. Alami et al., Biochem. Biophys. Res. Commun. 257: 738–45 (1999). HOXC8 expression was deregulated in the subungual fibroma by a twenty-fold decrease.

Alpha B-crystallin (TSC14) has been shown immunohistochemically to be expressed in human hamartomas of TSC patients in various organs. Iwaki and Tateishi, Am J Pathol. 139: 1303–08 (1991). Normally this protein is expressed in the lens of the eye and is induced in other neurological diseases such as Alzheimer's, Huntington's and Parkinson's. A small heat shock protein, it is believed to be involved in intermediate filament turnover, functioning to protect cytoskeleton components from turnover. It may be expressed as a consequence of damage done by the disease. This gene is down regulated in the fibroblasts of the shagreen patch and subungual fibroma. This may be due to inhibition of alpha B-crystallin in the surrounding fibroblasts due to over expression within the tumor itself.

As is described in detail below, TSCX nucleic acids described herein can be used to identify agents associated with conditions indicative of undesired hyperproliferation. These conditions include, e.g., dermatological disorders and neoplasms. Thus, the screening and diagnostic methods described herein can be used to identify neuro-cutaneous disorders, such as neurofibromatosis, Von Hippel-Lindau diseases, and tuberous sclerosis conditions.

Unless indicated otherwise, the term "TSC-X" is intended to include any TSC1–41 nucleic acid or polypeptide according to the invention, e.g., one or more of TSCX7, TSC24–26, 33, 37–41.

TSC-X Nucleic Acids

One aspect of the invention pertains to isolated nucleic acid molecules that encode TSC-X polypeptides or biologically active portions thereof. Also included in the invention are nucleic acid fragments sufficient for use as hybridization probes to identify TSC-X-encoding nucleic acids (e.g., TSC-X mRNA) and fragments for use as PCR primers for the amplification or mutation of TSC-X nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

"Probes" refer to nucleic acid sequences of variable length, preferably between at least about 10 nucleotides (nt), 100 nt, or as many as about, e.g., 6,000 nt, depending on use. Probes are used in the detection of identical, similar, or complementary nucleic acid sequences. Longer length probes are usually obtained from a natural or recombinant source, are highly specific and much slower to hybridize than oligomers. Probes may be single- or double-stranded and designed to have specificity in PCR, membrane-based hybridization technologies, or ELISA-like technologies.

An "isolated" nucleic acid molecule is one that is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated TSC-X nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., lymphocytes, e.g., adrenal gland, brain, breast, epithelial, heart (such as fetal heart), and testis). Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the present invention, e.g., a nucleic acid molecule having the nucleotide sequence of SEQ ID NO:1 or 3–18, or a complement of any of these nucleotide sequences, can be isolated using standard molecular biology techniques and the sequence information provided herein. Using all or a portion of the nucleic acid sequence of SEQ ID NO:1 or 3–18 as a hybridization probe, TSC-X molecules containing longer portions of the disclosed sequences can be isolated using standard hybridization and cloning techniques (e.g., as described in Sambrook et al., (eds.), *Moleculer Cloning: A Laboratory Manual* $2^{nd}$ Ed., Cold Spring Harbor Laboratory Press, Cold Spring Harbor, N.Y., 1989; and Ausubel, et al., (eds.), *Current Protocols in Molecular Biology*, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to TSC-X nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment, an oligonucleotide comprising a nucleic acid molecule less than 100 nt in length would further comprise at lease 6 contiguous nucleotides of SEQ ID NO:1 or 3–18 or a complement thereof. Oligonucleotides may be chemically synthesized and may be used as probes.

In another embodiment, an isolated nucleic acid molecule of the invention comprises a nucleic acid molecule that is a complement of the nucleotide sequence shown in SEQ ID NO:1 or 3–18, or a portion of this nucleotide sequence, e.g., a fragment that can be used as a probe or primer or a fragment encoding a biologically active portion of TSC-X. A nucleic acid molecule that is complementary to the nucleotide sequence shown in SEQ ID NO:1 or 3–18 is one that is sufficiently complementary to the nucleotide sequence shown in SEQ ID NO:1 or 3–18 that it can hydrogen bond with little or no mismatches to the nucleotide sequence shown in SEQ ID NO:1 or 3–18, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof Binding includes ionic, non-ionic, van der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type. Homologs are nucleic acid sequences or amino acid sequences of a particular gene that are derived from different species.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 30%, 50%, 70%, 80%, or 95% identity (with a preferred identity of 80–95%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., *Current Protocols in Moleculer Biology*, John Wiley & Sons, New York, N.Y., 1993, and below.

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of TSC-X polypeptide. Isoforms can be expressed in different tissues of the same organism as a result of, for example, alternative splicing of RNA. Alternatively, isoforms can be encoded by different genes. In the present invention, homologous nucleotide sequences include nucleotide sequences encoding for an TSC-X polypeptide of species other than humans, including, but not limited to, mammals, and thus can include, e.g., mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the nucleotide sequence encoding human TSC-X protein. Homologous nucleic acid sequences include those nucleic acid sequences that encode conservative amino acid substitutions (see below) in SEQ ID NO: 1, 3–18, as well as a polypeptide having TSC-X activity. Biological activities of the TSC-X proteins are described below. A homologous amino acid sequence does not encode the amino acid sequence of a human TSC-X polypeptide.

An TSC-X polypeptide is encoded by the open reading frame ("ORF") of an TSC-X nucleic acid. The invention includes the nucleic acid sequence comprising the stretch of nucleic acid sequences of SEQ ID NOs: 1 or 3–18, that comprises the ORF of that nucleic acid sequence and encodes a polypeptide.

An "open reading frame" ("ORF") corresponds to a nucleotide sequence that could potentially be translated into a polypeptide. A stretch of nucleic acids comprising an ORF is uninterrupted by a stop codon. An ORF that represents the coding sequence for a full protein begins with an ATG "start" codon and terminates with one of the three "stop" codons, namely, TAA, TAG, or TGA. For the purposes of this invention, an ORF may be any part of a coding sequence, with or without a start codon, a stop codon, or both. For an ORF to be considered as a good candidate for coding for a bona fide cellular protein, a minimum size requirement is often set, for example, a stretch of DNA that would encode a protein of 50 amino acids or more.

The nucleotide sequence determined from the cloning of the human TSC-X gene allows for the generation of probes and primers designed for use in identifying and/or cloning TSC-X homologues in other cell types, e.g. from other tissues, as well as TSC-X homologues from other mammals. The probe/primer typically comprises substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence of SEQ ID NO:1 or 3–18, or an anti-sense strand nucleotide sequence of SEQ ID NO:1 or 3–18, or of a naturally occurring mutant of SEQ ID NO:1 or 3–18.

Probes based on the human TSC-X nucleotide sequence can be used to detect transcripts or genomic sequences encoding the same or homologous proteins. In various embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissue which misexpress an TSC-X protein, such as by measuring a level of an TSC-X-encoding nucleic acid in a sample of cells from a subject e.g., detecting TSC-X mRNA levels or determining whether a genomic TSC-X gene has been mutated or deleted.

"A polypeptide having a biologically active portion of TSC-X" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of TSC-X" can be prepared by isolating a portion of SEQ ID NO:1 or 3–18 that encodes a polypeptide having an TSC-X biological activity (the biological activities of the TSC-X proteins are described below), expressing the encoded portion of TSC-X protein (e.g., by recombinant expression in vitro) and assessing the activity of the encoded portion of TSC-X TSC-X variants The invention further encompasses nucleic acid molecules that differ from the nucleotide sequence shown in SEQ ID NO:1 or 3–18 due to degeneracy of the genetic code and thus encode the same TSC-X protein as that encoded by the nucleotide sequence shown in SEQ ID NO:1 or 3–18. In another embodiment, an isolated nucleic acid molecule of the invention has a nucleotide sequence encoding a protein having an amino acid sequence shown in SEQ ID NO:2.

In addition to the human TSC-X nucleotide sequence shown in SEQ ID NO:1 or 3–18, it will be appreciated by those skilled in the art that DNA sequence polymorphisms that lead to changes in the amino acid sequences of TSC-X may exist within a population (e.g., the human population). Such genetic polymorphism in the TSC-X gene may exist among individuals within a population due to natural allelic variation. As used herein, the terms "gene" and "recombinant gene" refer to nucleic acid molecules comprising an open reading frame encoding an TSC-X protein, preferably a mammalian TSC-X protein. Such natural allelic variations can typically result in 1–5% variance in the nucleotide sequence of the TSC-X gene. Any and all such nucleotide variations and resulting amino acid polymorphisms in TSC-X that are the result of natural allelic variation and that do not alter the functional activity of TSC-X are intended to be within the scope of the invention.

Moreover, nucleic acid molecules encoding TSC-X proteins from other species, and thus that have a nucleotide sequence that differs from the human sequence of SEQ ID NO:1 or 3–18 are intended to be within the scope of the invention. Nucleic acid molecules corresponding to natural allelic variants and homologues of the TSC-X cDNAs of the invention can be isolated based on their homology to the human TSC-X nucleic acids disclosed herein using the human cDNAs, or a portion thereof, as a hybridization probe according to standard hybridization techniques under stringent hybridization conditions. For example, a soluble human TSC-X cDNA can be isolated based on its homology to human membrane-bound TSC-X. Likewise, a membrane-bound human TSC-X cDNA can be isolated based on its homology to soluble human TSC-X.

Accordingly, in another embodiment, an isolated nucleic acid molecule of the invention is at least 6 nucleotides in length and hybridizes under stringent conditions to the nucleic acid molecule comprising the nucleotide sequence of SEQ ID NO:1 or 3–18. In another embodiment, the nucleic acid is at least 10, 25, 50, 100, 250, 500, 750, 1000, 1500, or 2000 or more nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding TSC-X proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in Ausubel et al., (eds.), *Current Protocols in Moleculer Biology*, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2×SSC, 0.01% BSA at 50° C. An isolated nucleic acid molecule of the invention that hybridizes under stringent conditions to the sequence of SEQ ID NO:1 or 3–18 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NO:1 or 3–18 or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known in the art. See, e.g., Ausubel et al. (eds.), 1993, *Current Protocols in Molecular Biology*, John Wiley & Sons, NY, and Kriegler, 1990, *Gene Transfer and Expression, A Labrratory Manual*, Stockton Press, NY.

In a third embodiment, a nucleic acid that is hybridizable to the nucleic acid molecule comprising the nucleotide sequence of SEQ ID NO:1 or 3–18 or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, *Current Protocols in Molecular Biology*, John Wiley & Sons, NY, and Kriegier, 1990, *Gene Transfer and Expression, A Laboratory Manual*, Stockton Press, NY; Shilo and Weinberg, 1981, *Proc Natl Acad Sci USA* 78: 6789–6792.

Conservative Mutations

In addition to naturally-occurring allelic variants of a TSC-X sequence that may exist in the population, the skilled artisan will further appreciate that changes can be introduced by mutation into the nucleotide sequence of SEQ ID NO:1 or 3–18, thereby leading to changes in the amino acid sequence of the encoded TSC-X protein, without altering the functional ability of the TSC-X protein. For example, nucleotide substitutions leading to amino acid substitutions at "non-essential" amino acid residues can be made in the sequence of SEQ ID NO:1 or 3–18. A "non-essential" amino acid residue is a residue that can be altered from the wild-type sequence of TSC-X without altering the biological activity, whereas an "essential" amino acid residue is required for biological activity. For example, amino acid residues that are conserved among the TSC-X proteins of the present invention, are predicted to be particularly unamenable to alteration. Amino acids for which conservative substitutions can be made are known in the art.

Another aspect of the invention pertains to nucleic acid molecules encoding TSC-X proteins that contain changes in amino acid residues that are not essential for activity. Such TSC-X proteins differ in amino acid sequence from, e.g., SEQ ID NO:2 yet retain biological activity. In one embodiment, the isolated nucleic acid molecule comprises a nucleotide sequence encoding a protein, wherein the protein comprises an amino acid sequence at least about 45% homologous to the amino acid sequence of SEQ ID NO:2. Preferably, the protein encoded by the nucleic acid molecule is at least about 60% homologous to SEQ ID NO:2, more preferably at least about 70% homologous to SEQ ID NO:2 still more preferably at least about 80% homologous to SEQ ID NO: 2, even more preferably at least about 90% homologous to SEQ ID NO:2, and most preferably at least about 95% homologous to SEQ ID NO:2.

An isolated nucleic acid molecule encoding an TSC-X protein homologous to the protein of SEQ ID NO:2 can be created by introducing one or more nucleotide substitutions, additions or deletions into the nucleotide sequence of SEQ ID NO:2 such that one or more amino acid substitutions, additions or deletions are introduced into the encoded protein.

Mutations can be introduced into SEQ IDs NO:2 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in TSC-X is replaced with another amino acid residue from the same side chain family. Alternatively, in another embodiment, mutations can be introduced randomly along all or part of an TSC-X coding sequence, such as by saturation mutagenesis, and the resultant mutants can be screened for TSC-X biological activity to identify mutants that retain activity. Following mutagenesis of SEQ ID NO:2, the encoded protein can be expressed by any recombinant technology known in the art and the activity of the protein can be determined.

In one embodiment, a mutant TSC-X protein can be assayed for, e.g., (1) the ability to form protein:protein interactions with other TSC-X proteins, other cell-surface proteins, or biologically active portions thereof, (2) complex formation between a mutant TSC-X protein and an TSC-X ligand; (3) the ability of a mutant TSC-X protein to bind to an intracellular target protein or biologically active portion thereof, (e.g. avidin proteins), or (4) the ability to bind a ligand, e.g., a polypeptide ligand.

Antisense

Another aspect of the invention pertains to isolated antisense nucleic acid molecules that are hybridizable to or complementary to the nucleic acid molecule comprising the nucleotide sequence of SEQ ID NO:1 or 3–18, or fragments, analogs or derivatives thereof An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire TSC-X coding strand, or to only a portion thereof Nucleic acid molecules encoding fragments, homologs, derivatives and analogs of an TSC-X protein of SEQ ID NO:2 or antisense nucleic acids complementary to an TSC-X nucleic acid sequence of SEQ ID NO:1 or 3–18, are additionally provided.

In one embodiment, an antisense nucleic acid molecule is antisense to a "coding region" of the coding strand of a nucleotide sequence encoding TSC-X. The term "coding region" refers to the region of the nucleotide sequence comprising codons which are translated into amino acid residues (e.g., the coding region of TSC 1 corresponds to nucleotides 168–1217 of SEQ ID NO: 1). In another embodiment, the antisense nucleic acid molecule is antisense to a "noncoding region" of the coding strand of a nucleotide sequence encoding TSC-X. The term "noncoding region" refers to 5' and 3' sequences which flank the coding region that are not translated into amino acids (i.e., also referred to as 5' and 3' untranslated regions).

Given the coding strand sequences encoding TSC-X disclosed herein, antisense nucleic acids of the invention can be designed according to the rules of Watson and Crick or Hoogsteen base pairing. The antisense nucleic acid molecule can be complementary to the entire coding region of TSC-X mRNA, but more preferably is an oligonucleotide that is antisense to only a portion of the coding or noncoding region of TSC-X mRNA. For example, the antisense oligonucleotide can be complementary to the region surrounding the translation start site of TSC-X mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an TSC-X protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient nucleic acid molecules, vector constructs in which the antisense nucleic acid molecule is placed under the control of a strong pol II or pol III promoter are preferred.

In yet another embodiment, the antisense nucleic acid molecule of the invention is an anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res* 15: 6625–6641). The antisense nucleic acid molecule can also comprise a 2'-o-methylribonucleotide (Inoue et al. (1987) *Nucleic Acids Res* 15: 6131–6148) or a chimeric RNA-DNA analogue (Inoue et al. (1987) *FEBS Lett* 215: 327–330).

Ribozymes and PNA Moieties

Nucleic acid modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

In one embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave TSC-X mRNA transcripts to thereby inhibit translation of TSC-X mRNA. A ribozyme having specificity for an TSC-X-encoding nucleic acid can be designed based upon the nucleotide sequence of an TSC-X cDNA disclosed herein (i.e., SEQ ID NO:1 or 3–18). For example, a derivative of a Tetrahymena L-19 IVS RNA can be constructed in which the nucleotide sequence of the active site is complementary to the nucleotide sequence to be cleaved in an TSC-X-encoding mRNA. See, e.g., Cech et al. U.S. Pat. No. 4,987,071; and Cech et al. U.S. Pat. No. 5,116,742. Alternatively, TSC-X mRNA can be used to select a catalytic RNA having a specific ribonuclease activity from a pool of RNA molecules. See, e.g., Bartel et al., (1993) *Science* 261:1411–1418.

Alternatively, TSC-X gene expression can be inhibited by targeting nucleotide sequences complementary to the regulatory region of the TSC-X (e.g., the TSC-X promoter and/or enhancers) to form triple helical structures that prevent transcription of the TSC-X gene in target cells. See generally, Helene. (1991) *Anticancer Drug Des.* 6: 569–84; Helene. et al. (1992) *Ann. N.Y. Acad. Sci.* 660:27–36; and Maher (1992) *Bioassays* 14: 807–15.

In various embodiments, the nucleic acids of TSC-X can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorg Med Chem* 4: 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) *PNAS* 93: 14670–675.

PNAs of TSC-X can be used in therapeutic and diagnostic applications. For example, PNAs can be used as antisense or antigene agents for sequence-specific modulation of gene expression by, e.g., inducing transcription or translation arrest or inhibiting replication. PNAs of TSC-X can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) above); or as probes or primers for DNA sequence and hybridization (Hyrup et al. (1996), above; Perry-O'Keefe (1996), above).

In another embodiment, PNAs of TSC-X can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of TSC-X can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) *Nucl Acids Res* 24: 3357–63. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA (Mag et al. (1989) *Nucl Acid Res* 17: 5973–88). PNA monomers are then coupled in a stepwise manner to produce a chimeric molecule with a 5' PNA segment and a 3' DNA segment (Finn et al. (1996) above). Alternatively, chimeric molecules can be synthesized with a 5' DNA segment and a 3' PNA segment. See, Petersen et al. (1975) *Bioorg Med Chem Lett* 5: 1119–11124.

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. U.S.A.* 86:6553–6556; Lemaitre et al., 1987, *Proc. Natl. Acad. Sci.* 84:648–652; PCT Publication No. WO88/09810) or the blood-brain barrier (see, e.g., PCT Publication No. WO89/10134). In addition, oligonucleotides can be modified with hybridization triggered cleavage agents (See, e.g., Krol et al., 1988, *BioTechniques* 6:958–976) or intercalating agents. (See, e.g., Zon, 1988, *Pharm. Res.* 5: 539–549). To this end, the oligonucleotide may be conjugated to another molecule, e.g., a peptide, a hybridization triggered cross-linking agent, a transport agent, a hybridization-triggered cleavage agent, etc.

TSC-X Polypeptides

In another aspect, the invention provides TSC-X polypeptides encoded by the TSC-X nucleic acid molecules. The invention also includes a mutant or variant protein any of whose residues may be changed from the corresponding residues while still encoding a protein that maintains its TSC-X activities and physiological functions, or a functional fragment thereof In the mutant or variant protein, up to 20% or more of the residues may be so changed.

In general, an TSC-X variant that preserves TSC-X-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated TSC-X proteins, and biologically active portions thereof, or derivatives, fragments, analogs or homologs thereof Also provided are polypeptide fragments suitable for use as immunogens to raise anti-TSC-X antibodies. In one embodiment, native TSC-X proteins can be isolated from cells or tissue sources by an appropriate purification scheme using standard protein purification techniques. In another embodiment, TSC-X proteins are produced by recombinant DNA techniques. Alternative to recombinant expression, an TSC-X protein or polypeptide can be synthesized chemically using standard peptide synthesis techniques.

An "isolated" or "purified" polypeptide or protein or biologically active portion thereof is substantially free of cellular material or other contaminating proteins from the cell or tissue source from which the TSC-X protein is derived, or substantially free from chemical precursors or other chemicals when chemically synthesized. The language "substantially free of cellular material" includes preparations of TSC-X protein in which the protein is separated from cellular components of the cells from which it is isolated or recombinantly produced. In one embodiment, the language "substantially free of cellular material" includes preparations of TSC-X protein having less than about 30% (by dry weight) of non-TSC-X protein (also referred to herein as a "contaminating protein"), more preferably less than about 20% of non-TSC-X protein, still more preferably less than about 10% of non-TSC-X protein, and most preferably less than about 5% non-TSC-X protein. When the TSC-X protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of TSC-X protein in which the protein is separated from chemical precursors or other chemicals that are involved in the synthesis of the protein. In one embodiment, the language "substantially free of chemical precursors or other chemicals" includes preparations of TSC-X protein having less than about 30% (by dry weight) of chemical precursors or non-TSC-X chemicals, more preferably less than about 20% chemical precursors or non-TSC-X chemicals, still more preferably less than about 10% chemical precursors or non-TSC-X chemicals, and most preferably less than about 5% chemical precursors or non-TSC-X chemicals.

Biologically active portions of an TSC-X protein include peptides comprising amino acid sequences sufficiently homologous to or derived from the amino acid sequence of the TSC-X protein, e.g., the amino acid sequence shown in SEQ ID NO:2, that include fewer amino acids than the full length TSC-X proteins, and exhibit at least one activity of an TSC-X protein. Typically, biologically active portions comprise a domain or motif with at least one activity of the TSC-X protein. A biologically active portion of an TSC-X protein can be a polypeptide which is, for example, 10, 25, 50, 100 or more amino acids in length.

Moreover, other biologically active portions, in which other regions of the protein are deleted, can be prepared by recombinant techniques and evaluated for one or more of the functional activities of a native TSC-X protein.

In an embodiment, the TSC-X protein has an amino acid sequence shown in SEQ ID NO: 2. In other embodiments, the TSC-X protein is substantially homologous to SEQ ID NO:2 and retains the functional activity of the protein of SEQ ID NO:2, yet differs in amino acid sequence due to natural allelic variation or mutagenesis, as described in detail below. Accordingly, in another embodiment, the TSC-X protein is a protein that comprises an amino acid sequence at least about 45% homologous to the amino acid sequence of SEQ ID NO:2 and retains the functional activity of the TSC-X proteins of SEQ ID NO:2.

Determining Homology Between Two or More Sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch 1970 *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in, e.g SEQ ID NO:1, 3, 5, or 7.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides TSC-X chimeric or fusion proteins. As used herein, an TSC-X "chimeric protein" or "fusion protein" comprises an TSC-X polypeptide operatively linked to a non-TSC-X polypeptide. An "TSC-X polypeptide" refers to a polypeptide having an amino acid sequence corresponding to TSC-X, whereas a "non-TSC-X polypeptide" refers to a polypeptide having an amino acid sequence corresponding to a protein that is not substantially homologous to the TSC-X protein, e.g., a protein that is different from the TSC-X protein and that is derived from the same or a different organism. Within an TSC-X fusion protein the TSC-X polypeptide can correspond to all or a portion of an TSC-X protein. In one embodiment, an TSC-X fusion protein comprises at least one biologically active portion of an TSC-X protein. In another embodiment, an TSC-X fusion protein comprises at least two biologically active portions of an TSC-X protein. In yet another embodiment, an TSC-X fusion protein comprises at least three biologically active portions of an TSC-X protein. Within the fusion protein, the term "operatively linked" is intended to indicate that the TSC-X polypeptide and the non-TSC-X polypeptide are fused in-frame to each other. The non-TSC-X polypeptide can be fused to the N-terminus or C-terminus of the TSC-X polypeptide.

In one embodiment, the fusion protein is a GST-TSC-X fusion protein in which the TSC-X sequences are fused to the C-terminus of the GST (i.e., glutathione S-transferase) sequences. Such fusion proteins can facilitate the purification of recombinant TSC-X.

In another embodiment, the fusion protein is an TSC-X protein containing a heterologous signal sequence at its N-terminus.

In yet another embodiment, the fusion protein is an TSC-X-immunoglobulin fusion protein in which the TSC-X sequences are fused to sequences derived from a member of the immunoglobulin protein family. The TSC-X-immunoglobulin fusion proteins of the invention can be incorporated into pharmaceutical compositions and administered to a subject to inhibit an interaction between an TSC-X ligand and an TSC-X protein on the surface of a cell, to thereby suppress TSC-X-mediated signal transduction in vivo. The TSC-X-immunoglobulin fusion proteins can be used to affect the bioavailability of an TSC-X cognate ligand. Inhibition of the TSC-X ligand/TSC-X interaction may be useful therapeutically for both the treatment of proliferative and differentiative disorders, as well as modulating (e.g. promoting or inhibiting) cell survival. Moreover, the TSC-X-immunoglobulin fusion proteins of the invention can be used as immunogens to produce anti-TSC-X antibodies in a subject, to purify TSC-X ligands, and in screening assays to identify molecules that inhibit the interaction of TSC-X with an TSC-X ligand.

An TSC-X chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) *Current Protocols in Molecular Biology*, John Wiley & Sons, 1992). Moreover, many expression vectors are commercially available that already encode a fusion moiety (e.g., a GST polypeptide). An TSC-X-encoding nucleic acid can be cloned into such an expression vector such that the fusion moiety is linked in-frame to the TSC-X protein.

TSC-X Agonists and Antagonists

The present invention also pertains to variants of the TSC-X proteins that function as either TSC-X agonists (mimetics) or as TSC-X antagonists. Variants of the TSC-X protein can be generated by mutagenesis, e.g., discrete point mutation or truncation of the TSC-X protein. An agonist of the TSC-X protein can retain substantially the same, or a subset of, the biological activities of the naturally occurring form of the TSC-X protein. An antagonist of the TSC-X protein can inhibit one or more of the activities of the naturally occurring form of the TSC-X protein by, for example, competitively binding to a downstream or upstream member of a cellular signaling cascade which includes the TSC-X protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the TSC-X proteins.

Variants of the TSC-X protein that function as either TSC-X agonists (mimetics) or as TSC-X antagonists can be identified by screening combinatorial libraries of mutants, e.g., truncation mutants, of the TSC-X protein for TSC-X protein agonist or antagonist activity. In one embodiment, a variegated library of TSC-X variants is generated by combinatorial mutagenesis at the nucleic acid level and is encoded by a variegated gene library. A variegated library of TSC-X variants can be produced by, for example, enzymatically ligating a mixture of synthetic oligonucleotides into gene sequences such that a degenerate set of potential TSC-X sequences is expressible as individual polypeptides, or alternatively, as a set of larger fusion proteins (e.g., for phage display) containing the set of TSC-X sequences therein. There are a variety of methods which can be used to produce libraries of potential TSC-X variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential TSC-X sequences. Methods for synthesizing degenerate oligonucleotides are known in the art (see, e.g., Narang (1983) *Tetrahedron* 39:3; Itakura et al. (1984) *Annu Rev Biochem* 53:323; Itakura et al. (1984) *Science* 198:1056; Ike et al. (1983) *Nucl Acid Res* 11:477.

The TSC polypeptides of the invention can be polymers of L-amino acids, D-amino acids, or a combination of both. Also included in the invention are TSCX polypeptides in which analogs of the peptide ligands described herein are present in non-peptidyl linkages. For example, in various embodiments, the peptide ligands are D retro-inverso peptides. The term "retro-inverso isomer" refers to an isomer of a linear peptide in which the direction of the sequence is reversed and the chirality of each amino acid residue is inverted. See, e.g. Jameson et al., Nature, 368: 744–746 (1994); Brady et al., Nature, 368: 692–693 (1994). The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into an D retro-inverso peptide by synthesizing a reverse of the sequence for the corresponding native L-amino acid sequence.

Polypeptide Libraries

In addition, libraries of fragments of the TSC-X protein coding sequence can be used to generate a variegated population of TSC-X fragments for screening and subsequent selection of variants of an TSC-X protein. In one embodiment, a library of coding sequence fragments can be generated by treating a double stranded PCR fragment of an TSC-X coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the TSC-X protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of TSC-X proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify TSC-X variants (Arkin and Yourvan (1992) *PNAS* 89:7811–7815; Delgrave et al. (1993) *Protein Engineering* 6:327–331).

Anti-TSC-X Antibodies

The invention encompasses antibodies and antibody fragments, such as $F_{ab}$ or $(F_{ab})_2$, that bind immunospecifically to any of the polypeptides of the invention.

An isolated TSC-X protein, or a portion or fragment thereof, can be used as an immunogen to generate antibodies that bind TSC-X using standard techniques for polyclonal and monoclonal antibody preparation. The full-length TSC-X protein can be used or, alternatively, the invention provides antigenic peptide fragments of TSC-X for use as immunogens. The antigenic peptide of TSC-X comprises at least 4 amino acid residues of the amino acid sequence shown in SEQ ID NO:2 and encompasses an epitope of TSC-X such that an antibody raised against the peptide forms a specific immune complex with TSC-X. Preferably, the antigenic peptide comprises at least 6, 8, 10, 15, 20, or 30 amino acid residues. Longer antigenic peptides are sometimes preferable over shorter antigenic peptides, depending on use and according to methods well known to someone skilled in the art.

In certain embodiments of the invention, at least one epitope encompassed by the antigenic peptide is a region of TSC-X that is located on the surface of the protein, e.g. a hydrophilic region. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824–3828; Kyte and Doolittle 1982, *J. Mol. Biol.* 157: 105–142, each incorporated herein by reference in their entirety.

As disclosed herein, TSC-X protein sequence of SEQ ID NO:2 or derivatives, fragments, analogs or homologs thereof, may be utilized as immunogens in the generation of antibodies that immunospecifically-bind these protein components. The term "antibody" as used herein refers to immunoglobulin molecules and immunologically active portions of immunoglobulin molecules, i.e., molecules that contain an antigen binding site that specifically binds (immunoreacts with) an antigen, such as TSC-X. Such antibodies include, but are not limited to, polyclonal, monoclonal, chimeric, single chain, $F_{ab}$ and $F_{(ab')2}$ fragments, and an $F_{ab}$ expression library. In a specific embodiment, antibodies to human TSC-X proteins are disclosed. Various procedures known within the art may be used for the production of polyclonal or monoclonal antibodies to an TSC-X protein sequence of SEQ ID NO:2 or a derivative, fragment, analog or homolog thereof. Some of these proteins are discussed below.

For the production of polyclonal antibodies, various suitable host animals (e.g., rabbit, goat, mouse or other mammal) may be immunized by injection with the native protein, or a synthetic variant thereof, or a derivative of the foregoing. An appropriate immunogenic preparation can contain, for example, recombinantly expressed TSC-X protein or a chemically synthesized TSC-X polypeptide. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as *Bacille Calmette-Guerin* and *Corynebacterium parvum*, or similar immunostimulatory agents. If desired, the antibody molecules directed against TSC-X can be isolated from the mammal (e.g., from the blood) and further purified by well known techniques, such as protein A chromatography to obtain the IgG fraction.

The term "monoclonal antibody" or "monoclonal antibody composition", as used herein, refers to a population of antibody molecules that contain only one species of an antigen binding site capable of immunoreacting with a particular epitope of TSC-X. A monoclonal antibody composition thus typically displays a single binding affinity for a particular TSC-X protein with which it immunoreacts. For preparation of monoclonal antibodies directed towards a particular TSC-X protein, or derivatives, fragments, analogs or homologs thereof, any technique that provides for the production of antibody molecules by continuous cell line culture may be utilized. Such techniques include, but are not limited to, the hybridoma technique (see Kohler & Milstein, 1975 *Nature* 256: 495–497); the trioma technique; the human B-cell hybridoma technique (see Kozbor, et al., 1983 *Immunol Today* 4: 72) and the EBV hybridoma technique to produce human monoclonal antibodies (see Cole, et al., 1985 In: *Monoclonal Antibodies and Cancer Therapy*, Alan R. Liss, Inc., pp. 77–96). Human monoclonal antibodies may be utilized in the practice of the present invention and may be produced by using human hybridomas (see Cote, et al., 1983. *Proc Natl Acad Sci USA* 80: 2026–2030) or by transforming human B-cells with Epstein Barr Virus in vitro (see Cole, et al., 1985 In: *Monoclonal Antibodies and Cancer Therapy*, Alan R. Liss, Inc., pp. 77–96). Each of the above citations is incorporated herein by reference in their entirety.

According to the invention, techniques can be adapted for the production of single-chain antibodies specific to an TSC-X protein (see e.g., U.S. Pat. No. 4,946,778). In addition, methodscan be adapted for the construction of $F_{ab}$ expression libraries (see e.g., Huse, et al., 1989 *Science* 246: 1275–1281) to allow rapid and effective identification of monoclonal $F_{ab}$ fragments with the desired specificity for an TSC-X protein or derivatives, fragments, analogs or homologs thereof Non-human antibodies can be "humanized" by techniques well known in the art. See e.g., U.S. Pat. No. 5,225,539. Antibody fragments that contain the idiotypes to an TSC-X protein may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Additionally, recombinant anti-TSC-X antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in International Application No. PCT/US86/02269; European Patent Application No. 184,187; European Patent Application No. 171,496; European Patent Application No. 173,494; PCT International Publication No. WO 86/01533; U.S. Pat. No. 4,816,567; U.S. Pat. No. 5,225,539; European Patent Application No. 125,023; Better et al. (1988) *Science* 240:1041–1043; Liu et al. (1987) *PNAS* 84:3439–3443; Liu et al. (1987) *J Immunol.* 139:3521–3526; Sun et al. (1987) *PNAS* 84:214–218; Nishimura et al. (1987) *Cancer Res* 47:999–1005; Wood et al. (1985) *Nature* 314:446–449; Shaw et al. (1988) *J Natl Cancer Inst* 80:1553–1559); Morrison (1985) *Science* 229:1202–1207; Oi et al. (1986) *BioTechniques* 4:214; Jones et al. (1986) *Nature* 321:552–525; Verhoeyan et al. (1988) *Science* 239:1534; and Beidler et al. (1988) *J Immunol* 141:4053–4060. Each of the above citations are incorporated herein by reference in their entirety.

In one embodiment, methods for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of an TSC-X protein is facilitated by generation of hybridomas that bind to the fragment of an TSC-X protein possessing such a domain. Thus, antibodies that are specific for a desired domain within an TSC-X protein, or derivatives, fragments, analogs or homologs thereof, are also provided herein.

Anti-TSC-X antibodies may be used in methods known within the art relating to the localization and/or quantitation of an TSC-X protein (e.g., for use in measuring levels of the TSC-X protein within appropriate physiological samples, for use in diagnostic methods, for use in imaging the protein, and the like). In a given embodiment, antibodies for TSC-X proteins, or derivatives, fragments, analogs or homologs thereof, that contain the antibody derived binding domain, are utilized as pharmacologically-active compounds [hereinafter "Therapeutics"].

An anti-TSC-X antibody (e.g., monoclonal antibody) can be used to isolate TSC-X by standard techniques, such as affinity chromatography or immunoprecipitation. An anti-TSC-X antibody can facilitate the purification of natural TSC-X from cells and of recombinantly produced TSC-X expressed in host cells. Moreover, an anti-TSC-X antibody can be used to detect TSC-X protein (e.g., in a cellular lysate or cell supernatant) in order to evaluate the abundance and pattern of expression of the TSC-X protein. Anti-TSC-X antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

TSC-X Recombinant Expression Vectors and Host Cells

Another aspect of the invention pertains to vectors, preferably expression vectors, containing a nucleic acid encoding TSC-X protein, or derivatives, fragments, analogs or homologs thereof As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., TSC-X proteins, mutant forms of TSC-X, fusion proteins, etc.).

The recombinant expression vectors of the invention can be designed for expression of TSC-X in prokaryotic or eukaryotic cells. For example, TSC-X can be expressed in bacterial cells such as *E. coli*, insect cells (using baculovirusiexpression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., *GENE EXPRESSION Technology: Methods in Enzymology* 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, Gottesman, Gene Expression Technology: Methods in Enzymology 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the TSC-X expression vector is a yeast expression vector. Examples of vectors for expression in yeast *S. cerivisae* include pYepSec1 (Baldari, et al., (1987) *EMBO J* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, TSC-X can be expressed in insect cells using baculovirus expression vectors. Baculovirus vectors available for expression of proteins in cultured insect cells (e.g., SF9 cells) include the pAc series (Smith et al. (1983) *Mol Cell Biol* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J* 6: 187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see, e.g., Chapters 16 and 17 of Sambrook et al., *Molecular Cloning: A Laboratory Manual*. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev* 1:268–277), lymphoid-specific promoters (Calame and Eaton (1988) *Adv Immunol* 43:235–275), in particular promoters of T cell receptors (Winoto and Baltimore (1989) *EMBO J* 8:729–733) and immunoglobulins (Banerji et al. (1983) *Cell* 33:729–740; Queen and Baltimore (1983) Cell 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) *Science* 249:374–379) and the α-fetoprotein promoter (Campes and Tilghman (1989) *Genes Dev* 3:537–546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to TSC-X mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., "Antisense RNA as a molecular tool for genetic analysis," Reviews—Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, TSC-X protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual*. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into, the host cells along with the gene of interest. Various selectable markers include those that confer resistance to drugs, such as G418, hygromycin and methotrexate. Nucleic acid encoding a selectable marker can be introduced into a host cell on the same vector as that encoding TSC-X or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) TSC-X protein. Accordingly, the invention further provides methods for producing TSC-X protein using the host cells of the invention. In one embodiment, the method comprises culturing the host cell of invention (into which a recombinant expression vector encoding TSC-X has been introduced) in a suitable medium such that TSC-X protein is produced. In another embodiment, the method further comprises isolating TSC-X from the medium or the host cell.

Transgenic Animals

The host cells of the invention can also be used to produce nonhuman transgenic animals. For example, in one embodiment, a host cell of the invention is a fertilized oocyte or an embryonic stem cell into which TSC-X-coding sequences have been introduced. Such host cells can then be used to create non-human transgenic animals in which exogenous TSC-X sequences have been introduced into their genome or homologous recombinant animals in which endogenous TSC-X sequences have been altered. Such animals are useful for studying the function and/or activity of TSC-X and for identifying and/or evaluating modulators of TSC-X activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous TSC-X gene has been altered by homologous recombination between the endogenous gene and an exogenous DNA molecule introduced into a cell of the animal, e.g., an embryonic cell of the animal, prior to development of the animal.

A transgenic animal of the invention can be created by introducing TSC-X-encoding nucleic acid into the male pronuclei of a fertilized oocyte, e.g., by microinjection, retroviral infection, and allowing the oocyte to develop in a pseudopregnant female foster animal. The TSC-X DNA sequence of SEQ ID NO:1 or 3–18 can be introduced as a transgene into the genome of a non-human animal. Alternatively, a nonhuman homologue of the human TSC-X gene, such as a mouse TSC-X gene, can be isolated based on hybridization to the human TSC-X cDNA (described further above) and used as a transgene. Intronic sequences and polyadenylation signals can also be included in the transgene to increase the efficiency of expression of the transgene. A tissue-specific regulatory sequence(s) can be operably linked to the TSC-X transgene to direct expression of TSC-X protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan 1986, In: *Manipulating the Mouse Embryo*, Cold Spring Harbor Laboratory Press, Cold Spring Harbor, N.Y. Similar methods are used for production of other transgenic animals. A transgenic founder animal can be identified based upon the presence of the TSC-X transgene in its genome and/or expression of TSC-X mRNA in tissues or cells of the animals. A transgenic founder animal can then be used to breed additional animals carrying the transgene. Moreover, transgenic animals carrying a transgene encoding TSC-X can further be bred to other transgenic animals carrying other transgenes.

To create a homologous recombinant animal, a vector is prepared which contains at least a portion of an TSC-X gene into which a deletion, addition or substitution has been introduced to thereby alter, e.g., functionally disrupt, the TSC-X gene. The TSC-X gene can be a human gene (e.g., the cDNA of SEQ ID NO:1 or 3–18), but more preferably, is a non-human homologue of a human TSC-X gene. For example, a mouse homologue of human TSC-X gene of SEQ ID NO:1 or 3–18 can be used to construct a homologous recombination vector suitable for altering an endogenous TSC-X gene in the mouse genome. In one embodiment, the vector is designed such that, upon homologous recombination, the endogenous TSC-X gene is functionally disrupted (i.e., no longer encodes a functional protein; also referred to as a "knock out" vector).

Alternatively, the vector can be designed such that, upon homologous recombination, the endogenous TSC-X gene is mutated or otherwise altered but still encodes functional protein (e.g., the upstream regulatory region can be altered to thereby alter the expression of the endogenous TSC-X protein). In the homologous recombination vector, the altered portion of the TSC-X gene is flanked at its 5' and 3' ends by additional nucleic acid of the TSC-X gene to allow for homologous recombination to occur between the exogenous TSC-X gene carried by the vector and an endogenous TSC-X gene in an embryonic stem cell. The additional flanking TSC-X nucleic acid is of sufficient length for successful homologous recombination with the endogenous gene. Typically, several kilobases of flanking DNA (both at the 5' and 3' ends) are included in the vector. See e.g., Thomas et al. (1987) *Cell* 51:503 for a description of homologous recombination vectors. The vector is introduced into an embryonic stem cell line (e.g., by electroporation) and cells in which the introduced TSC-X gene has homologously recombined with the endogenous TSC-X gene are selected (see e.g., Li et al. (1992) *Cell* 69:915).

The selected cells are then injected into a blastocyst of an animal (e.g., a mouse) to form aggregation chimeras. See e.g., Bradley 1987, In: *Teratocarcinomas and Embryonic Stem Cells: A Practical Approach*, Robertson, ed. IRL, Oxford, pp. 113–152. A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Curr Opin Biotechnol* 2:823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

Pharmaceutical Compositions

The TSC-X nucleic acid molecules, TSC-X proteins, and anti-TSC-X antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an TSC-X protein or anti-TSC-X antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) PNAS 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Uses and Methods of the Invention

The isolated nucleic acid molecules of the invention can be used to express TSC-X protein (e.g., via a recombinant expression vector in a host cell in gene therapy applications), to detect TSC-X mRNA (e.g., in a biological sample) or a genetic lesion in an TSC-X gene, and to modulate TSC-X activity, as described further below. In addition, the TSC-X proteins can be used to screen drugs or compounds that modulate the TSC-X activity or expression as well as to treat disorders characterized by insufficient or excessive production of TSC-X protein or production of TSC-X protein forms that have decreased or aberrant activity compared to TSC-X wild type protein (e.g. proliferative disorders such as cancer and immune disorders, e.g., multiple sclerosis. In addition, the anti-TSC-X antibodies of the invention can be used to detect and isolate TSC-X proteins and modulate TSC-X activity.

This invention further pertains to novel agents identified by the screening assays described herein and uses thereof for treatments as described herein.

Screening Assays

The invention provides a method (also referred to herein as a "screening assay") for identifying modulators, i.e., candidate or test compounds or agents (e.g., peptides, peptidomimetics, small molecules or other drugs) that bind to TSC-X proteins or have a stimulatory or inhibitory effect on, for example, TSC-X expression or TSC-X activity. The invention also includes compounds identified in the screening assays described herein.

In one embodiment, the invention provides assays for screening candidate or test compounds which bind to or modulate the activity of the membrane-bound form of an TSC-X protein or polypeptide or biologically active portion thereof The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des 12:145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic (carbon containing) or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt et al. (1993) Proc Natl Acad Sci U.S.A. 90:6909; Erb et al. (1994) Proc Natl Acad Sci U.S.A. 91:11422; Zuckermann et al. (1994) J Med Chem 37:2678; Cho et al. (1993) Science 261:1303; Carrell et al. (1994) Angew Chem Int Ed Engl 33:2059; Carell et al. (1994) Angew Chem Int Ed Engl 33:2061; and Gallop et al. (1994) J Med Chem 37:1233.

Libraries of compounds may be presented in solution (e.g., Houghten (1992) Biotechniques 13:412–421), or on beads (Lam (1991) Nature 354:82–84), on chips (Fodor (1993) Nature 364:555–556), bacteria (Ladner U.S. Pat. No. 5,223,409), spores (Ladner USP '409), plasmids (Cull et al.

(1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc Natl Acad Sci U.S.A.* 87:6378–6382; Felici (1991) *J Mol Biol* 222:301–310; Ladner above.).

In one embodiment, an assay is a cell-based assay in which a cell which expresses a membrane-bound form of TSC-X protein, or a biologically active portion thereof, on the cell surface is contacted with a test compound and the ability of the test compound to bind to an TSC-X protein determined. The cell, for example, can of mammalian origin or a yeast cell. Determining the ability of the test compound to bind to the TSC-X protein can be accomplished, for example, by coupling the test compound with a radioisotope or enzymatic label such that binding of the test compound to the TSC-X protein or biologically active portion thereof can be determined by detecting the labeled compound in a complex. For example, test compounds can be labeled with. $^{125}I$, $^{35}S$, $^{14}C$, or $^{3}H$, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of TSC-X protein, or a biologically active portion thereof, on the cell surface with a known compound which binds TSC-X to form an assay mixture, contacting the assay mixture with a test compound, and determining the ability of the test compound to interact with an TSC-X protein, wherein determining the ability of the test compound to interact with an TSC-X protein comprises determining the ability of the test compound to preferentially bind to TSC-X or a biologically active portion thereof as compared to the known compound.

In another embodiment, an assay is a cell-based assay comprising contacting a cell expressing a membrane-bound form of TSC-X protein, or a biologically active portion thereof, on the cell surface with a test compound and determining the ability of the test compound to modulate (e.g., stimulate or inhibit) the activity of the TSC-X protein or biologically active portion thereof Determining the ability of the test compound to modulate the activity of TSC-X or a biologically active portion thereof can be accomplished, for example, by determining the ability of the TSC-X protein to bind to or interact with an TSC-X target molecule. As used herein, a "target molecule" is a molecule with which an TSC-X protein binds or interacts in nature, for example, a molecule on the surface of a cell which expresses an TSC-X interacting protein, a molecule on the surface of a second cell, a molecule in the extracellular milieu, a molecule associated with the internal surface of a cell membrane or a cytoplasmic molecule. An TSC-X target molecule can be a non-TSC-X molecule or an TSC-X protein or polypeptide of the present invention. In one embodiment, an TSC-X target molecule is a component of a signal transduction pathway that facilitates transduction of an extracellular signal (e.g. a signal generated by binding of a compound to a membrane-bound TSC-X molecule) through the cell membrane and into the cell. The target, for example, can be a second intercellular protein that has catalytic activity or a protein that facilitates the association of downstream signaling molecules with TSC-X.

Determining the ability of the TSC-X protein to bind to or interact with an TSC-X target molecule can be accomplished by one of the methods described above for determining direct binding. In one embodiment, determining the ability of the TSC-X protein to bind to or interact with an TSC-X target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising an TSC-X-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the present invention is a cell-free assay comprising contacting an TSC-X protein or biologically active portion thereof with a test compound and determining the ability of the test compound to bind to the TSC-X protein or biologically active portion thereof Binding of the test compound to the TSC-X protein can be determined either directly or indirectly as described above. In one embodiment, the assay comprises contacting the TSC-X protein or biologically active portion thereof with a known compound which binds TSC-X to form an assay mixture, contacting the assay mixture with a test compound, and determining the ability of the test compound to interact with an TSC-X protein, wherein determining the ability of the test compound to interact with an TSC-X protein comprises determining the ability of the test compound to preferentially bind to TSC-X or biologically active portion thereof as compared to the known compound.

In another embodiment, an assay is a cell-free assay comprising contacting TSC-X protein or biologically active portion thereof with a test compound and determining the ability of the test compound to modulate (e.g. stimulate or inhibit) the activity of the TSC-X protein or biologically active portion thereof Determining the ability of the test compound to modulate the activity of TSC-X can be accomplished, for example, by determining the ability of the TSC-X protein to bind to an TSC-X target molecule by one of the methods described above for determining direct binding. In an alternative embodiment, determining the ability of the test compound to modulate the activity of TSC-X can be accomplished by determining the ability of the TSC-X protein further modulate an TSC-X target molecule. For example, the catalytic/enzymatic activity of the target molecule on an appropriate substrate can be determined as previously described.

In yet another embodiment, the cell-free assay comprises contacting the TSC-X protein or biologically active portion thereof with a known compound which binds TSC-X to form an assay mixture, contacting the assay mixture with a test compound, and determining the ability of the test compound to interact with an TSC-X protein, wherein determining the ability of the test compound to interact with an TSC-X protein comprises determining the ability of the TSC-X protein to preferentially bind to or modulate the activity of an TSC-X target molecule.

The cell-free assays of the present invention are amenable to use of both the soluble form or the membrane-bound form of TSC-X. In the case of cell-free assays comprising the membrane-bound form of TSC-X, it may be desirable to utilize a solubilizing agent such that the membrane-bound form of TSC-X is maintained in solution. Examples of such solubilizing agents include non-ionic detergents such as n-octylglucoside, n-dodecylglucoside, n-dodecylmaltoside, octanoyl-N-methylglucamide, decanoyl-N- methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl)dimethylamminiol-1-propane sulfonate (CHAPS), or 3-(3-cholamidopropyl)dimethylamminiol-2-hydroxy-1-propane sulfonate (CHAPSO).

In more than one embodiment of the above assay methods of the present invention, it may be desirable to immobilize either TSC-X or its target molecule to facilitate separation of complexed from uncomplexed forms of one or both of the proteins, as well as to accommodate automation of the assay. Binding of a test compound to TSC-X, or interaction of TSC-X with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-TSC-X fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or TSC-X protein, and the mixture is incubated under conditions conducive to complex formation (e.g., at physiological conditions for salt and pH). Following incubation, the beads or. microtiter plate wells are washed to remove any unbound components, the matrix immobilized in the case of beads, complex determined either directly or indirectly, for example, as described above. Alternatively, the complexes can be dissociated from the matrix, and the level of TSC-X binding or activity determined using standard techniques.

Other techniques for immobilizing proteins on matrices can also be used in the screening assays of the invention. For example, either TSC-X or its target molecule can be immobilized utilizing conjugation of biotin and streptavidin. Biotinylated TSC-X or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with TSC-X or target molecules, but which do not interfere with binding of the TSC-X protein to its target molecule, can be derivatized to the wells of the plate, and unbound target or TSC-X trapped in the wells by antibody conjugation. Methods for detecting such complexes, in addition to those described above for the GST-immobilized complexes, include immunodetection of complexes using antibodies reactive with the TSC-X or target molecule, as well as enzyme-linked assays that rely on detecting an enzymatic activity associated with the TSC-X or target molecule.

In another embodiment, modulators of TSC-X expression are identified in a method wherein a cell is contacted with a candidate compound and the expression of TSC-X mRNA or protein in the cell is determined. The level of expression of TSC-X mRNA or protein in the presence of the candidate compound is compared to the level of expression of TSC-X mRNA or protein in the absence of the candidate compound. The candidate compound can then be identified as a modulator of TSC-X expression based on this comparison. For example, when expression of TSC-X mRNA or protein is greater (statistically significantly greater) in the presence of the candidate compound than in its absence, the candidate compound is identified as a stimulator of TSC-X mRNA or protein expression. Alternatively, when expression of TSC-X mRNA or protein is less (statistically significantly less) in the presence of the candidate compound than in its absence, the candidate compound is identified as an inhibitor of TSC-X mRNA or protein expression. The level of TSC-X mRNA or protein expression in the cells can be determined by methods described herein for detecting TSC-X mRNA or protein.

In yet another aspect of the invention, the TSC-X proteins can be used as "bait proteins" in a two-hybrid assay or three hybrid assay (see, e.g., U.S. Pat. No. 5,283,317; Zervos et al. (1993) Cell 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO94/10300), to identify other proteins that bind to or interact with TSC-X ("TSC-X-binding proteins" or "TSC-X-bp") and modulate TSC-X activity. Such TSC-X-binding proteins are also likely to be involved in the propagation of signals by the TSC-X proteins as, for example, upstream or downstream elements of the TSC-X pathway.

The two-hybrid system is based on the modular nature of most transcription factors, which consist of separable DNA-binding and activation domains. Briefly, the assay utilizes two different DNA constructs. In one construct, the gene that codes for TSC-X is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an TSC-X-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with TSC-X.

This invention further pertains to novel agents identified by the above-described screening assays and uses thereof for treatments as described herein.

Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; and (ii) identify an individual from a minute biological sample (tissue typing); and (iii) aid in forensic identification of a biological sample. Some of these applications are described in the subsections below.

Tissue Typing

The TSC-X sequences of the present invention can also be used to identify individuals or tissues from minute biological samples. In this technique, an individual's genomic DNA is digested with one or more restriction enzymes, and probed on a Southern blot to yield unique bands for identification. The sequences of the present invention are useful as additional DNA markers for RFLP ("restriction fragment length polymorphisms," described in U.S. Pat. No. 5,272,057).

Furthermore, the sequences of the present invention can be used to provide an alternative technique that determines the actual base-by-base DNA sequence of selected portions of an individual's genome. Thus, the TSC-X sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The TSC-X sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 or 3–18 can comfortably provide positive individual identification with a panel of perhaps 10 to 1,000 primers that each yield a noncoding amplified sequence of 100 bases. If predicted coding sequences, such as those in SEQ ID NO:9, 10, 11, or 12 are used, a more appropriate number of primers for positive individual identification would be 500–2,000.

Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining TSC-X protein and/or nucleic acid expression as well as TSC-X activity, in the context of a biological sample (e.g., blood, serum, cells, tissue) to thereby determine whether an individual is afflicted with a disease or disorder, or is at risk of developing a disorder, associated with aberrant TSC-X expression or activity. The invention also provides for prognostic (or predictive) assays for determining whether an individual is at risk of developing a disorder associated with TSC-X protein, nucleic acid expression or activity. For example, mutations in an TSC-X gene can be assayed in a biological sample. Such assays can be used for prognostic or predictive purpose to thereby prophylactically treat an individual prior to the onset of a disorder characterized by or associated with TSC-X protein, nucleic acid expression or activity.

Another aspect of the invention provides methods for determining TSC-X protein, nucleic acid expression or TSC-X activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs, compounds) on the expression or activity of TSC-X in clinical trials.

These and other agents are described in further detail in the following sections.

Diagnostic Assays

An exemplary method for detecting the presence or absence of TSC-X in a biological sample involves obtaining a biological sample from a test subject and contacting the biological sample with a compound or an agent capable of detecting TSC-X protein or nucleic acid (e.g., mRNA, genomic DNA) that encodes TSC-X protein such that the presence of TSC-X is detected in the biological sample. An agent for detecting TSC-X mRNA or genomic DNA is a labeled nucleic acid probe capable of hybridizing to TSC-X mRNA or genomic DNA. The nucleic acid probe can be, for example, a full-length TSC-X nucleic acid, such as the nucleic acid of SEQ ID NO: 1 or 3–18, or a portion thereof, such as an oligonucleotide of at least 15, 30, 50, 100, 250 or 500 nucleotides in length and sufficient to specifically hybridize under stringent conditions to TSC-X mRNA or genomic DNA. Other suitable probes for use in the diagnostic assays of the invention are described herein.

An agent for detecting TSC-X protein is an antibody capable of binding to TSC-X protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect TSC-X mRNA, protein, or genomic DNA in a biological sample in vitro as well as in vivo. For example, in vitro techniques for detection of TSC-X mRNA include Northern hybridizations and in situ hybridizations. In vitro techniques for detection of TSC-X protein include enzyme linked immunosorbent assays (ELISAs), Western blots, immunoprecipitations and immunofluorescence. In vitro techniques for detection of TSC-X genomic DNA include Southern hybridizations. Furthermore, in vivo techniques for detection of TSC-X protein include introducing into a subject a labeled anti-TSC-X antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting TSC-X protein, mRNA, or genomic DNA, such that the presence of TSC-X protein, mRNA or genomic DNA is detected in the biological sample, and comparing the presence of TSC-X protein, mRNA or genomic DNA in the control sample with the presence of TSC-X protein, mRNA or genomic DNA in the test sample.

The invention also encompasses kits for detecting the presence of TSC-X in a biological sample. For example, the kit can comprise: a labeled compound or agent capable of detecting TSC-X protein or mRNA in a biological sample; means for determining the amount of TSC-X in the sample; and means for comparing the amount of TSC-X in the sample with a standard. The compound or agent can be packaged in a suitable container. The kit can further comprise instructions for using the kit to detect TSC-X protein or nucleic acid.

Prognostic Assays

The diagnostic methods described herein can furthermore be utilized to identify subjects having or at risk of developing a disease or disorder associated with aberrant TSC-X expression or activity. For example, the assays described herein, such as the preceding diagnostic assays or the following assays, can be utilized to identify a subject having or at risk of developing a disorder associated with TSC-X protein, nucleic acid expression or activity such as cancer, immune system associated (e.g., multiple sclerosis), or fibrotic disorders. Alternatively, the prognostic assays can be utilized to identify a subject having or at risk for developing a disease or disorder. Thus, the present invention provides a method for identifying a disease or disorder associated with aberrant TSC-X expression or activity in which a test sample is obtained from a subject and TSC-X protein or nucleic acid (e.g., mRNA, genomic DNA) is detected, wherein the presence of TSC-X protein or nucleic acid is diagnostic for a subject having or at risk of developing a disease or disorder associated with aberrant TSC-X expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant TSC-X expression or activity. For example, such methods can be used to determine whether a subject can be effectively treated with an agent for a disorder, such as cancer, immune system associated disorders, e.g., multiple sclerosis. Thus, the present invention provides methods for determining whether a subject can be effectively treated with an agent for a disorder associated with aberrant TSC-X expression or activity in which a test sample is obtained and TSC-X protein or nucleic acid is detected (e.g., wherein the presence of TSC-X protein or nucleic acid is diagnostic for a subject that can be administered the agent to treat a disorder associated with aberrant TSC-X expression or activity.)

The methods of the invention can also be used to detect genetic lesions in an TSC-X gene, thereby determining if a subject with the lesioned gene is at risk for a disorder characterized by aberrant cell proliferation and/or differentiation. In various embodiments, the methods include detecting, in a sample of cells from the subject, the presence or absence of a genetic lesion characterized by at least one of an alteration affecting the integrity of a gene encoding an TSC-X-protein, or the mis-expression of the TSC-X gene. For example, such genetic lesions can be detected by ascertaining the existence of at least one of (1) a deletion of one or more nucleotides from an TSC-X gene; (2) an addition of one or more nucleotides to an TSC-X gene; (3) a substitution of one or more nucleotides of an TSC-X gene, (4) a chromosomal rearrangement of an TSC-X gene; (5) an alteration in the level of a messenger RNA transcript of an TSC-X gene, (6) aberrant modification of an TSC-X gene, such as of the methylation pattern of the genomic DNA, (7) the presence of a non-wild type splicing pattern of a messenger RNA transcript of an TSC-X gene, (8) a non-wild type level of an TSC-X-protein, (9) allelic loss of an TSC-X gene, and (10) inappropriate post-translational modification of an TSC-X-protein. As described herein, there are a large number of assay techniques known in the art which can be used for detecting lesions in an TSC-X gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the TSC-X-gene (see Abravaya et al. (1995) *Nucl Acids Res* 23:675–682). This method can include the steps of collecting a sample of cells from a patient, isolating nucleic acid (e.g., genomic, mRNA or both) from the cells of the sample, contacting the nucleic acid sample with one or more primers that specifically hybridize to an TSC-X gene under conditions such that hybridization and amplification of the TSC-X gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al., 1990, *Proc Natl Acad Sci USA* 87:1874–1878), transcriptional amplification system (Kwoh, et al., 1989, *Proc Natl Acad Sci USA* 86:1173–1177), Q-Beta Replicase (Lizardi et al., 1988, *BioTechnology* 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an TSC-X gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,493,531) can be used to score for the presence of specific mutations by development or loss of a ribozyme cleavage site.

In other embodiments, genetic mutations in TSC-X can be identified by hybridizing a sample and control nucleic acids, e.g., DNA or RNA, to high density arrays containing hundreds or thousands of oligonucleotides probes (Cronin et al. (1996) Human Mutation 7: 244–255; Kozal et al. (1996) *Nature Medicine* 2: 753–759). For example, genetic mutations in TSC-X can be identified in two dimensional arrays containing light-generated DNA probes as described in Cronin et al. above. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the TSC-X gene and detect mutations by comparing the sequence of the sample TSC-X with the corresponding wild-type (control) sequence. Examples of sequencing reactions include those based on techniques developed by Maxim and Gilbert (1977) *PNAS* 74:560 or Sanger (1977) *PNAS* 74:5463. It is also contemplated that any of a variety of automated sequencing procedures can be utilized when performing the diagnostic assays (Naeve et al., (1995) *Biotechniques* 19:448), including sequencing by mass spectrometry (see, e.g., PCT International Publ. No. WO 94/16101; Cohen et al. (1996) *Adv Chromatogr* 36:127–162; and Griffin et al. (1993) *Appl Biochem Biotechnol* 38:147–159).

Other methods for detecting mutations in the TSC-X gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type TSC-X sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc Natl Acad Sci USA* 85:4397; Saleeba et al (1992) *Methods Enzymol* 217:286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in TSC-X cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on an TSC-X sequence, e.g., a wild-type TSC-X sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in TSC-X genes. For example, single strand conformation polymorphism (SSCP) may be used to detect differences in electrophoretic mobility between mutant and wild type nucleic acids (Orita et al. (1989) *Proc Natl Acad Sci USA*: 86:2766, see also Cotton (1993) *Mutat Res* 285:125–144; Hayashi (1992) *Genet Anal Tech Appl* 9:73–79). Single-stranded DNA fragments of sample and control TSC-X nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al (1992) *Mol Cell Probes* 6:1). It is anticipated that in certain embodiments amplification may also be performed using Taq ligase for amplification (Barany (1991) *Proc Natl Acad Sci USA* 88:189). In such cases, ligation will occur only if there is a perfect match at the 3' end of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an TSC-X gene.

Furthermore, any cell type or tissue, preferably peripheral blood leukocytes, in which TSC-X is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on TSC-X activity (e.g., TSC-X gene expression), as identified by a screening assay described herein can be administered to individuals to treat (prophylactically or therapeutically) disorders (e.g., cancer or immune disorders associated with aberrant TSC-X activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of TSC-X protein, expression of TSC-X nucleic acid, or mutation content of TSC-X genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, *Clin Exp Pharmacol Physiol*, 1996, 23:983–985 and Linder, *Clin Chem*, 1997, 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. At the other extreme are the so called ultra-rapid metabolizers who do not respond to standard doses. Recently, the molecular basis of ultra-rapid metabolism has been identified to be due to CYP2D6 gene amplification.

Thus, the activity of TSC-X protein, expression of TSC-X nucleic acid, or mutation content of TSC-X genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an TSC-X modulator, such as a modulator identified by one of the exemplary screening assays described herein.

Monitoring of Effects During Clinical Trials

Monitoring the influence of agents (e.g., drugs, compounds) on the expression or activity of TSC-X (e.g., the ability to modulate aberrant cell proliferation and/or differentiation) can be applied not only in basic drug screening, but also in clinical trials. For example, the effectiveness of an agent determined by a screening assay as described herein to increase TSC-X gene expression, protein levels, or upregulate TSC-X activity, can be monitored in clinical trails of subjects exhibiting decreased TSC-X gene expression, protein levels, or downregulated TSC-X activity. Alternatively, the effectiveness of an agent determined by a screening assay to decrease TSC-X gene expression, protein levels, or downregulate TSC-X activity, can be monitored in clinical trails of subjects exhibiting increased TSC-X gene expression, protein levels, or upregulated TSC-X activity. In such clinical trials, the expression or activity of TSC-X and, preferably, other genes that have been implicated in, for example, a cellular proliferation or immune disorder can be used as a "read out" or markers of the immune responsiveness of a particular cell.

For example, and not by way of limitation, genes, including TSC-X, that are modulated in cells by treatment with an agent (e.g., compound, drug or small molecule) that modulates TSC-X activity (e.g., identified in a screening assay as described herein) can be identified. Thus, to study the effect of agents on cellular proliferation disorders, for example, in a clinical trial, cells can be isolated and RNA prepared and analyzed for the levels of expression of TSC-X and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of TSC-X or other genes. In this way, the gene expression pattern can serve as a marker, indicative of the physiological response of the cells to the agent. Accordingly, this response state may be determined before, and at various points during, treatment of the individual with the agent.

In one embodiment, the present invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of an TSC-X protein, mRNA, or genomic DNA in the preadministration sample; (iii) obtaining one or more post-administration samples from the subject; (iv) detecting the level of expression or activity of the TSC-X protein, mRNA, or genomic DNA in the post-administration samples; (v) comparing the level of expression or activity of the TSC-X protein, mRNA, or genomic DNA in the pre-administration sample with the TSC-X protein, mRNA, or genomic DNA in the post administration sample or samples; and (vi) altering the administration of the agent to the subject accordingly. For example, increased administration of the agent may be desirable to increase the expression or activity of TSC-X to higher levels than detected, i.e., to increase the effectiveness of the agent. Alternatively, decreased administration of the agent may be desirable to decrease expression or activity of TSC-X to lower levels than detected, i.e., to decrease the effectiveness of the agent.

Methods of Treatment

The present invention provides for both prophylactic and therapeutic methods of treating a subject at risk of (or susceptible to) a disorder or having a disorder associated with aberrant TSC-X expression or activity.

Disorders

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to, (i) an aforementioned peptide, or analogs, derivatives, fragments or homologs thereof, (ii) antibodies to an aforementioned peptide; (iii) nucleic acids encoding an aforementioned peptide; (iv) administration of antisense nucleic acid and nucleic acids that are "dysfunctional" (i.e., due to a heterologous insertion within the coding sequences of coding sequences to an aforementioned peptide) that are utilized to "knockout" endogenous function of an aforementioned peptide by homologous recombination (see, e.g., Capecchi, 1989, *Science* 244: 1288–1292); or (v) modulators (i.e., inhibitors, agonists and antagonists, including additional peptide mimetic of the invention or antibodies specific to a peptide of the invention) that alter the interaction between an aforementioned peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, an aforementioned peptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

Prophylactic Methods

In one aspect, the invention provides a method for preventing, in a subject, a disease or condition associated with an aberrant TSC-X expression or activity, by administering to the subject an agent that modulates TSC-X expression or at least one TSC-X activity. Subjects at risk for a disease that is caused or contributed to by aberrant TSC-X expression or activity can be identified by, for example, any or a combination of diagnostic or prognostic assays as described herein. Administration of a prophylactic agent can occur prior to the manifestation of symptoms characteristic of the TSC-X aberrancy, such that a disease or disorder is prevented or, alternatively, delayed in its progression. Depending on the type of TSC-X aberrancy, for example, an TSC-X agonist or TSC-X antagonist agent can be used for treating the subject. The appropriate agent can be determined based on screening assays described herein. The prophylactic methods of the present invention are further discussed in the following subsections.

Therapeutic Methods

Another aspect of the invention pertains to methods of modulating TSC-X expression or activity for therapeutic purposes. The modulatory method of the invention involves contacting a cell with an agent that modulates one or more of the activities of TSC-X protein activity associated with the cell. An agent that modulates TSC-X protein activity can be an agent as described herein, such as a nucleic acid or a protein, a naturally-occurring cognate ligand of an TSC-X protein, a peptide, an TSC-X peptidomimetic, or other small molecule. In one embodiment, the agent stimulates one or more TSC-X protein activity. Examples of such stimulatory agents include active TSC-X protein and a nucleic acid molecule encoding TSC-X that has been introduced into the cell. In another embodiment, the agent inhibits one or more TSC-X protein activity. Examples of such inhibitory agents include antisense TSC-X nucleic acid molecules and anti-TSC-X antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of an TSC-X protein or nucleic acid molecule. In one embodiment, the method involves administering an agent (e.g., an agent identified by a screening assay described herein), or combination of agents that modulates (e.g., upregulates or downregulates) TSC-X expression or activity. In another embodiment, the method involves administering an TSC-X protein or nucleic acid molecule as therapy to compensate for reduced or aberrant TSC-X expression or activity.

Stimulation of TSC-X activity is desirable in situations in which TSC-X is abnormally downregulated and/or in which increased TSC-X activity is likely to have a beneficial effect. One example of such a situation is where a subject has a disorder characterized by aberrant cell proliferation and/or differentiation (e.g., cancer or immune associated disorders). Another example of such a situation is where the subject has a gestational disease (e.g., preclampsia).

Determination of the Biological Effect of the Therapeutic

In various embodiments of the present invention, suitable in vitro or in vivo assays are performed to determine the effect of a specific Therapeutic and whether its administration is indicated for treatment of the affected tissue.

In various specific embodiments, in vitro assays may be performed with representative cells of the type(s) involved in the patient's disorder, to determine if a given Therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects Malignancies Therapeutics of the present invention may be useful in the therapeutic or prophylactic treatment of diseases or disorders that are associated with cell hyperproliferation and/or loss of control of cell proliferation (e.g., cancers, malignancies and tumors). For a review of such hyperproliferation disorders, see e.g., Fishman, et al., 1985. *Medicine*, 2nd ed., J.B. Lippincott Co., Philadelphia, Pa.

Therapeutics of the present invention may be assayed by any method known within the art for efficacy in treating or preventing malignancies and related disorders. Such assays include, but are not limited to, in vitro assays utilizing transformed cells or cells derived from the patient's tumor, as well as in vivo assays using animal models of cancer or malignancies. Potentially effective Therapeutics are those that, for example, inhibit the proliferation of tumor-derived or transformed cells in culture or cause a regression of tumors in animal models, in comparison to the controls.

In the practice of the present invention, once a malignancy or cancer has been shown to be amenable to treatment by modulating (i.e., inhibiting, antagonizing or agonizing) activity, that cancer or malignancy may subsequently be treated or prevented by the administration of a Therapeutic that serves to modulate protein function.

Premalignant Conditions

The Therapeutics of the present invention that are effective in the therapeutic or prophylactic treatment of cancer or malignancies may also be administered for the treatment of pre-malignant conditions and/or to prevent the progression of a pre-malignancy to a neoplastic or malignant state. Such prophylactic or therapeutic use is indicated in conditions known or suspected of preceding progression to neoplasia or cancer, in particular, where non-neoplastic cell growth consisting of hyperplasia, metaplasia or, most particularly, dysplasia has occurred. For a review of such abnormal cell growth see e.g., Robbins & Angell, 1976. *Basic Pathology*, 2nd ed., W.B. Saunders Co., Philadelphia, Pa.

Hyperplasia is a form of controlled cell proliferation involving an increase in cell number in a tissue or organ, without significant alteration in its structure or function. For example, it has been demonstrated that endometnial hyperplasia often precedes endometrial cancer. Metaplasia is a form of controlled cell growth in which one type of mature or fully differentiated cell substitutes for another type of mature cell. Metaplasia may occur in epithelial or connective tissue cells. Dysplasia is generally considered a precursor of cancer, and is found mainly in the epithelia. Dysplasia is the most disorderly form of non-neoplastic cell growth, and involves a loss in individual cell uniformity and in the architectural orientation of cells. Dysplasia characteristically occurs where there exists chronic irritation or inflammation, and is often found in the cervix, respiratory passages, oral cavity, and gall bladder.

Alternatively, or in addition to the presence of abnormal cell growth characterized as hyperplasia, metaplasia, or dysplasia, the presence of one or more characteristics of a transformed or malignant phenotype displayed either in vivo or in vitro within a cell sample derived from a patient, is indicative of the desirability of prophylactic/therapeutic administration of a Therapeutic that possesses the ability to modulate activity of An aforementioned protein. Characteristics of a transformed phenotype include, but are not limited to: (i) morphological changes; (ii) looser substratum attachment; (iii) loss of cell-to-cell contact inhibition; (iv) loss of anchorage dependence; (v) protease release; (vi) increased sugar transport; (vii) decreased serum requirement; (viii) expression of fetal antigens, (ix) disappearance of the 250 kDal cell-surface protein, and the like. See e.g., Richards, et al., 1986. *Molecular Pathology*, W.B. Saunders Co., Philadelphia, Pa.

In a specific embodiment of the present invention, a patient that exhibits one or more of the following predisposing factors for malignancy is treated by administration of an effective amount of a Therapeutic: (i) a chromosomal translocation associated with a malignancy (e.g., the Philadelphia chromosome (bcr/abl) for chronic myelogenous leukemia and t(14;18) for follicular lymphoma, etc.); (ii) familial polyposis or Gardner's syndrome (possible forerunners of colon cancer); (iii) monoclonal gammopathy of undetermined significance (a possible precursor of multiple myeloma) and (iv) a first degree kinship with persons having a cancer or pre-cancerous disease showing a Mendelian (genetic) inheritance pattern (e.g., familial polyposis of the colon, Gardner's syndrome, hereditary exostosis, polyendocrine adenomatosis, Peutz-Jeghers syndrome, neurofibromatosis of Von Recklinghausen, medullary thyroid carcinoma with amyloid production and pheochromocytoma, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia and Bloom's syndrome).

In another embodiment, a Therapeutic of the present invention is administered to a human patient to prevent the progression to breast, colon, lung, pancreatic, or uterine cancer, or melanoma or sarcoma.

Hyperproliferative and Dysproliferative Disorders

In one embodiment of the present invention, a Therapeutic is administered in the therapeutic or prophylactic treatment of hyperproliferative or benign dysproliferative disorders. The efficacy in treating or preventing hyperproliferative diseases or disorders of a Therapeutic of the present invention may be assayed by any method known within the art. Such assays include in vitro cell proliferation assays, in vitro or in vivo assays using animal models of hyperproliferative diseases or disorders, or the like. Potentially effective Therapeutics may, for example, promote cell proliferation in culture or cause growth or cell proliferation in animal models in comparison to controls.

Specific embodiments of the present invention are directed to the treatment or prevention of cirrhosis of the liver (a condition in which scarring has overtaken normal liver regeneration processes); treatment of keloid (hypertrophic scar) formation causing disfiguring of the skin in which the scarring process interferes with normal renewal; psoriasis (a common skin condition characterized by excessive proliferation of the skin and delay in proper cell fate determination); benign tumors; fibrocystic conditions and tissue hypertrophy (e.g., benign prostatic hypertrophy).

Neurodegenerative Disorders

TSC-X protein have been implicated in the deregulation of cellular maturation and apoptosis, which are both characteristic of neurodegenerative disease. Accordingly, Therapeutics of the invention, particularly but not limited to those that modulate (or supply) activity of an aforementioned protein, may be effective in treating or preventing neurodegenerative disease. Therapeutics of the present invention that modulate the activity of an aforementioned protein involved in neurodegenerative disorders can be assayed by any method known in the art for efficacy in treating or preventing such neurodegenerative diseases and disorders. Such assays include in vitro assays for regulated cell maturation or inhibition of apoptosis or in vivo assays using animal models of neurodegenerative diseases or disorders, or any of the assays described below. Potentially effective Therapeutics, for example but not by way of limitation, promote regulated cell maturation and prevent cell apoptosis in culture, or reduce neurodegeneration in animal models in comparison to controls.

Once a neurodegenerative disease or disorder has been shown to be amenable to treatment by modulation activity, that neurodegenerative disease or disorder can be treated or prevented by administration of a Therapeutic that modulates activity. Such diseases include all degenerative disorders involved with aging, especially osteoarthritis and neurodegenerative disorders.

Disorders Related to Organ Transplantation

Therapeutics of the invention, particularly those that modulate (or supply) activity, may be effective in treating or preventing diseases or disorders related to organ transplantation. Therapeutics of the invention (particularly Therapeutics that modulate the levels or activity of an aforementioned protein) can be assayed by any method known in the art for efficacy in treating or preventing such diseases and disorders related to organ transplantation. Such assays include in vitro assays for using cell culture models as described below, or in vivo assays using animal models of diseases and disorders related to organ transplantation, see e.g. below. Potentially effective Therapeutics, for example but not by way of limitation, reduce immune rejection responses in animal models in comparison to controls.

Accordingly, once diseases and disorders related to organ transplantation are shown to be amenable to treatment by modulation of activity, such diseases or disorders can be treated or prevented by administration of a Therapeutic that modulates activity.

Cardiovascular Disease

Diseases such as cardiovascular disease, including cerebral thrombosis or hemorrhage, ischemic heart or renal disease, peripheral vascular disease, or thrombosis of other major vessel, and other diseases, including diabetes mellitus, hypertension, hypothyroidism, cholesterol ester storage disease, systemic lupus erythematosus, homocysteinemia, and familial protein or lipid processing diseases, and the like, are either directly or indirectly associated with atherosclerosis. Accordingly, Therapeutics of the invention, particularly those that modulate (or supply) activity or formation may be effective in treating or preventing atherosclerosis-associated diseases or disorders. Therapeutics of the invention (particularly Therapeutics that modulate the levels or activity) can be assayed by any method known in the art, including those described below, for efficacy in treating or preventing such diseases and disorders.

A vast array of animal and cell culture models exist for processes involved in atherosclerosis. A limited and non-exclusive list of animal models includes knockout mice for premature atherosclerosis (Kurabayashi and Yazaki, 1996, Int. Angiol. 15: 187–194), transgenic mouse models of atherosclerosis (Kappel et al., 1994, FASEB J. 8: 583–592), antisense oligonucleotide treatment of animal models (Callow, 1995, Curr. Opin. Cardiol. 10: 569–576), transgenic rabbit models for atherosclerosis (Taylor, 1997, Ann. N.Y. Acad. Sci 811: 146–152), hypercholesterolemic animal models (Rosenfeld, 1996, Diabetes Res. Clin. Pract. 30 Suppl.: 1–11), hyperlipidemic mice (Paigen et al., 1994, Curr. Opin. Lipidol. 5: 258–264), and inhibition of lipoxygenase in animals (Sigal et al., 1994, Ann. N.Y. Acad. Sci. 714: 211–224). In addition, in vitro cell models include but are not limited to monocytes exposed to low density lipoprotein (Frostegard et al., 1996, Atherosclerosis 121: 93–103), cloned vascular smooth muscle cells (Suttles et al., 1995, Exp. Cell Res. 218: 331–338), endothelial cell-derived chemoattractant exposed T cells (Katz et al., 1994, J. Leukoc. Biol. 55: 567–573), cultured human aortic endothelial cells (Farber et al., 1992, Am. J. Physiol. 262: H1088–1085), and foam cell cultures (Libby et al., 1996, Curr Opin Lipidol 7: 330–335). Potentially effective Therapeutics, for example but not by way of limitation, reduce foam cell formation in cell culture models, or reduce atherosclerotic plaque formation in hypercholesterolemic mouse models of atherosclerosis in comparison to controls.

Accordingly, once an atherosclerosis-associated disease or disorder has been shown to be amenable to treatment by modulation of activity or formation, that disease or disorder can be treated or prevented by administration of a Therapeutic that modulates activity.

Cytokine and Cell Proliferation/Differentiation Activity

An TSC-X protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7e and CMK.

The activity of a protein of the invention may, among other means, be measured by the following methods: Assays for T-cell or thymocyte proliferation include without limitation those described in: *Current Protocols in Immunology*, Ed by Coligan et al., Greene Publishing Associates and Wiley-Interscience (Chapter 3 and Chapter 7); Takai et al., *J Immunol* 137:3494–3500, 1986; Bertagnolli et al., *J Immunol* 145:1706–1712, 1990; Bertagnolli et al., *Cell Immunol* 133:327–341, 1991; Bertagnolli, et al., *J Immunol* 149:3778–3783, 1992; Bowman et al., *J Immunol* 152:1756–1761, 1994.

Assays for cytokine production and/or proliferation of spleen cells, lymph node cells or thymocytes include, without limitation, those described by Kruisbeek and Shevach, In: *Current Protocols in Immunology*. Coligan et al., eds. Vol 1, pp. 3.12.1–1$^4$, John Wiley and Sons, Toronto 1994; and by Schreiber, In: *Current Protocols in Immunology*. Coligan eds. Vol 1 pp. 6.8.1–8, John Wiley and Sons, Toronto 1994.

Assays for proliferation and differentiation of hematopoietic and lymphopoietic cells include, without limitation, those described by Bottomly et al., In: *Current Protocols in Immunology*. Coligan et al., eds. Vol 1 pp. 6.3.1–6.3.12, John Wiley and Sons, Toronto 1991; deVries et al., *J Exp Med* 173:1205–1211, 1991; Moreau et al., *Nature* 336:690–692, 1988; Greenberger et al., Proc Natl Acad Sci U.S.A. 80:2931–2938, 1983; Nordan, In: *Current Protocols in Immunology*. Coligan et al., eds. Vol 1 pp. 6.6.1–5, John Wiley and Sons, Toronto 1991; Smith et al., *Proc Natl Acad Sci U.S.A.* 83:1857–1861, 1986; Measurement of human Interleukin 11-Bennett, et al. In: *Current Protocols in Immunology*. Coligan et al., eds. Vol 1 pp. 6.15.1 John Wiley and Sons, Toronto 1991; Ciarletta, et al., In: *Current Protocols in Immunology*. Coligan et al., eds. Vol 1 pp. 6.13.1, John Wiley and Sons, Toronto 1991.

Assays for T-cell clone responses to antigens (which will identify, among others, proteins that affect APC-T cell interactions as well as direct T-cell effects by measuring proliferation and cytokine production) include, without limitation, those described In: *Current Protocols in Immunology*. Coligan et al., eds., Greene Publishing Associates and Wiley-Interscience (Chapter 3 Chapter 6, Chapter 7); Weinberger et al., *Proc Natl Acad Sci USA* 77:6091–6095, 1980; Weinberger et al., *Eur J Immun* 11:405–411, 1981; Takai et al., *J Immunol* 137:3494–3500, 1986; Takai et al., *J Immunol* 140:508–512, 1988.

Immune Stimulating or Suppressing Activity

An TSC-X protein of the present invention may also exhibit immune stimulating or immune suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by vital (e.g., HIV) as well as bacterial or fungal infections, or may result from autoimmune disorders. More specifically, infectious diseases causes by vital, bacterial, fungal or other infection may be treatable using a protein of the present invention, including infections by HIV, hepatitis viruses, herpesviruses, mycobacteria, Leishmania species., malaria species. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or energy in T cells, is distinguishable from immunosuppression in that it is generally antigen-specific and persists after exposure to the tolerizing agent has ceased. Operationally, tolerance can be demonstrated by the lack of a T cell response upon re-exposure to specific antigen in the absence of the tolerizing agent.

Down regulating or preventing one or more antigen functions (including without limitation B lymphocyte antigen functions (such as, for example, B7), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to energize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc Natl Acad Sci USA, 89:11102–11105 (1992). In addition, murine models of GVHD (see Paul ed., Fundamental Immunology, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and auto-antibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of auto-antibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythematosis in MRL/lpr/lpr mice or NZB hybrid mice, murine autoimmune collagen arthritis, diabetes mellitus in NOD mice and BB rats, and murine experimental myasthenia gravis (see Paul ed., *Fundamental Immunology*, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic vital diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-vital immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class I α chain protein and $\beta_2$ microglobulin protein or an MHC class II a chain protein and an MHC class II β chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods: Suitable assays for thymocyte or splenocyte cytotoxicity include, without limitation, those described In: *Current Protocols in Immunology*. Coligan et al., eds. Greene Publishing Associates and Wiley-Interscience (Chapter 3, Chapter 7); Herrmann et al., *Proc Natl Acad Sci USA* 78:2488–2492, 1981; Herrmann et al., *J Immunol* 128:1968–1974, 1982; Handa et al., *J Immunol* 135:1564–1572, 1985; Takai et al., *J Immunol* 137:3494–3500, 1986; Takai et al., *J Immunol* 140:508–512, 1988; Herrmann et al., *Proc Natl Acad Sci USA* 78:2488–2492, 1981; Herrmann et al., *J Immunol* 128:1968–1974, 1982; Handa et al., *J Immunol* 135:1564–1572, 1985; Takai et al., *J Immunol* 137:3494–3500, 1986; Bowman et al., *J Virology* 61:1992–1998; Takai et al., *J Immunol* 140:508–512, 1988; Bertagnolli et al., *Cell Immunol* 133:327–341, 1991; Brown et al., *J Immunol* 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, *J Immunol* 144:3028–3033, 1990; and Mond and Brunswick In: *Current Protocols in Immunology*. Coligan et al., (eds.) Vol 1 pp. 3.8.1–3.8.16, John Wiley and Sons, Toronto 1994.

Mixed lymphocyte reaction (MLR) assays (which will identify, among others, proteins that generate predominantly Th1 and CTL responses) include, without limitation, those described In: *Current Protocols in Immunology*. Coligan et al., eds. Greene Publishing Associates and Wiley-Interscience (Chapter 3, Chapter 7); Takai et al., *J Immunol* 137:3494–3500, 1986; Takai et al., *J Immunol* 140:508–512, 1988; Bertagnolli et al., *J Immunol* 149:3778–3783, 1992.

Dendritic cell-dependent assays (which will identify, among others, proteins expressed by dendritic cells that activate naive T-cells) include, without limitation, those described in: Guery et al., *J Immunol* 134:536–544, 1995; Inaba et al., *J Exp Med* 173:549–559, 1991; Macatonia et al., *J Immunol* 154:5071–5079, 1995; Porgador et al., *J Exp Med* 182:255–260, 1995; Nair et al., *J Virol* 67:4062–4069, 1993; Huang et al., *Science* 264:961–965, 1994; Macatonia et al., *J Exp Med* 169:1255–1264, 1989; Bhardwaj et al., *J Clin Investig* 94:797–807, 1994; and Inaba et al., *J Exp Med* 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., *Cytometry* 13:795–808, 1992; Gorczyca et al., *Leukemia* 7:659–670, 1993; Gorczyca et al., *Cancer Res* 53:1945–1951, 1993; Itoh et al., *Cell* 66:233–243, 1991; Zacharchuk, *J Immunol* 145:4037–4045, 1990; Zamai et al., *Cytometry* 14:891–897, 1993; Gorczyca et al., *Internat J Oncol* 1:639–648, 1992.

Assays for proteins that influence early steps of T-cell commitment and development include, without limitation, those described in: Antica et al., *Blood* 84:111–117, 1994; Fine et al., *Cell Immunol* 155: 111–122, 1994; Galy et al., *Blood* 85:2770–2778, 1995; Toki et al., *Proc Nat Acad Sci USA* 88:7548–7551, 1991.

Hematopoiesis Regulating Activity

An TSC-X protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. *Cellular Biology* 15:141–151, 1995; Keller et al., *Mol. Cell. Biol.* 13:473–486, 1993; McClanahan et al., *Blood* 81:2903–2915, 1993.

Assays for stem cell survival and differentiation (which will identify, among others, proteins that regulate lymphohematopoiesis) include, without limitation, those described in: Methylcellulose colony forming assays, Freshney, In: *Culture of Hematopoietic Cells*. Freshney, et al. (eds.) Vol pp. 265–268, Wiley-Liss, Inc., New York, N.Y. 1994; Hirayama et al., *Proc Natl Acad Sci USA* 89:5907–5911, 1992; McNiece and Briddeli, In: *Culture of Hematopoietic Cells*. Freshney, et al. (eds.) Vol pp. 23–39, Wiley-Liss, Inc., New York, N.Y. 1994; Neben et al., *Exp Hematol* 22:353–359, 1994; Ploemacher, In: *Culture of Hematopoietic Cells*. Freshney, et al. eds. Vol pp. 1–21, Wiley-Liss, Inc., New York, N.Y. 1994; Spooncer et al., In: *Culture of Hematopoietic Cells*. Freshhey, et al., (eds.) Vol pp. 163–179, Wiley-Liss, Inc., New York, N.Y. 1994; Sutherland, In: *Culture of Hematopoietic Cells*. Freshney, et al., (eds.) Vol pp. 139–162, Wiley-Liss, Inc., New York, N.Y. 1994.

Tissue Growth Activity

An TSC-X protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendonitis, carpal tunnel syndrome and other tendon or ligament defects. The compositions may also include an appropriate matrix and/or sequestering agent as a career as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by assays for tissue generation activity known in the art. These include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, *Epidermal Wound Healing*, pp. 71–112 (Maibach and Rovee, eds.), Year Book Medical Publishers, Inc., Chicago, as modified by Eaglstein and Menz, *J. Invest. Dermatol* 71:382–84 (1978).

Activin/Inhibin Activity

An TSC-X protein of the present invention may also exhibit activin- or inhibin-related activities. Inhibins are characterized by their ability to inhibit the release of follicle stimulating hormone (FSH), while activins are and are characterized by their ability to stimulate the release of follicle stimulating hormone (FSH). Thus, a protein of the present invention, alone or in heterodimers with a member of the inhibin a family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-b group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by methods known in the art. For example, assays for activin/inhibin activity include, without limitation, those described in: Vale et al., *Endocrinology* 91:562–572, 1972; Ling et al., *Nature* 321:779–782, 1986; Vale et al., *Nature* 321:776–779, 1986; Mason et al., *Nature* 318:659–663, 1985; Forage et al., *Proc Natl Acad Sci USA* 83:3091–3095, 1986.

Chemotactic/Chemokinetic Activity

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: *Current Protocols in Immunology*, Coligan et al., eds. (Chapter 6.12, *Measurement of Alpha and Beta Chemokines* 6.12.1–6.12.28); Taub et al. *J Clin Invest* 95:13 70–13 76, 1995; Lind et al. *APMIS* 103:140–146, 1995; Muller et al., *Eur J Immunol* 25: 1744–1748; Gruberet al. *J Immunol* 152:5860–5867, 1994; Johnston et al., *J Immunol* 153: 1762–1768, 1994.

Hemostatic and Thrombolytic Activity

A protein of the invention may also exhibit hemostatic or thrombolytic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., *J. Clins. Pharmacol.* 26:131–140, 1986; Burdick et al., *Thrombosis Res.* 45:413–419, 1987; Humphrey et al., *Fibrinolysis* 5:71–79 (1991); Schaub, *Prostaglandins* 35:467–474, 1988.

Receptor/Ligand Activity

A protein of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell—cell interactions and their ligands (including without limitation, cellular adhesion molecules (such as selecting, integrins and their ligands) and receptoraigand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in: *Current Protocols in Immunology*, Ed by Coligan, et al., Greene Publishing Associates and Wiley-Interscience (Chapter 7.28, Measurement of Cellular Adhesion under static conditions 7.28.1–7.28.22), Takai et al., *Proc Natl Acad Sci USA* 84:6864–6868, 1987; Bierer et al., *J. Exp. Med.* 168:1145–1156, 1988; Rosenstein et al., *J. Exp. Med.* 169:149–160 1989; Stoltenborg et al., *J Immunol Methods* 175:59–68, 1994; Stitt et al., *Cell* 80:661–670, 1995.

Anti-Inflammatory Activity

Proteins of the present invention may also exhibit anti-inflammatory activity. The anti-inflammatory activity may be achieved by providing a stimulus to cells involved in the inflammatory response, by inhibiting or promoting cell—cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation inflammation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

Tumor Inhibition Activity

In addition to the activities described above for immunological treatment or prevention of tumors, a protein of the invention may exhibit other anti-tumor activities. A protein may inhibit tumor growth directly or indirectly (such as, for example, via ADCC). A protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth.

Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or circadian cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

General Screeening and Diagnostic Methods Using Differential Expression of TSCX Sequences Several of the herein disclosed methods relate to comparing the levels of expression of one or more TSCX nucleic acids in a test and reference cell populations. The sequence information disclosed herein, coupled with nucleic acid detection methods known in the art, allow for detection and comparison of the various TSCX transcripts. In some embodiments, the TSCX nucleic acids and polypeptides correspond to nucleic acids or polypeptides which include the various sequences (referenced by SEQ ID NOs) disclosed for each TSCX nucleic acid sequence.

In its various aspects and embodiments, the invention includes providing a test cell population which includes at least one cell that is capable of expressing one or more of the sequences TSCX1–41, or any combination of TSCX sequences thereof By "capable of expressing", it is meant that the gene is present in an intact form in the cell and can be expressed. Expression of one, some, or all of the TSCX sequences is then detected, if present, and, preferably, measured. Using sequence information provided by the database entries for the known sequences, or the sequence information for the newly described sequences, expression of the TSCX sequences can be detected (if expressed) and measured using techniques well known to one of ordinary skill in the art. For example, sequences within the sequence database entries corresponding to TSCX sequences, or within the sequences disclosed herein, can be used to construct probes for detecting TSCX RNA sequences in, e.g., northern blot hybridization analyses or methods which specifically, and, preferably, quantitatively amplify specific nucleic acid sequences. As another example, the sequences can be used to construct primers for specifically amplifying the TSCX sequences in, e.g., amplification-based detection methods such as reverse-transcription based polymerase chain reaction. When alterations in gene expression are associated with gene amplification or deletion, sequence comparisons in test and reference populations can be made by comparing relative amounts of the examined DNA sequences in the test and reference cell populations.

For TSCX sequences whose polypeptide product is known, expression can be also measured at the protein level, i.e., by measuring the levels of polypeptides encoded by the gene products described herein. Such methods are well known in the art and include, e.g., immunoassays based on antibodies to proteins encoded by the genes.

The expression level of one or more of the TSCX sequences in the test cell population is then compared to expression levels of the sequences in one or more cells from a reference cell population. Expression of sequences in test and control ("normal") populations of cells can be compared using any art-recognized method for comparing expression of nucleic acid sequences. For example, expression can be compared using GENECALLING™ methods as described in U.S. Pat. No. 5,871,697 and in Shimkets et al., Nat. Biotechnol. 17:798–803 (1999).

In various embodiments, the expression of 2, 3, 4, 5, 6, 7, 8, 9, 10, 15, 20, 25, 28, 30, 35, 40, or all of the sequences represented by TSCX1–41 are measured. If desired, expression of these sequences can be measured along with other sequences whose expression is known to be altered according to one of the herein described parameters or conditions. For example, expression of one or more of sequences represented by TSCX1–41 can be compared with e.g., sequences in Table 5.

TSCX sequence corresponds to the change in expression level observed for the TSCX sequence present in a TSC lesion as shown in Table 1.

If desired, comparison of differentially expressed sequences between a test cell population and a reference cell population can be done with respect to a control nucleic acid whose expression is independent of the parameter or condition being measured. Expression levels of the control nucleic acid in the test and reference nucleic acid can be used to normalize signal levels in the compared populations. Suitable control nucleic acids can readily be determined by one of ordinary skill in the art.

In some embodiments, the test cell population is compared to multiple reference cell populations. Each of the multiple reference populations may differ in the known parameter. Thus, a test cell population may be compared to a first reference cell population known to be from a lesion

TABLE 5

| Gene Name | Acc # | Literature Determined Gene Response |
|---|---|---|
| Hamartin | AF013168 | Loss of protein function in lesion may potentially be caused by a nonsense mutation or one affecting restriction sites. |
| Tuberin | X75621 | Loss of protein function in lesion may potentially be caused by a nonsense mutation or one affecting restriction sites. |
| Rap1a | X12533 | Shown to bind to and be activated by Tuberin |
| Rab5 | M28215 | Shown to bind to and be activated by Tuberin |
| Rabaptin-5 | X91141 | Shown to bind to both Tuberin and Rab5, thought to recruit Rab5 for activation |
| Alpha B crystallin (TSC14) | S45630 | Is up regulated in TSC tumors in a variety of organs. |

The reference cell population includes cells one or more cells capable of expressing the measured TSCX sequences and for which the compared parameter is known, e.g., hyperproliferative disorder expression status. By "hyperproliferative disorder expression status" is meant that it is known whether the reference cell is derived from a lesion associated with a hyperproliferative condition. A hyperproliferative disorder can be, e.g., a TSC-associated condition, or a dermatological or neoplastic cell. Whether or not comparison of the gene expression profile in the test cell population to the reference cell population reveals the presence, or degree, of the measured parameter depends on the composition of the reference cell population. For example, if the reference cell population is composed of cells that are not from a sample having a hyperproliferative condition, a similar gene expression level in the test cell population and a reference cell population indicates that the sample does not contain cells with a hyperproliferative condition. Conversely, if the reference cell population is made up of cells that are from a hyperproliferative condition, a similar gene expression profile between the test cell population and the reference cell population indicates the test sample includes cells from a hyperproliferative condition.

In various embodiments, a TSCX sequence in a test cell population is considered comparable in expression level to the expression level of the TSCX sequence in the reference cell population if its expression level varies within a factor of 2.0, 1.5, or 1.0 fold to the level of the TSCX transcript in the reference cell population. In various embodiments, a TSCX sequence in a test cell population can be considered altered in levels of expression if its expression level varies from the reference cell population by more than 1.0, 1.5, 2.0 or more fold from the expression level of the corresponding TSCX sequence in the reference cell population. In some embodiments, the variation in expression of a particular associated with a hyperproliferative condition, as well as a second reference population known not be from a hyperproliferative condition.

The test cell population can be any number of cells, i.e., one or more cells, and can be provided in vitro, in vivo, or ex vivo.

In other embodiments, the test cell population can be divided into two or more subpopulations. The subpopulations can be created by dividing the first population of cells to create as identical a subpopulation as possible. This will be suitable, in, for example, in vitro or ex vivo screening methods. In some embodiments, various sub populations can be exposed to a control agent, and/or a test agent, multiple test agents, or, e.g., varying dosages of one or multiple test agents administered together, or in various combinations.

Preferably, cells in the reference cell population are derived from a tissue type as similar as possible to a test cell. In some embodiments, the control cell is derived from the same subject as the test cell, e.g., from a region proximal to the region of origin of the test cell. In other embodiments, the reference cell population is derived from a plurality of cells. For example, the reference cell population can be a database of expression patterns from previously tested cells for which one of the herein-described parameters or conditions (e.g., TSC status, screening, diagnostic, or therapeutic) is known.

The subject is preferably a mammal. The mammal can be, e.g., a human, non-human primate, mouse, rat, dog, cat, horse, or cow.

Screening Assays for Identifying a Candidate Therapeutic Agent for Treating or Preventing a Hyperproliferative Condition The differentially expressed sequences disclosed herein can also be used to identify candidate therapeutic agents pathophysiologies associated with a hyperproliferative condition. The method is based on screening a candidate therapeutic agent to determine if it induces an expression profile of one or more TSCX1–41 sequences in a test cell population that is characteristic of a hyperproliferative condition.

In the method, a test cell population is exposed to a test agent or a combination of test agents (sequentially or consequentially), and the expression of one or more of the TSCX sequences is measured. The expression of the TSCX sequences in the test population is compared to expression level of the TSCX sequences in a reference cell population whose TSC status is known. If the reference cell population contains cells that are from a TSC associated condition, alteration of expression of the nucleic acids in the test cell population as compared to the reference cell population indicates that the test agent is a candidate therapeutic agent.

In some embodiments, the reference cell population includes cells that have been exposed to a test agent. When this cell population is used, an alteration in expression of the nucleic acid sequences in the presence of the agent from the expression profile of the cell population in the absence of the agent indicates the agent is a candidate therapeutic agent. In other embodiments, the test cell population includes cells that are from a TSC associated condition. For this cell population, a similarity in expression of the TSCX sequences in the test and control cell populations indicates the test agent is not a candidate therapeutic agent, while a difference suggests it is a candidate.

The test agent can be a compound not previously described or can be a previously known compound but which is not known to be a TSC therapeutic agent.

An agent effective in stimulating expression of underexpressed genes, or in suppressing expression of overexpressed genes can be further tested for its ability to prevent the hyperproliferative condition and as a potential therapeutic useful for the treatment of an associated pathophysiology. Further evaluation of the clinical usefulness of such a compound can be performed using standard methods of evaluating toxicity and clinical effectiveness of anti-proliferative.

Selecting a Therapeutic Agent for Treating an Anti-proliferative Condition That is Appropriate for a Particular Individual Differences in the genetic makeup of individuals can result in differences in their relative abilities to metabolize various drugs. An agent that is metabolized in a subject to act as a TSC therapeutic can manifest itself by inducing a change in gene expression pattern from that characteristic of a pathophysiologic state to a gene expression pattern characteristic of a non-pathophysiologic state. Accordingly, the differentially expressed TSCX sequences disclosed herein allow for a putative therapeutic or prophylactic agent to be tested in a test cell population from a selected subject in order to determine if the agent is a suitable anti-hyperproliferation Therapeutic in the subject.

To identify the Therapeutic that is appropriate for a specific subject, a test cell population from the subject is exposed to a therapeutic agent, and the expression of one or more of TSCX1–41 sequences is measured.

In some embodiments, the test cell population contains an adipocyte. In other embodiments, the agent is first mixed with a cell extract, e.g., an adipose cell extract, which contains enzymes that metabolize drugs into an active form. The activated form of the therapeutic agent can then be mixed with the test cell population and gene expression measured. Preferably, the cell population is contacted ex vivo with the agent or activated form of the agent.

Expression of the nucleic acid sequences in the test cell population is then compared to the expression of the nucleic acid sequences a reference cell population. The reference cell population includes at least one cell whose hyperproliferation status is known. If the reference cell is not from a hyperproliferative condition, a similar gene expression profile between the test cell population and the reference cell population indicates the agent is suitable for treating the pathophysiology in the subject. A difference in expression between sequences in the test cell population and those in the reference cell population indicates that the agent is not suitable for treating the hyperproliferation pathophysiology in the subject.

If the reference cell has not been exposed to an anti-hyperproliferation Therapeutic, a similarity in gene expression patterns between the test cell population and the reference cell population indicates the agent is not suitable for treating the TSC condition in the subject, while a dissimilar gene expression patterns indicate the agent will be suitable for treating the subject.

The test agent can be any compound or composition. In some embodiments the test agents are compounds and composition known to be TSC Therapeutics.

Methods of Diagnosing Pathophysiologies Associated With TSC

The invention further provides a method of diagnosing a pathophysiology associated with hyperproliferation, e.g., a dermatological condition or a neoplasm. A pathophysiology is diagnosed by examining the expression of one or more TSCX nucleic acid sequences from a test population of cells from a subject suspected of have the pathophysiology.

Expression of one or more of the TSCX nucleic acid sequences, e.g. TSCX1–41 is measured in the test cell and compared to the expression of the sequences in the reference cell population. The reference cell population contains at least one cell whose hyperproliferation status, or disease status (e.g., the reference cell population is from a subject with a hyperproliferative disorder) is known. If the reference cell population contains cells that are not from a hyperproliferative state, then a similarity in expression between TSCX sequences in the test population and the reference cell population indicates the subject does not have a hyperproliferative-associated pathophysiology. A difference in expression between TSCX sequences in the test population and the reference cell population indicates the reference cell population has the pathophysiology.

Conversely, when the reference cell population contains cells that are from hyperproliferative state, a similarity in expression pattern between the test cell population and the reference cell population indicates the test cell population has the pathophysiology. A difference in expression between TSCX sequences in the test population and the reference cell population indicates the subject does not have the pathophysiology.

Methods of Treating Pathpohysiologies Associated With a TSC Condition in a Subject Also included in the invention is a method of treating, i.e, preventing or delaying the onset of a pathophysiology associated with a TSC associated condition in a subject by administering to the subject an agent which modulates the expression or activity of one or more nucleic acids selected from the group consisting of TSCX1–41. "Modulates" is meant to include increase or decrease expression or activity of the TSCX nucleic acids. Preferably, modulation results in alteration alter the expression or activity of the TSCX genes or gene products in a subject to a level similar or identical to a subject not suffering from the pathophysiology.

The pathophysiologies can be any of the hyperproliferative pathophysiologies described herein, e.g., a dermatological condition or a neoplasm. The subject can be, e.g., a human, a rodent such as a mouse or rat, or a dog or cat.

The herein described TSCX nucleic acids, polypeptides, antibodies, agonists, and antagonists when used therapeutically are referred to herein as "Therapeutics". Methods of administration include those described above.

Polynucleotides of the present invention can also be used for gene therapy. Gene therapy refers to therapy that is performed by the administration of a specific nucleic acid to a subject. Delivery of the Therapeutic nucleic acid into a mammalian subject may be either direct (i.e., the patient is directly exposed to the nucleic acid or nucleic acid-containing vector) or indirect (i.e., cells are first transformed with the nucleic acid in vitro, then transplanted into the patient). These two approaches are known, respectively, as in vivo or ex vivo gene therapy. Polynucleotides of the invention may also be administered by other known methods for introduction of nucleic acid into a cell or organism (including, without limitation, in the form of viral vectors or naked DNA). Any of the methodologies relating to gene therapy available within the art may be used in the practice of the present invention. See e.g., Goldspiel et al., Clin. Pharm. 12:488–505 (1993).

Cells may also be cultured ex vivo in the presence of therapeutic agents or proteins of the present invention in order to proliferate or to produce a desired effect on or activity in such cells. Treated cells can then be introduced in vivo for therapeutic purposes.

Assessing Efficacy of Treatment of a TSC Associated Condition in a Subject

The differentially expressed TSCX sequences identified herein also allow for the course of treatment of a pathophysiology to be monitored. In this method, a test cell population is provided from a subject undergoing treatment for pathophysiologies associated with a TSC associated condition. If desired, test cell populations can be taken from the subject at various time points before, during, or after treatment. Expression of one or more of the TSCX sequences, e.g., TSCXs: 1–41 in the cell population is then measured and compared to a reference cell population which includes cells whose pathophysiologic state is known. Preferably, the reference cells not been exposed to the treatment.

If the reference cell population contains no cells exposed to the treatment, a similarity in expression between TSCX sequences in the test cell population and the reference cell population indicates that the treatment is efficacious. However, a difference in expression between TSCX sequences in the test population and this reference cell population indicates the treatment is not efficacious.

By "efficacious" is meant that the treatment leads to a decrease in the pathophysiology in a subject. When treatment is applied prophylactically, "efficacious" means that the treatment retards or prevents a pathophysiology. For example, if the TSC associated condition is subungual fibroma, an "efficacious" treatment is one that decreases the fibroma size.

Efficaciousness can be determined in association with any known method for treating the particular pathophysiology.

Kits and Nucleic Acid Collections for Identifying TSCX Nucleic Acids

In another aspect, the invention provides a kit useful for examining a pathophysiology associated with a TSC condition. The kit can include nucleic acids that detect two or more TSCX sequences. In preferred embodiments, the kit includes reagents which detect 3, 4, 5, 6, 8, 10, 12, 15, 20, 25, 30, 35, 40 or all of the TSCX nucleic acid sequences.

The invention also includes an isolated plurality of sequences which can identify one or more TSCX responsive nucleic acid sequences.

The kit or plurality may include, e.g., sequence homologous to TSCX nucleic acid sequences, or sequences which can specifically identify one or more TSCX nucleic acid sequences.

Nucleotide Polymorphisms Associated With TSCX Genes

The invention also includes nucleic acid sequences that include one or more polymorphic TSCX sequences. Also included are methods of identifying a base occupying a polymorphic in an TSCX sequence, as well as methods of identifying an individualized therapeutic agent for treating TSC associated conditions based on TSCX sequence polymorphisms.

The nucleotide polymorphism can be a single nucleotide polymorphism (SNP). A SNP occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

Single nucleotide polymorphisms (cSNPs) were found in 16 genes. Of these, 7 genes posessed changes that altered amino acids in the resulting protein. Two of these changes (Alpha B crystallin: ASP-GLY and Laminin α4: HIS-TYR) are nonconserved changes which may effect the structure and/or function of the proteins.

Polymorphic sequences according to the present invention can include those shown in Table 6. Table 6 describes 16 TSCX sequences for which polymorphisms have been identified. The first column of the table lists the names assigned to the sequences in which the polymorphisms occur. The second column lists the GerBank Accession numbers for the respective sequences. The third column lists the respective TSC number for the wild-type sequence. Columns four through six relate to SNPs found in 3' or 5' untranslated regions, while columns seven through ten relate to SNPs found in coding regions of the genes. The sixth and ninth columns list the position in the sequence in which the polymorphic site has been found. The fourth and seventh columns list the base occupying the polymorphic site in the sequence in the database, i.e., the wild-type. The fifth and eighth columns list the alternative base at the polymorphic site. The tenth column lists any amino acid change that occurs due to the polymorphism.

The polymorphic sequence can include one or more of the following sequences: (1) a sequence having the nucleotide denoted in Table 6, column four or seven at the polymorphic site in the polymorphic sequence, and (2) a sequence having a nucleotide other than the nucleotide denoted in Table 6, column four or seven. An example of the latter sequence is a polymorphic sequence having the nucleotide denoted in Table 6, column five or eight, respectively, at the polymorphic site in the polymorphic sequence.

For example, a polymorphism according to the invention includes a sequence polymorphism in the alpha B crystallin gene having the nucleotide sequence of GenBank Accession No. S45630, in which the adenosine at nucleotide 509 is replaced by guanosine. In some embodiments the polymorphic sequence includes a nucleotide sequence of the alpha B crystallin gene having the nucleotide sequence of GenBank Accession No. S45630, wherein the nucleotide at 509 is any nucleotide other that adenosine.

In some embodiments, the polymorphic sequence includes the full length of any one of the 16 genes in Table 6. In other embodiments, the polymorphic sequence includes a polynucleotide that is between 10 and 100 nucleotides, 10 and 75 nucleotides, 10 and 50 nucleotides, or 10 and 25 nucleotides in length.

TABLE 6

| Confirmed Gene | Acc # | TSC # | CSNP's found in 5'/3' UTR's | | | CSNP's found in coding region that change amino acids | | | |
|---|---|---|---|---|---|---|---|---|---|
| | | | Base Before | Base After | Position | Base Before | Base After | Position | Amino Acid Change |
| Alpha B crystallin | S45630 | TSC14 | A | G | 466 | A | G | 444 | ASP-GLY |
| | | | | | | A | G | 509 | THR-ALA |
| | | | | | | G | A | 518 | GLU-LYS |
| | | | | | | A | G | 519 | GLU-GLY |
| | | | | | | C | T | 542 | PRO-SER |
| Biglycan | J04599 | TSC16 | A | G | 261 | | | | |
| Endothelial plasminogen activator inhibitor | X04429 | TSC29 | A | C | 67 | G | A | 169 | ALA-THR |
| | | | C | T | 462 | G | C | 289 | VAL-LEU |
| Insulin-like growth factor binding protein-2 | M35410 | TSC3 | C | T | 816 | | | | |
| | | | G | A | 825 | | | | |
| | | | C | T | 828 | | | | |
| | | | C | T | 843 | | | | |
| Integrin β-5 subunit | J05633 | TSC31 | T | A | 973 | | | | |
| Laminin α 4 | X91171 | TSC18 | A | C | 6043 | C | T | 1754 | HIS-TYR |
| Novel gene fragment, 187 bp, 74% SI to human Lysyl oxidase-related protein (WS9-14) [U89942] | U89942 | TSC33 | A | G | 1285 | A | C | 1955 | MET-LEU |
| | | | C | T | 2008 | | | | |
| Macrophage capping protein | M94345 | TSC15 | C | A | 862 | | | | |
| Nuclear matrix protein 55 | U89867 | TSC36 | | | | G | C | 1159 | GLN-HIS |
| | | | | | | C | G | 1160 | GLN-GLU |
| | | | | | | G | C | 1183 | GLN-HIS |
| | | | | | | C | G | 1184 | GLN-GLU |
| Pre-B-cell stimulating factor homologue | L36033 | TSC2 | A | T | 2909 | | | | |
| | | | C | G | 2929 | | | | |
| Procollagen type IV α-1 chain | M11315 | TSC23 | C | A | 678 | | | | |
| Region 7 homeobox gene | M97676 | TSC9 | C | T | 1140 | | | | |
| SPARC/osteonectin | J03040 | TSC22 | G | A | 498 | C | G | 514 | PRO-ALA |
| | | | T | A | 501 | | | | |
| | | | C | T | 513 | | | | |
| | | | T | C | 519 | | | | |
| | | | C | T | 528 | | | | |
| | | | C | T | 753 | | | | |
| | | | C | T | 762 | | | | |
| | | | C | T | 774 | | | | |
| | | | C | G | 783 | | | | |
| | | | C | T | 789 | | | | |
| | | | C | T | 867 | | | | |
| Thrombospondin | X14787 | TSC32 | C | T | 1674 | G | A | 361 | ALA-THR |
| | | | T | C | 1851 | | | | |
| | | | C | T | 4203 | | | | |
| | | | A | C | 4339 | | | | |
| Tissue plasminogen activator | M15518 | TSC28 | C | T | 577 | | | | |
| Transforming growth factor β-1 binding protein | M34057 | TSC5 | G | A | 1686 | | | | |

The invention also provides a method of identifying a base occupying a polymorphic site in a nucleic acid. The method includes determining the nucleotide sequence of a nucleic acid that is obtained from a subject. The nucleotide sequence is compared to a reference sequence. Difference in the nucleotide sequence in the test sequence relative to the reference sequence indicates a polymorphic site in the nucleic acid.

Polymorphisms are detected in a target nucleic acid from an individual, e.g., a mammal, human or rodent (such as mouse or rat) being analyzed. For assay of genomic DNA, virtually any biological sample (other than pure red blood cells) is suitable. For example, convenient tissue samples include whole blood, semen, saliva, tears, urine, fecal material, sweat, buccal, skin and hair. For assay of cDNA or mRNA, the tissue sample must be obtained from an organ in which the target nucleic acid is expressed.

The detection of polymorphisms in specific DNA sequences, can be accomplished by a variety of methods including, e.g., restriction-fragment-length-polymorphism detection based on allele-specific restriction-endonuclease cleavage (Kan and Dozy, Lancet 11:910–912 (1978)), hybridization with allele-specific oligonucleotide probes (Wallace et al., Nucl. Acids Res. 6:3543–3557 (1978)), including immobilized oligonucleotides (Saiki et al., Proc. Nat. Acad. Sci. U.S.A., 86:6230–6234 (1969)) or oligonucleotide arrays (Maskos and Southern, Nucl. Acids Res. 21:2269–2270 (1993)), allele-specific PCR (Newton et al., Nucl. Acids Res. 17:2503–2516 (1989)), mismatch-repair detection (MRD) (Faham and Cox, Genome Res. 5:474–482 (1995)), binding of MutS protein (Wagner et al., Nucl. Acids Res. 23:3944–3948 (1995), denaturing-gradient gel electrophoresis (DGGE) (Fisher et al., Proc. Nat. Acad. Sci. U.S.A. 80:1579–1583 (1983)), single-strand-conformation-polymorphism detection (Orita et al., Genomics 5:874–879 (1983)), RNAase cleavage at mismatched base-pairs (Myers et al., Science 230:1242 (1985)), chemical (Cotton et al., Proc. Nat. Acad. Sci. U.S.A, 8:4397–4401 (1988)) or enzymatic (Youil et al., Proc. Nat. Acad. Sci. U.S.A. 92:87–91 (1995)) cleavage of heteroduplex DNA, methods based on allele specific primer extension (Syvanen et al., Genomics 8:684–692 (1990)), genetic bit analysis (GBA) (Nikiforov et al., Nucl. Acids Res. 22:4167–4175 (1994)), the oligonucleotideligation assay (OLA) (Landegren et al., Science 241:1077 (1988)), the allele-specific ligation chain reaction (LCR) (Barrany, Proc. Nat. Acad. Sci. U.S.A. 88:189–193 (1991)), gap-LCR (Abravaya et al., Nucl Acids Res 23:675–682 (1995)), radioactive and/or fluorescent DNA sequencing using standard procedures well known in the art, and peptide nucleic acid (PNA) assays (Orum et al., Nucl. Acids Res, 21:5332–5356 (1993); Thiede et al., Nucl. Acids Res. 24:983–984 (1996)).

For the purposes of identifying single nucleotide polymorphisms, "specific hybridization" or "selective hybridization" refers to the binding, or duplexing, of a nucleic acid molecule only to a second particular nucleotide sequence to which the nucleic acid is complementary, under suitably stringent conditions when that sequence is present in a complex mixture (e.g., total cellular DNA or RNA). "Stringent conditions" are conditions under which a probe will hybridize to its target subsequence, but to no other sequences. Stringent conditions are sequence-dependent and are different in different circumstances. Longer sequences hybridize specifically at higher temperatures than shorter ones. Generally, stringent conditions are selected such that the temperature is about 5° C. lower than the thermal melting point (Tm) for the specific sequence to which hybridization is intended to occur at a defined ionic strength and pH. The Tm is the temperature (under defined ionic strength, pH, and nucleic acid concentration) at which 50% of the target sequence hybridizes to the complementary probe at equilibrium. Typically, stringent conditions include a salt concentration of at least about 0.01 to about 1.0 M Na ion concentration (or other salts), at pH 7.0 to 8.3. The temperature is at least about 30° C. for short probes (e.g., 10 to 50 nucleotides). Stringent conditions can also be achieved with the addition of destabilizing agents such as formamide. For example, conditions of 5×SSPE (750 mM NaCl, 50 mM NaPhosphate, 5 mM EDTA; pH 7.4) and a temperature of 25–30° C. are suitable for allelespecific probe hybridizations.

"Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al.; or Current Protocols in Molecular Biology, Ausubel et al., eds., Greene Publishing and Wiley-Interscience, New York (1987).

Many of the methods described above require amplification of DNA from target samples. This can be accomplished by e.g., PCR. See generally, PCR Technology: Principles and Applications for DNA Amplification (H. A. Erlich, ed., Freeman Press, N.Y., N.Y., 1992); PCR Protocols: A Guide to Methods and Applications (Innis, et al., eds., Academic Press, San Diego, Calif., 1990); Mattila et al., Nucl. Acids Res. 19, 4967 (1991); Eckert et al., PCR Methods and Applications 1, 17 (1991); PCR (McPherson et al., eds., IRL Press, Oxford); and U.S. Pat. No. 4,683,202.

Other suitable amplification methods include the ligase chain reaction (LCR), (see Wu and Wallace, Genomics 4, 560 (1989); Landegren et al., Science 241, 1077 (1988)), transcription amplification (Kwoh et al., Proc. Nat. Acad. Sci. U.S.A. 86, 1173 (1989)), and self-sustained sequence replication (Guatelli et al., Proc. Nat. Acad. Sci. U.S.A., 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The invention also provides a method of selecting an individualized therapeutic agent for treating a TSC associated condition, e.g., subungual fibroma, in a subject using TSCX polymorphisms. The therapeutic agent can be identified by providing a nucleic acid sample from the subject, determining the nucleotide sequence of at least a portion of one or more of the TSCX1–41 sequences, and comparing the TSCX nucleotide sequence in the subject to the corresponding TSCX nucleic acid sequence in a reference nucleic acid sample. The reference nucleic acid sample is obtained from a reference individual (who is preferably as similar to the test subject as possible), whose responsiveness to the agent for treating the TSC associated pathology is known. The presence of the same sequence in the test and reference nucleic acid sample indicates the subject will demonstrate the same responsiveness to the agent as the reference individual, while the presence of a different sequence indicates the subject will have a different response to the therapeutic agent.

Similarly, the TSCX-associated sequence polymorphisms can be used to predict the outcome of treatment for a TSC associated pathology, e.g., subungual fibroma, in a subject. A region of an TSCX nucleic acid sequence from the subject is compared to the corresponding TSCX sequence in a reference individual whose outcome in response to the treatment for the TSC associated pathology is known. A similarity in the TSCX sequence in the test subject as compared to the sequence in the reference individual suggests the outcome in the subject will be the same as that of the reference individual. An altered TSCX sequence in the test and reference individual indicates the outcome of treatment will differ in the subject and reference individuals.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule encoding a polypeptide comprising an amino acid sequence of SEQ ID NO:2, or the complement of said nucleic acid molecule.

2. The isolated nucleic acid molecule of claim 1, wherein said isolated nucleic acid molecule hybridizes under conditions comprising 6×SSC, 50 mM Tris-HCl (pH7.5), 1 mM EDTA, 0.02% PVP, 0.02% Ficoll; 0.02% BSA, and 500 mg/ml denatured salmon sperm DNA at 65° C. to a nucleic acid sequence complementary to a nucleic acid molecule comprising the sequence of nucleotides 168–1217 of SEQ ID NO:1, or the complement of said isolated nucleic acid molecule.

3. The nucleic acid molecule of claim 1, wherein said nucleic acid molecule comprises nucleotides 168–1217 of SEQ ID NO:1, or the complement of said nucleic acid molecule.

4. The nucleic acid molecule of claim 1, wherein said nucleic acid molecule comprises SEQ ID NO:1, or the complement of said nucleic acid molecule.

5. A nucleic acid vector comprising the nucleic acid molecule of claim 1.

6. An isolated host cell comprising the vector comprising the isolated nucleic acid molecule of claim 5.

7. A composition comprising the nucleic acid molecule of claim 1 and a carrier.

8. A method of producing a polypeptide, said method comprising culturing an isolated host cell comprising thevectocomprisin g the nucleic acid molecule of claim 5 under conditions allowing for expression of a polypeptide encoded by said nucleic acid molecule.

* * * * *

SEQUENCE LISTING

```
<160> NUMBER OF SEQ ID NOS: 18

<210> SEQ ID NO 1
<211> LENGTH: 1637
<212> TYPE: DNA
<213> ORGANISM: Homo sapiens
<220> FEATURE:
<221> NAME/KEY: CDS
<222> LOCATION: (168)..(1217)

<400> SEQUENCE: 1
caaataaaaa tggtggagtc tgaaaaagga ctgggtcagc aagaataaaa acacaaaaca        60
gctggaggag ccaagatggc cgaataggaa cagctccggt ctacagctcc cagcgtgagc       120
gacgcagaag acgggtgatt tctgcatttc cataacagat tggagcc atg gct ttg         176
                                                    Met Ala Leu
                                                    1 gaa cag aac cag tca aca gat tat tat tat gag gaa aat gaa atg aat         224
Glu Gln Asn Gln Ser Thr Asp Tyr Tyr Tyr Glu Glu Asn Glu Met Asn
        5                  10                  15 ggc act tat gac tac agt caa tat gaa ctg atc tgt atc aaa gaa gat         272
Gly Thr Tyr Asp Tyr Ser Gln Tyr Glu Leu Ile Cys Ile Lys Glu Asp
 20                  25                  30                  35 gtc aga gaa ttt gca aaa gtt ttc ctc cct gta ttc ctc aca ata gtt         320
Val Arg Glu Phe Ala Lys Val Phe Leu Pro Val Phe Leu Thr Ile Val
                 40                  45                  50 ttc gtc att gga ctt gca ggc aat tcc atg gta gtg gca att tat gcc         368
Phe Val Ile Gly Leu Ala Gly Asn Ser Met Val Val Ala Ile Tyr Ala
             55                  60                  65 tat tac aag aaa cag aga acc aaa aca gat gtg tac atc ctg aat ttg         416
Tyr Tyr Lys Lys Gln Arg Thr Lys Thr Asp Val Tyr Ile Leu Asn Leu
         70                  75                  80 gct gta gca gat tta ctc ctt cta ttc act ctg cct ttt tgg gct gtt         464
Ala Val Ala Asp Leu Leu Leu Leu Phe Thr Leu Pro Phe Trp Ala Val
     85                  90                  95 aat gca gtt cat ggg tgg gtt tta ggg aaa ata atg tgc aaa ata act         512
Asn Ala Val His Gly Trp Val Leu Gly Lys Ile Met Cys Lys Ile Thr
100                 105                 110                 115 tca gcc ttg tac aca cta aac ttt gtc tct gga atg cag ttt ctg gct         560
Ser Ala Leu Tyr Thr Leu Asn Phe Val Ser Gly Met Gln Phe Leu Ala
                120                 125                 130 tgc atc agc ata gac aga tat gtg gca gta act aat gtc ccc agc caa         608
Cys Ile Ser Ile Asp Arg Tyr Val Ala Val Thr Asn Val Pro Ser Gln
            135                 140                 145 tca gga gtg gga aaa cca tgc tgg atc atc tgt ttc tgt gtc tgg atg         656
Ser Gly Val Gly Lys Pro Cys Trp Ile Ile Cys Phe Cys Val Trp Met
        150                 155                 160 gct gcc atc ttg ctg agc ata ccc cag ctg gtt ttt tat aca gta aat         704
Ala Ala Ile Leu Leu Ser Ile Pro Gln Leu Val Phe Tyr Thr Val Asn
    165                 170                 175
```

| | | | | | | | | | | | | | | | | |
|---|---|---|---|---|---|---|---|---|---|---|---|---|---|---|---|---|
| gac | aat | gct | agg | tgc | att | ccc | att | ttc | ccc | cgc | tac | cta | gga | aca | tca | 752 |
| Asp | Asn | Ala | Arg | Cys | Ile | Pro | Ile | Phe | Pro | Arg | Tyr | Leu | Gly | Thr | Ser | |
| 180 | | | | 185 | | | | | 190 | | | | | 195 | | |
| atg | aaa | gca | ttg | att | caa | atg | cta | gag | atc | tgc | att | gga | ttt | gta | gta | 800 |
| Met | Lys | Ala | Leu | Ile | Gln | Met | Leu | Glu | Ile | Cys | Ile | Gly | Phe | Val | Val | |
| | | | | 200 | | | | | 205 | | | | | 210 | | |
| ccc | ttt | ctt | att | atg | ggg | gtg | tgc | tac | ttt | atc | acg | gca | agg | aca | ctc | 848 |
| Pro | Phe | Leu | Ile | Met | Gly | Val | Cys | Tyr | Phe | Ile | Thr | Ala | Arg | Thr | Leu | |
| | | | | 215 | | | | | 220 | | | | | 225 | | |
| atg | aag | atg | cca | aac | att | aaa | ata | tct | cga | ccc | cta | aaa | gtt | ctg | ctc | 896 |
| Met | Lys | Met | Pro | Asn | Ile | Lys | Ile | Ser | Arg | Pro | Leu | Lys | Val | Leu | Leu | |
| | | | | 230 | | | | | 235 | | | | | 240 | | |
| aca | gtc | gtt | ata | gtt | ttc | att | gtc | act | caa | ctg | cct | tat | aac | att | gtc | 944 |
| Thr | Val | Val | Ile | Val | Phe | Ile | Val | Thr | Gln | Leu | Pro | Tyr | Asn | Ile | Val | |
| | | | | 245 | | | | | 250 | | | | | 255 | | |
| aag | ttc | tgc | cga | gcc | ata | gac | atc | atc | tac | tct | ctg | atc | acc | agc | tgc | 992 |
| Lys | Phe | Cys | Arg | Ala | Ile | Asp | Ile | Ile | Tyr | Ser | Leu | Ile | Thr | Ser | Cys | |
| 260 | | | | 265 | | | | | 270 | | | | | 275 | | |
| aac | atg | agc | aaa | cgc | atg | gac | atc | gcc | atc | caa | gtc | aca | gaa | agc | att | 1040 |
| Asn | Met | Ser | Lys | Arg | Met | Asp | Ile | Ala | Ile | Gln | Val | Thr | Glu | Ser | Ile | |
| | | | | 280 | | | | | 285 | | | | | 290 | | |
| gca | ctc | ttt | tac | agc | tgc | ctc | aac | cca | atc | ctt | tat | gtt | ttt | atg | gga | 1088 |
| Ala | Leu | Phe | Tyr | Ser | Cys | Leu | Asn | Pro | Ile | Leu | Tyr | Val | Phe | Met | Gly | |
| | | | | 295 | | | | | 300 | | | | | 305 | | |
| gca | tct | ttc | aaa | aac | tac | gtt | atg | aaa | gtg | gcc | aag | aaa | tat | ggg | tcc | 1136 |
| Ala | Ser | Phe | Lys | Asn | Tyr | Val | Met | Lys | Val | Ala | Lys | Lys | Tyr | Gly | Ser | |
| | | | | 310 | | | | | 315 | | | | | 320 | | |
| tgg | aga | aga | cag | aga | caa | agt | gtg | gag | gag | ttt | cct | ttt | gat | tct | gag | 1184 |
| Trp | Arg | Arg | Gln | Arg | Gln | Ser | Val | Glu | Glu | Phe | Pro | Phe | Asp | Ser | Glu | |
| | 325 | | | | | 330 | | | | | 335 | | | | | |
| ggt | cct | aca | gag | cca | acc | agt | act | ttt | agc | att | taaaggtaaa | | actgctctgc | | | 1237 |
| Gly | Pro | Thr | Glu | Pro | Thr | Ser | Thr | Phe | Ser | Ile | | | | | | |
| 340 | | | | 345 | | | | | 350 | | | | | | | |

| | |
|---|---|
| cttttgcttg gatacatatg aatgatgctt tcccctcaaa taaaacatct gcattattct | 1297 |
| gaaactcaaa tctcagacgc cgtggttgca acttataata agaatgggt tgggggaagg | 1357 |
| gggagaaata aaagccaaga agaggaacaa gataataaat gtacaaaaca tgaaaattaa | 1417 |
| aatgaacaat ataggaaaat aattgtaaca ggcataagtg aataacactc tgctgtaacg | 1477 |
| aagaagagct tgtggtgat aattttgtat cttggttgca gtggtgctta tacaaatcta | 1537 |
| cacaagtgat aaaatgacac agaactatat acacacattg taccaatttc aatttcctgg | 1597 |
| ttttgacatt atagtataat tatgtaagat ggaaccattg | 1637 |

<210> SEQ ID NO 2
<211> LENGTH: 350
<212> TYPE: PRT
<213> ORGANISM: Homo sapiens

<400> SEQUENCE: 2

| | | | | | | | | | | | | | | |
|---|---|---|---|---|---|---|---|---|---|---|---|---|---|---|
| Met | Ala | Leu | Glu | Gln | Asn | Gln | Ser | Thr | Asp | Tyr | Tyr | Tyr | Glu | Asn |
| 1 | | | | 5 | | | | | 10 | | | | | 15 |
| Glu | Met | Asn | Gly | Thr | Tyr | Asp | Tyr | Ser | Gln | Tyr | Glu | Leu | Ile | Cys | Ile |
| | | | 20 | | | | | 25 | | | | | 30 | | |
| Lys | Glu | Asp | Val | Arg | Glu | Phe | Ala | Lys | Val | Phe | Leu | Pro | Val | Phe | Leu |
| | | 35 | | | | | 40 | | | | | 45 | | | |
| Thr | Ile | Val | Phe | Val | Ile | Gly | Leu | Ala | Gly | Asn | Ser | Met | Val | Val | Ala |
| | 50 | | | | | 55 | | | | | 60 | | | | |
| Ile | Tyr | Ala | Tyr | Tyr | Lys | Lys | Gln | Arg | Thr | Lys | Thr | Asp | Val | Tyr | Ile |

```
                65                  70                  75                  80
Leu Asn Leu Ala Val Ala Asp Leu Leu Leu Phe Thr Leu Pro Phe
                    85                  90                  95
Trp Ala Val Asn Ala Val His Gly Trp Val Leu Gly Lys Ile Met Cys
            100                 105                 110
Lys Ile Thr Ser Ala Leu Tyr Thr Leu Asn Phe Val Ser Gly Met Gln
        115                 120                 125
Phe Leu Ala Cys Ile Ser Ile Asp Arg Tyr Val Ala Thr Asn Val
    130                 135                 140
Pro Ser Gln Ser Gly Val Gly Lys Pro Cys Trp Ile Ile Cys Phe Cys
145                 150                 155                 160
Val Trp Met Ala Ala Ile Leu Leu Ser Ile Pro Gln Leu Val Phe Tyr
                165                 170                 175
Thr Val Asn Asp Asn Ala Arg Cys Ile Pro Ile Phe Pro Arg Tyr Leu
            180                 185                 190
Gly Thr Ser Met Lys Ala Leu Ile Gln Met Leu Glu Ile Cys Ile Gly
        195                 200                 205
Phe Val Val Pro Phe Leu Ile Met Gly Val Cys Tyr Phe Ile Thr Ala
    210                 215                 220
Arg Thr Leu Met Lys Met Pro Asn Ile Lys Ile Ser Arg Pro Leu Lys
225                 230                 235                 240
Val Leu Leu Thr Val Val Ile Val Phe Ile Val Thr Gln Leu Pro Tyr
                245                 250                 255
Asn Ile Val Lys Phe Cys Arg Ala Ile Asp Ile Ile Tyr Ser Leu Ile
            260                 265                 270
Thr Ser Cys Asn Met Ser Lys Arg Met Asp Ile Ala Ile Gln Val Thr
        275                 280                 285
Glu Ser Ile Ala Leu Phe Tyr Ser Cys Leu Asn Pro Ile Leu Tyr Val
    290                 295                 300
Phe Met Gly Ala Ser Phe Lys Asn Tyr Val Met Lys Val Ala Lys Lys
305                 310                 315                 320
Tyr Gly Ser Trp Arg Arg Gln Arg Gln Ser Val Glu Glu Phe Pro Phe
                325                 330                 335
Asp Ser Glu Gly Pro Thr Glu Pro Thr Ser Thr Phe Ser Ile
            340                 345                 350

<210> SEQ ID NO 3
<211> LENGTH: 220
<212> TYPE: DNA
<213> ORGANISM: Homo sapiens

<400> SEQUENCE: 3
caattgacct cctacaggaa gtttggcttt gagattattg agacaaagaa gaactactat      60
aagaggatag agcccgcaga tgctcatgtg ctgcagaaaa acctcaaagt tccttctggt     120
cagaatgcag atgtgcaaaa gacagacaac tgaacaaatt acaaatgaac tttcttgcac     180
ttgcttgtcg ccaaataaaa gagaggccca ttgattcctc                           220

<210> SEQ ID NO 4
<211> LENGTH: 3579
<212> TYPE: DNA
<213> ORGANISM: Artificial Sequence
<220> FEATURE:
<223> OTHER INFORMATION: Description of Artificial Sequence: Assembled
      contig

<400> SEQUENCE: 4
```

-continued

```
tttttttttt tttttttttt ttttaccaga acatcacata agtttatttc agatgtaaca      60
gcaatgttaa aattgacaag tttaattctt aactgcacca agtaaactta gccatttaag     120
tatttttta agttattccc tccaaaaaac tgagggagct tttctttcc accaccacac      180
catggtttcc caatagttct cttttggag gacttttcaa ttgatgagta aactgcttta      240
gatatttcag aacttcattc cccaaatgaa agctaatctg acaaactat atattgcata      300
gatttctcta cagattcttt gctttaaaac ctaaatgcaa ctaacatagt gtaattttaa      360
cctatttgcc ccacagtaaa aactatctgt cctgaaaaat atgatggata tatcctgtga     420
ttttccagtt aacagaattg ttctacttca aagataatta ttatcatata tcaaaataac      480
cagctcaaca taggacatta cttcagtctt tactgactca taggcatatg aaacttggtg      540
ccccagcttt ttacctcttc cacattctcc tcctcctcca taagtggatg gaattattta     600
actaagtttg atgtaggaca attaacccct tacaaacatt tacaattcag gttaagtcac      660
tgactaccgt ggaaaaagaa actctatata taatgatagg gagcctacac actcaattca      720
aaatttaata ttttttcctc cttaaataac atgtacttgt catgaggcag ctattaggtt      780
ttcaataacc acatttaggg atacattcat aggactgatt agatagtcca ggtgaaatgg     840
ttatagaaat agaggcagtg tcatctcaga aaaccattta tatatcaaag tctattttga      900
tatctgggaa gtttacaaaa aggctgctgc attcttcaaa ctacttatgc cttctgtaac      960
tcaagcactc ttctcttgcc aagagcaagc tgaagcttat tcatgaagat aaaggtgctt    1020
aacgctaaac ttttcttcta agcttagatt tggattgttt aagaaacgaa taccccaaa     1080
aaaccagcaa ggtctttcta cattttacc atcttaagat tagaaccta taaactcatt     1140
catcaactgt cttcttttc tgtattattc ttggcactca agattgttga agtctactgc    1200
actttgtact ttcacattct caaataaaaa cttaaggtta taaagtgtgc ataaacattt    1260
tataaaataa ttttgtcatt taacatattt ggaaatgaga ctttataccg caatttttaca   1320
taagaggata aatatgaatg aaacttcctt ttaaagtcaa atgacagaaa gctcaagccc    1380
tgtgcattat tttaaagtct gagaacattt ctaaatagtg gagatgggac tacaaaagga   1440
aaacatgaat atttcagatg tctcccatct tacaaagtta tcaatctgtc aaagccctcc   1500
gtgtgtgccg gaaaatgatc tggcataaac cagtcctctc agtggaggag gtcacagtga   1560
catttgtatt attaacattt tacacttcta ttttccaag aatagaagca atatgtttaa    1620
taattacccc tgcctcaaat ccttaaactc aatatcacag gcactgagta taagcaaatc    1680
tgggatgtcc tccaacagat gtgcaatagc acagctatgt tattctcaaa aatactattt    1740
tttcctataa aatcaaatgc tcagtggcca cacttttaac agctggcatt agatgacagt    1800
aattgaattt tttgtgtcac agcccatcta agcttccttt taggtatttt ttagtatgtc   1860
caagagaaaa cacctgcttc aggtttattt aggggtagtg acctataagg acatcaactc    1920
aattttaag gttagactat tgttgggttt actgaagaaa aaggaacggg aaaaaattaa     1980
atcacaacac acctctttag gtcagttaaa ggccatatct ctagctggga tattaaaaaa   2040
aattaatctc accagcccaa attctaaaag ttaatgccac tagtaacaat caacagcagg    2100
aaaaacaaac ctgctaacaa ccagcccact cattagcaaa aaagcagttt aactcaaata   2160
cttagaccaa agtataacac taaaccaaac tgccccaccc accagcaaga agagaagata   2220
taattactta aaaatcaaca taagcttagt atttcttaca aggataacaa tgttccaact    2280
cccgagagag tgctcagaag gactaaaggt ggagtgaagg caatgtctag ggattagtat    2340
```

-continued

```
cccaaagtgt taaaaaccc aaagtaccac aaacacactc aacttgtcta tgaattagag    2400
aacaagatac tgctgctgct tcttttttgtc ttttgaaata tacaatgttt tgtaggctct   2460
gcccttcaat gtgaaagcag gacattaaat ttgaaattat ttgacaatta aatgtttagg    2520
accatctaac ttcaactgca aaactaaaca gatctacctt gtccttcctt caaaccacct    2580
cacaaaaata agagaaaaca attcaaacat gattatttt ttaaagtcct tgaaagtatt    2640
aaaactctca gagaaaagga aaggaagaaa gaaaaacaag aacaaggagg gagaaaagct    2700
ttaaaagaaa agtgttgggg tgggggagga atcaatgggc ctctctttta tttggcgaca    2760
agcaagtgca agaaagttca tttgtaattt gttcagttgt ctgtcttttg cacatctgca    2820
ttctgaccag aaggaacttt gaggtttttc tgcagcacat gagcatctgc gggctctatc    2880
ctcttatagt agttcttctt tgtctcaata atctcaaagc caaacttcct gtagaagtca    2940
attgccgact cattgctgat ctggacatgc agataaatgt tgtcaaaagt accatctttt    3000
tcacagatgt ttaagacatg atttaacatt ttagttccta ttcctagcct tcggtaaggt    3060
gccagacatc ctagtgtcat gatgtaaagt ctcttctgat tctgtgaatg atccacccta    3120
cagcatactg cacctacagc aatatcattg aaataggcaa gttttgctag ctcgccaacc    3180
tccagcacat ccttgtagaa cttgtcattg tagctgactg gaaagatgac ctgattcaat    3240
cttttcaact gtttaatatt gtgtggtgtc acatctccca gctcgatccg gcctttcatc    3300
ttccccgcct gctgaggccg tcgttaccac cgatatcaac gccgtcgtag tcgccgccct    3360
tgggtctccg cacccttagc tcgggccact caaccccgca agccggcctc ctagcctggg    3420
cagggagctg tgcgagcaac gaaggccgcg agagtcgagt gagggcttga gtctggtggg    3480
agcgggagtg tctcccgccg ccgcgcttgt gccgccgctt ctccacacgt gcactcgggt    3540
ctctcggctc cctcccgccg tgccgccagc cagacccgc                          3579
```

<210> SEQ ID NO 5
<211> LENGTH: 182
<212> TYPE: DNA
<213> ORGANISM: Homo sapiens

<400> SEQUENCE: 5

```
tgatcacggc caccctcacc cccgagagag acgcctacgt ggaagcagtg ctgtcggtct     60
ccaacgccag cgtggcccag ctgcataccg ctgggtacag gagagagttc ctggaatacc    120
accgccctcc aggagctttg catacctgcg ggggcccggg ggcattccac ctcatcgtgc    180
ac                                                                  182
```

<210> SEQ ID NO 6
<211> LENGTH: 647
<212> TYPE: DNA
<213> ORGANISM: Artificial Sequence
<220> FEATURE:
<223> OTHER INFORMATION: Description of Artificial Sequence: Assembled
      contig

<400> SEQUENCE: 6

```
cccgaagtca cctcctgtag cttccccagg agctccggtg ccttctctgg tgtcttttc      60 tgcgggctc acccagaagc ctttcccag tgatgggggc gttgtcctct ttaacaaagt     120
gctggtgaac gacggggatg tttacaaccc cagcaccggg gtcttcacgg ctccttatga    180
tgggcgctac ctgatcacgg ccaccctcac ccccgagaga gacgcctacg tggaagcagt    240
gctggcggtc tccaacgcca gcgtggccca gctgcatacc gctgggtaca ggagagagtt    300
```

| cctggaatac caccgccctc caggagcttt gcatacctgc gggggcccgg gggcattcca | 360 |
| cctcatcgtg cacctgaagg cgggagatgc agtcaacgtc gtggtgactg ggggcaagct | 420 |
| ggctcacaca gactttgatg aaatgtactc cacatttagt ggggttttct tatatccttt | 480 |
| cctttcccac ctctaaggtg gctggggaga tgtcagggga aagatagata gttgtaaaaa | 540 |
| ctctaaagct ttaatatatt cggtttgtat gtaatggaag cacggggcta gagtttccac | 600 |
| ataggcccca acataaaggc cttccctcgc tgttgaggcc accatgc | 647 |

<210> SEQ ID NO 7
<211> LENGTH: 352
<212> TYPE: DNA
<213> ORGANISM: Homo sapiens
<220> FEATURE:
<223> OTHER INFORMATION: Any n may be A, G, C, or T.

<400> SEQUENCE: 7

| gctagcaccg ggtctgcacc tgcggggcat ccgggacgcg ggaggccggt actgccagga | 60 |
| gcaggacctg tgctgccgcg gccgtgcnac gactgtgccc tgccctacct gggcgccatc | 120 |
| tgttactgtg acctcttctg caaccgcacg gtctccgact gctgccctga cttctgggac | 180 |
| ttctgcctcg gcgtgccacc ccctttttccc ccgatccaag gatgtatgca tggaggtcnt | 240 |
| atctatccag tcttgggaac gtactgggac aactgtaacc gtnaccctg ccaggagaac | 300 |
| aggcagtggc agtgtgacca agaaccatgc ctggtggatc cagacatgat ca | 352 |

<210> SEQ ID NO 8
<211> LENGTH: 683
<212> TYPE: DNA
<213> ORGANISM: Artificial Sequence
<220> FEATURE:
<223> OTHER INFORMATION: Description of Artificial Sequence: Assembled contig

<400> SEQUENCE: 8

| cgtcgaatat ccatgcagcc gcgtccatca gctactacgg cttcggcagc acggtggcct | 60 |
| actactacta cctgttgcca ggcctcagct tgctggatgc cagagtcatg actccatact | 120 |
| tgcagcagcg cctgggctgg cacgtggact gcacgcgcct tatcgccgcc taccgcgccc | 180 |
| tggtgctgcc tgtggccttc gtgctggcgg tggcttgcac tgtggcctgc tgcaagagcc | 240 |
| gtaccgactg gtgtacctac ccgttcgcgc tgcgcaccct cgtcttcgtc atgccgctca | 300 |
| gcatggcctg ccccattatg ctctgagcat gtctggatct tcgaccaggc atggggagaa | 360 |
| cccggtcaca ctgccactgc ctgttctcct ggcagggggca acggttacag ttgtcccagt | 420 |
| acgttcccaa gactggatag atacgacctc catgcataca tccttggatc gggggaaaag | 480 |
| ggggtggcac gccgaggcag aagtcccaga agtcagggca gcagtcggag accgtgcggt | 540 |
| tgcagaagag gtcacagtaa cagatggcgc ccaggtaggg cagggcacag tcgtcggcac | 600 |
| ggccgcggca gcacaggtcc tgctcctggc agtaccggcc tcccgcgtcc cggatgcccc | 660 |
| gcaggtgcag acccggtgct agc | 683 |

<210> SEQ ID NO 9
<211> LENGTH: 187
<212> TYPE: DNA
<213> ORGANISM: Homo sapiens
<220> FEATURE:
<223> OTHER INFORMATION: Any n may be A, G, C or T.
<223> OTHER INFORMATION: r is a purine nucleotide, G or A.

<400> SEQUENCE: 9

```
rccggcatga cattgattgc cagtgggtgg atatcacaga tgtgggcccc gggaattata      60
tcttccaggt gattgtgaac ccccactatg aagtggcaga gtnngatttc tccaacaata    120
tgctgcagtg ccgctgcaag tatgatgggc accgggtctg gctgcacaac tgccacacag    180
ggaattc                                                              187
```

<210> SEQ ID NO 10
<211> LENGTH: 327
<212> TYPE: DNA
<213> ORGANISM: Artificial Sequence
<220> FEATURE:
<223> OTHER INFORMATION: Description of Artificial Sequence: Assembled
      contig

<400> SEQUENCE: 10

```
acgcgtgaag ggcatggctc caataagctg aggtatctgg tgtatcggca gcagctagga     60
gtgtgcagtg acagcttcag atgaggttgt tcctgagacg ctgttcctgc tccagggaga    120
gttctgcatt ggctgggtat gaattccctg tgtggcagtt gtgcagccag acccggtgcc    180
catcatactt gcagcggcac tgcagcatat tgttggagaa atctgactct gccacttcat    240
agtgggggtt cacaatcacc tggaagatat aattcccggg gcccacatct gtgatatcca    300
cccactggca atcaatgtca tgccggc                                        327
```

<210> SEQ ID NO 11
<211> LENGTH: 189
<212> TYPE: DNA
<213> ORGANISM: Homo sapiens

<400> SEQUENCE: 11

```
ccatggcagg cagtgaaaag agccaggagt cctgggttct agtccctgct ctgcccccaa     60
ctggctgtat aacctttgaa aaatcatttt ctttgtctga gtctctggtt ctccgtcagc    120
aacaggctgg cataaggtcc cctgcaggtt ccttctagct ggagcactca gagcttccct    180
gactgccag                                                            189
```

<210> SEQ ID NO 12
<211> LENGTH: 490
<212> TYPE: DNA
<213> ORGANISM: Artificial Sequence
<220> FEATURE:
<223> OTHER INFORMATION: Description of Artificial Sequence: Assembled
      contig

<400> SEQUENCE: 12

```
tttttttgttg gttatccacg agggtttatt tccacttgag accctgatg ggagcaacaa      60 tgcagaggcc ctttacagaa tggtgaagca tatgatataa agatacaaa atataacatc     120 atttacatgt gccattcata dacaaaggag tgtgtttgat gagccggttg gagaaagtgg    180
acacttccca atcattccct ctcagggget tctctggctg ccttgctctg atggagattt    240
tcaggagaga gagctccagg gagaaggaga acaatcagcc ctgtgagggc cagagaggct    300
gctagcagtc agggaagctc tgagtgctcc agctagaagg aacctgcagg ggaccttatg    360
ccagcctgtt gctgacggag aaccagagac tcagacaaag aaaatgattt ttcaaaggtt    420
atacagccag ttgggggcag agcagggact agaacccagg actcctggct cttttcactg    480
cctgccatgg                                                           490
```

<210> SEQ ID NO 13

<211> LENGTH: 267
<212> TYPE: DNA
<213> ORGANISM: Homo sapiens
<220> FEATURE:
<223> OTHER INFORMATION: Any n may be A, G, C, or T.

<400> SEQUENCE: 13

| aagctttaca agtatttatt ttataaggct tagacagaat tattggagtt ttaaattaag | 60 |
| tgtattggaa aagaaaggat ggtatgtgta tgaaatgtta agatcctacg caacactnct | 120 |
| attttttcc tttaatattt gtgctgcata acaaaagcca ctagactgtt actgtcttgt | 180 |
| ctgtccatgt gttaacagca tttcttaatg atgtatatat ggagtggtct tctatcatag | 240 |
| tgaagaattt aaagagaaag tcaattg | 267 |

<210> SEQ ID NO 14
<211> LENGTH: 404
<212> TYPE: DNA
<213> ORGANISM: Artificial Sequence
<220> FEATURE:
<223> OTHER INFORMATION: Description of Artificial Sequence: Assembled contig

<400> SEQUENCE: 14

| aagctttaca agtatttatt ttataaggct tagacagaat tattggagtt ttaaattaag | 60 |
| tgtattggaa aagaaaggat ggtatgtgta tgaaatgtta agatcctacg caacactgct | 120 |
| attttttcc tttaatattt gtgctgcata acaaaagcca ctagactgtt actgtcttgt | 180 |
| ctgtccatgt gttaacagca tttcttaatg atgtatatat ggagtggtct tcaatcatag | 240 |
| tgaagaattt aaagagaaag tcaattgtat tggcatttt aataaggaac aaaattagtt | 300 |
| cgtctaaggg gactggctgg ccacatattt gttccttgcc catatgcttt ctacttcttg | 360 |
| ttcttattat ggaaattatg gattttggaa ggcctctgga atgg | 404 |

<210> SEQ ID NO 15
<211> LENGTH: 487
<212> TYPE: DNA
<213> ORGANISM: Homo sapiens
<220> FEATURE:
<223> OTHER INFORMATION: Any n may be A, G, C, or T.

<400> SEQUENCE: 15

| gtggcacgtg ctcgtaatcc cagctactcg ggaggctgag gcaggagaat caattgaacc | 60 |
| tgggaggcag aggttgcagt gagccgagat ggcgccattg cactccagcc tgggtgacaa | 120 |
| aagcaaaagt ccatcttaag aaatatatat atatattata tatattctta gttctaagat | 180 |
| ttcctttaat tctatgattc tctggattta aatgcattat tcatatttct tgaagcttag | 240 |
| atacagtcta attcatagca accatatctg ctttatccta ggtgagggta gcagtccaca | 300 |
| atggaataga agaaatccc attataacaa atgacaaatt anatatcatg aatccttctg | 360 |
| tctgactaac tcaataactt tctataaaag ccaatggaat tcaaatagga gctaggagac | 420 |
| aacaagttat atatgacagt ggaggttgta ttcctttat attgctgaga aaactagtta | 480 |
| aatgatc | 487 |

<210> SEQ ID NO 16
<211> LENGTH: 1547
<212> TYPE: DNA
<213> ORGANISM: Artificial Sequence
<220> FEATURE:
<223> OTHER INFORMATION: Description of Artificial Sequence: Assembled contig
<221> NAME/KEY: misc_feature
<222> LOCATION: (721)..(1011)
<223> OTHER INFORMATION: Alu fragment

<400> SEQUENCE: 16

```
ttttttttttt tttttttttta accagaacaa aagacatttt attttgagaa ataaattgga      60
aaaaaatatt ttaaaatgtt taatttgcaa tatacataat actggaattg aaatgctgtc      120
tgatggaaat gttgcaatgt ggagtaggag ggtcaagttc gtgaagatat tcttaaaatt      180
aatcttggaa actctgtgcc tatgaggttt ctctaaagtg gctaaaatat gcatttaata      240
tgttgtctaa atgagtacat ttaattctag agactgtaag gagtagagat tatatgctttt    300
ggggcttttt gtagcatttt tttaaaatca gttgtacaga tcccattaaa cgaaattgtt       360
tcttaacagc aagaatctga tcatttaact agttttctca gcaatataaa aggaatacaa      420
cctccactgt catatataac ttgttgtctc ctagctccta tttgaattcc attggctttt      480
atagaaagtt attgagttag tcagacagaa ggattcatga tatataatt gtcatttgtt       540
ataatgggat tttcttctat tccattgtgg actgctaccc tcacctagga taaagcagat      600
atggttgcta tgaattagac tgtatctaag cttcaagaaa tatgaataat gcatttaaat      660
ccagagaatc atagaattaa aggaaatctt agaactaaga atatatataa tatatatata      720
tatttcttaa gatggacttt tgcttttgtc acccaggctg gagtgcaatg gcgccatctc      780
ggctcactgc aacctctgcc tcccgtgttc aagcgattct cctgcctcag cctcccaagt      840
agctgggatt acaagcacgt gccaccacac ccagctaatt tttgtatttt tagtagaaac      900
agggtttcac cacgttggcc aggctggtct cgaactcctg acctcaggtt atctacccac      960
ctcagcctcc caagtattg tgattacagg tgtgagccac catgtccagc ctagtaccaa      1020
tcttagaca acagatgctt ataatcaata tactgcttag tagtaatttg gtatttgaag      1080
ttaatatact tacttaacaa aaaatccca gatcagatgt tttaaagttt taatatataaa     1140
ctaaattta aactataaat acttacctta aaatactaga aatcctaata tcatcaattc       1200
agtaagagct ctggcataga aaaatgtaac tacaaatcaa attattttt aaccagtgct       1260
ggatcttcat tacaaaataa ggggaaaaaa tcctctgctg tcatcaaaaa gttttccaaa      1320
ttatctgtaa acaccaagga attctattat tcttttttcaa ttctcttaat ttctacatct    1380
ttctgcctat agtgttttac ttccaatata gcacaaatcc atgctacata tgttgatttc      1440
tgttgcttat ctgattaatt caagtaaaaa ttctcagtac ttaccaagac acttttaaatt    1500
tctattagat aaccattagt atactactgg tttgtagtta aaagtac                   1547
```

<210> SEQ ID NO 17
<211> LENGTH: 192
<212> TYPE: DNA
<213> ORGANISM: Homo sapiens

<400> SEQUENCE: 17

```
gaattcgtgc ttgaggatca gctaggctgc aaaggtggag tctctcatct gatccagaag       60
gggtagaaga gtctgcacaa gcttctgtgc acctgggaat gtttcgtgcg ttgagaggag      120
aggtggggtc tcagcaggag gaggtcctgc aggtggtgct gcaagggtc ggctggccgc       180
agggaggccg gc                                                         192
```

<210> SEQ ID NO 18
<211> LENGTH: 112
<212> TYPE: DNA
<213> ORGANISM: Artificial Sequence -continued

```
<220> FEATURE:
<223> OTHER INFORMATION: Description of Artificial Sequence: Assembled
      contig

<400> SEQUENCE: 18
gtgcacacct cagggttcca gatccttgat ctcgtgacct ctgacctgca gtgacctcgc         60
caaccgacgc ggccgccccg ccacgccccc gccccaaggt gcaccgagat ct               112
```